United States Patent
Noy et al.

(10) Patent No.: US 12,311,053 B2
(45) Date of Patent: May 27, 2025

(54) NANOTUBE-VESICLE COMPOSITIONS AND USES THEREOF

(71) Applicants: Lawrence Livermore National Security, LLC, Livermore, CA (US); Max-Planck-Gesellschaft Zur Foerderung Dur Wissenschaften E.V., Munich (DE); Nga Thuy Ho, Oakland, CA (US)

(72) Inventors: Aleksandr Noy, Livermore, CA (US); Nga Thuy Ho, Oakland, CA (US); Gerhard Hummer, Munich (DE); Marc Siggel, Munich (DE)

(73) Assignees: LAWRENCE LIVERMORE NATIONAL SECURITY, LLC, Livermore, CA (US); THE REGENTS OF THE UNIVERSITY OF CALIFORNIA, Oakland, CA (US); MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 898 days.

(21) Appl. No.: 17/121,578

(22) Filed: Dec. 14, 2020

(65) Prior Publication Data

US 2021/0177756 A1 Jun. 17, 2021

Related U.S. Application Data

(63) Continuation of application No. PCT/US2020/064707, filed on Dec. 11, 2020.
(Continued)

(51) Int. Cl.
*A61K 9/1271* (2025.01)
*A61K 31/65* (2006.01)

(52) U.S. Cl.
CPC ............ *A61K 9/1271* (2013.01); *A61K 31/65* (2013.01)

(58) Field of Classification Search
CPC .... A61K 9/1271; A61K 31/65; A61K 31/704; B82Y 5/00
See application file for complete search history.

(56) References Cited

U.S. PATENT DOCUMENTS

| | | | |
|---|---|---|---|
| 5,376,253 | A | 12/1994 | Rychen et al. |
| 5,698,175 | A | 12/1997 | Hiura et al. |

(Continued)

FOREIGN PATENT DOCUMENTS

| | | |
|---|---|---|
| EP | 0 148 551 A2 | 7/1985 |
| EP | 1 340 544 A1 | 9/2003 |

(Continued)

OTHER PUBLICATIONS

Seung I. Cha, Kyung T. Kim, Kyong H. Lee, Chan B. Mo, Yong J. Jeong, Soon H. Hong. "Mechanical and electrical properties of cross-linked carbon nanotubes." Carbon, vol. 46, 2008, pp. 482-488. (Year: 2008).*

(Continued)

*Primary Examiner* — Isaac Shomer
(74) *Attorney, Agent, or Firm* — Foley & Lardner LLP

(57) ABSTRACT

Disclosed herein is an engineered lipid-based vesicle optionally used for delivery of one or more payloads. The vesicle comprises a nanotube dimer or complex embedded with a lipid bilayer of the lipid-based vesicle. Also described herein are compositions, e.g., pharmaceutical compositions, and kits comprising the engineered lipid-based vesicle. In additional embodiments, further described herein are use of the engineered lipid-based vesicle for treating a disease or condition, for delivery to a target, or for labeling of a cell.

20 Claims, 31 Drawing Sheets

Related U.S. Application Data

(60) Provisional application No. 62/948,169, filed on Dec. 13, 2019.

(56) References Cited

U.S. PATENT DOCUMENTS

| | | | |
|---|---|---|---|
| 6,337,018 B1 | 1/2002 | Mickols | |
| 6,824,689 B2 | 11/2004 | Wang et al. | |
| 6,858,197 B1 | 2/2005 | Delzeit | |
| 6,863,942 B2 | 3/2005 | Ren et al. | |
| 7,205,069 B2 | 4/2007 | Smalley et al. | |
| 7,211,320 B1 | 5/2007 | Cooper et al. | |
| 7,229,556 B1 | 6/2007 | Hinds et al. | |
| 7,290,667 B1 | 11/2007 | Bakajin et al. | |
| 7,301,191 B1 | 11/2007 | Tombler et al. | |
| 7,413,723 B2 | 8/2008 | Niu et al. | |
| 7,419,601 B2 | 9/2008 | Cooper et al. | |
| 7,439,731 B2 | 10/2008 | Crafts et al. | |
| 7,459,121 B2 | 12/2008 | Liang et al. | |
| 7,473,411 B2 | 1/2009 | Ajayan et al. | |
| 7,572,426 B2 | 8/2009 | Strano et al. | |
| 7,611,628 B1 | 11/2009 | Hinds, III | |
| 7,623,340 B1 | 11/2009 | Song et al. | |
| 7,931,838 B2 | 4/2011 | Marand et al. | |
| 7,993,524 B2 | 8/2011 | Ratto et al. | |
| 8,029,856 B2 | 10/2011 | Miyoshi et al. | |
| 8,038,887 B2 | 10/2011 | Bakajin et al. | |
| 8,177,979 B2 | 5/2012 | Ratto et al. | |
| 8,196,756 B2 | 6/2012 | Ratto et al. | |
| 8,286,803 B2 | 10/2012 | Nowak et al. | |
| 8,541,322 B2 | 9/2013 | Barrera et al. | |
| 11,439,708 B2 | 9/2022 | Noy et al. | |
| 2003/0116503 A1 | 6/2003 | Wang et al. | |
| 2003/0121857 A1 | 7/2003 | Kurth et al. | |
| 2003/0165418 A1 | 9/2003 | Ajayan et al. | |
| 2004/0023372 A1 | 2/2004 | Klein et al. | |
| 2004/0173506 A1 | 9/2004 | Doktycz et al. | |
| 2005/0214356 A1* | 9/2005 | Joyce | A61K 9/127 514/19.3 |
| 2006/0073089 A1 | 4/2006 | Ajayan et al. | |
| 2006/0275371 A1 | 12/2006 | Dai et al. | |
| 2007/0137701 A1 | 6/2007 | Sainte Catherine et al. | |
| 2008/0149561 A1 | 6/2008 | Chu et al. | |
| 2008/0290020 A1 | 11/2008 | Marand et al. | |
| 2009/0321355 A1 | 12/2009 | Ratto et al. | |
| 2010/0025330 A1 | 2/2010 | Ratto et al. | |
| 2010/0069606 A1* | 3/2010 | Bangera | A61K 47/6901 977/734 |
| 2010/0206811 A1 | 8/2010 | Ng et al. | |
| 2011/0220574 A1 | 9/2011 | Bakajin et al. | |
| 2011/0229529 A1 | 9/2011 | Irvine et al. | |
| 2011/0253630 A1 | 10/2011 | Bakajin et al. | |
| 2012/0080378 A1 | 4/2012 | Revanur et al. | |
| 2012/0080380 A1 | 4/2012 | Wang et al. | |
| 2012/0241371 A1 | 9/2012 | Revanur et al. | |
| 2012/0261620 A1 | 10/2012 | Richter et al. | |
| 2012/0285890 A1 | 11/2012 | Koehler et al. | |
| 2017/0304447 A1* | 10/2017 | Noy | C01B 32/172 |
| 2019/0142761 A1 | 5/2019 | West | |
| 2022/0401558 A1 | 12/2022 | Noy et al. | |

FOREIGN PATENT DOCUMENTS

| | | |
|---|---|---|
| EP | 1 928 587 A2 | 6/2008 |
| GB | 2 399 092 A | 9/2004 |
| WO | WO-2005/001021 A2 | 1/2005 |
| WO | WO-2005/069750 A2 | 8/2005 |
| WO | WO-2007/025104 A2 | 3/2007 |
| WO | WO-2009/148959 A2 | 12/2009 |
| WO | WO-2016/057427 A1 | 4/2016 |
| WO | WO-2019/191444 A1 | 10/2019 |

OTHER PUBLICATIONS

Delin Sun, Thasin A. Peyear, W. F. Drew Bennett, Olaf S. Andersen, Felice C. Lightstone, and Helgi I. Ingolfsson. "Molecular Mechanism for Gramicidin Dimerization and Dissociation in Bilayers of Different Thickness." Biophysical Journal, vol. 117, Nov. 19, 2019, pp. 1831-1844. (Year: 2019).*

Garcia-Fandino, et al., "Designing biomimetic pores based on carbon nanotubes," PNAS, 19(18):6939-6944 (2012).

International Preliminary Report on Patentability on PCT PCT/US2020/064707 Dtd Jun. 23, 2022, 12 pages.

Notice of Allowance on U.S. Appl. No. 15/503,983 Dtd May 2, 2022, 9 pages.

Shimizu, et al., "Bcl-2 family proteins regulate the release of apoptogenic cytochrome c by the mitochondrial channel VDAC," Nature, vol. 399, pp. 483-487 (1999).

Acharya, M. et al., (2000) "Transport in Nanoporous Carbon Membranes: Experiments and Analysis," AIChe J. 45(5): 911-922.

Baudry, J. et al. (2001) "Experimental Evidence for a Large Slip Effect at a Nonwetting Fluid-Solid Interface," Langmuir 17: 5232-5236.

Beckstein, O. et al. (2004) "Not Ions Alone: Barriers to Ion Permeation in Nanopores and Channels," J Am Chem Soc. 126(45): 14694-14695.

Beckstein, O. et al., (2004) "The influence of geometry, surface character and flexibility on the permeation of ions and water through biological pores," Phys. Biol. 1: 42-52.

Berezhkovskii, A. et al. (2002) "Single-File Transport of Water Molecules through a Carbon Nanotube," Physical Review Letters 89(6): 064503-1-064503-4.

Bhatia, S.K. et al. (2005) "Comparisons of diffusive and viscous contributions to transport coefficients of light gases in single-walled carbon nanotubes," Molecular Simulation 31(9): 643-649.

Bird et al. (1960) "1.4 Theory of Viscosity of Gases at Low Density," Transport Phenomena Wiley, Ed. (New York), pp. 19-26.

Bittner, E.W. et al. (2003) "Characterization of the surfaces of single-walled carbon nanotubes using alcohols and hydrocarbons: a pulse adsorption technique," Carbon 41:1231-1239.

Buyukdagli, S. et al. Ionic Capillary Evaporation in Weakly Charged Nanopores. Phys. Rev. Lett. 105, 158103 (2010).

C. Lopez et al., "Understanding nature's design for a nanosyringe", PNAS, vol. 101, No. 13, Mar. 30, 2004, pp. 4431-4434.

Carter, D.J. et al. (2003) "Incorporation of Cyano Transition Metal Complexes in KCl Crystals—Experimental and Computational Studies," Aust. J. Chem. 56:675-678.

Cervera, J. et al. (2001) "Ion size effects on the current efficiency of narrow charged pores," J. Membrane Sci. 191:179-187.

Chakravarty, P. et al. (2008) "Thermal ablation of tumor cells with antibody-functionalized single-walled carbon nanotubes," PNAS 105(25):8697-8702.

Chen, H. et al. (2006) "Transport Diffusion of Gases is Rapid in Flexible Carbon Nanotubes," J. of Phys. Chem. B 110:1971-1975.

Chen, H. et al.(2006) "Predictions of selectivity and flux for CH4/H2 separations using single walled carbon nanotubes as membranes," J. Memb. Sci. 269:152-160.

Chernomordik, L. V. & Kozlov, M. M., "Mechanics of membrane fusion", Natural Structural Molecular Biology, 15(7), Jul. 2008, pp. 675-683.

Childress, A.E., et al., "Relating Nanofiltration Membrane Performance to Membrane Charge (Electrokinetic) Characteristics," 2000, Environ. Sci. Technol., vol. 34, No. 17, pp. 3710-3716.

Chopra, N. et al. (2005) "Bifunctional carbon nanotubes by side wall protection," Adv. Funct. Mater. 15(5):858-864.

Cooper, S.M. et al. (2004) "Gas Transport Characteristics through a Carbon Nanotube," Nano Lett. 4(2):377-381.

Cottin-Bizonne, C. et al. (2002)" Nanorheology: An investigation of the boundary condition at hydrophobic and hydrophilic interfaces," Eur. Phys. J. E 9:47-53.

Craig, V.S.J. et al. (2001) "Shear-Dependent Boundary Slip in an Aqueous Newtonian Liquid," Phys. Rev. Let. 87(5):054504-1-054504-4.

Cui, H. et al. (2000) "Deposition of aligned bamboo-like carbon nanotubes via microwave plasma enhanced chemical vapor deposition," J. Appl. Phys. 88(10):6072-6074.

(56) References Cited

OTHER PUBLICATIONS

De Lint, W., et al., "Predictive charge-regulation transport model for nanofiltration from the theory of irreversible processes," 2004, J. Membrane Sci., vol. 243, pp. 365-377.
Dechadilok, P. et al. (2006) "Hindrance factors for diffusion and convection in pores," Ind. Eng. Chem. Res. 45:6953-6959.
Deen, W.M. (1987) "Hindered transport of large molecules in liquid-filled pores," AIChE 33(9):1409-1425.
Donnan, F.G. (1924) The theory of membrane equilibria, Chem Rev 1 :73-90.
Donnan, F.G. (1995) "Theory of membrane equilibria and membrane potentials in the presence of non-dialysing electrolytes—A contribution to physical-chemical physiology," Journal of Membrane Science 100(1 ):45-55. (Reprinted from Zeitshrift fur Electrochemie und Angewandte Physikalische Chemie (1911) 17: 572).
Doyle, D.A. et al. (1998)"The Structure of the Potassium Channel: Molecular Basis of K Conduction and Selectivity," Science 280(5360): 69-77.
Dutt, M.J. et al. Interactions of End-functionalized Nanotubes with Lipid Vesicles: Spontaneous Insertion and Nanotube Self-Organization. Curr. Nanosci. 7, 699-715 (2011).
Epand, R. M., "Fusion peptides and the mechanism of viral fusion", Biochimica et Biophysica Acta, 1614,(2003, pp. 116-121.
Fernandez et al., "Adaptive and Mutational Resistance: Role of Porins and Efflux Pumps in Drug Resistance", Clinical Microbiology Reviews, Oct. 2012, vol. 25, No. 4, pp. 661-681.
Final Office Action on U.S. Appl. No. 15/503,983 Dtd Aug. 6, 2019.
Final Office Action on U.S. Appl. No. 15/503,983 Dtd Sep. 24, 2020.
Fornasiero et al., "Ion exclusion by sub-2-nm carbon nanotube pores", PNAS, Nov. 11, 2008, vol. 105, No. 45, pp. 17250-17255.
Fornasiero, F et al. Ion Exclusion by sub-2-nm Carbon Nanotube Pores. Proc. Natl. Acad. Sci. USA 105, 17250-17255 (2008).
Fornasiero, F. et al., "ph-tunable Ion Selectivity in Carbon Nanotube Pores", Langmuir (2010, 26(18), pp. 14848-14853.
Forterre, P., "The origin of viruses and their possible roles in major evolutionary transitions", Virus Research, 117 (2006), pp. 5-16.
Frolov, V.A. et al. Shape bistability of a membrane neck: a toggle switch to control vesicle content release. Proc. Natl. Acad. Sci. 100, 8698-8703 (2003).
Gao, H. et al. (2003) "Spontaneous Insertion of DNA Oligonucleotides into Carbon Nanotubes," Nano Letters 3(4):471-473.
Geng, J. et al., "Stochastic transport through carbon nanotubes in lipid bilayers and live cell membranes", Nature, vol. 514, Oct. 30, 2014, pp. 612-615.
Gu, L.-Q. & Bayley, H. Interaction of the Noncovalent Molecular Adapter β-Cyclodextrin, with the Staphylococcal a-Hemolysin Pore. Biophys. J 79, 1967-1975 (2000).
Hall, A.R. et al. Hybrid pore formation by directed insertion of a-haemolysin into solid-state nanopores. Nat. Nanotechnol. 5, 874-877 (2010).
Haque, F. et al. Incorporation of a viral DNA-packaging motor channel in lipid bilayers for real-time, single-molecule sensing of chemicals and double-stranded DNA. Nat. Protoc. 8, 373-392 (2013).
Harrell, C.C. et al. (2003) "Synthetic Single-Nanopore and Nanotube Membranes," Anal. Chem. 75:6861-6867.
Harrison, S. C., "Viral membrane fusion", Nature Structural & Molecular Biology, vol. 15, No. 7, Jul. 2008, 690-698.
Hata, K. et al. (2004) Water-Assisted Highly Efficient Synthesis of Impurity-Free Single-Walled Carbon Nanotubes, Science 306:1362-1364.
Hinds, B.J., et al., "Aligned Multiwalled Carbon Nanotube Membranes ," Jan. 2, 2004, Science, vol. 303, No. 5654, pp. 62-65.
Holt et al., "Fabrication of a Carbon Nanotube-Embedded Silicon Nitride Membrane for Studies of Nanometer-Scale Mass Transport", Nano Letters, vol. 4, No. 11 2004, pp. 2245-2250.
Holt, J.K., et al., "Fast Mass Transport Through Sub-2-Nanometer Carbon Nanotubes," May 19, 2006, Science, vol. 312, No. 5776, pp. 1034-1037.
Hou, H. et al. (2002) "Poly(p-xylylene) Nanotubes by Coating and Removal of Ultrathin Polymer Template Fibers," Macromolecules 35:2429-2431.
Hummer, G. (2007) "Water, proton, and ion transport: from nanotubes to proteins," Molecular Physic 105(2):201-207.
Hummer, G. et al. (2001) "Water conduction through the hydrophobic channel of a carbon nanotube," Nature 414(6860):188-190.
Hummer, G. et al. Water conduction through the hydrophobic channel of a carbon nanotube. Nature 414, 188-190 (2001).
Iijima, S. et al. (1996) "Structural flexibility of carbon nanotubes," J. Chem. Phys. 104(5):2089-2092.
International Preliminary Report on Patentability (IPEA/KR) in International Application No. PCT/US2015/054084, mailed Jan. 24, 2017.
International Search Report and Written Opinion (ISA/KR) in International Application No. PCT/US2015/054084, mailed Dec. 21, 2015.
Itaya, K. et al. (1984) "Properties of Porous Anodic Aluminum Oxide Films as Membranes," J. Chem. Eng. Jpn. 17(5):514-520.
Joseph, S. et al. (2003) "Electrolytic Transport in Modified Carbon Nanotubes," Nano Letters 3(10):1399-1403.
Kalra, A. et al. (2003) "Osmotic water transport through carbon nanotube membranes," Proc Natl Acad Sci USA 100(18):10175-10180.
Kam, N.W.S. et al. Carbon nanotubes as multifunctional biological transporters and near-infrared agents for selective cancer cell destruction. Proc. Natl. Acad. Sci. USA 102, 11600-11605 (2005).
Kasianowicz, J.J. et al. Characterization of individual polynucleotide molecules using a membrane channel. Proc. Natl. Acad. Sci. USA 93, 13770-13773 (1996).
Kneidl, B., Peller, M., Winter, G., Lindner, L. H. & Hossann, M., "Thermosensitive liposomal drug delivery systems: state of the art review", International Journal Nanomedicine, 9, 2014, pp. 4387-4398.
Koga, K. "Formation of ordered ice nanotubes inside carbon nanotubes," Aug. 23, 2001, Nature, vol. 412, pp. 802-805.
Kolesnikov, A., et al., "Anomalously Soft Dynamics of Water in a Nanotube: A Revelation of Nanoscale Confinement," 2004, Phys. Rev. Lett., vol. 93, pp. 035503-1-035503-4.
Kotsalis, E.M. et al. (2004) "Multiphase water flow inside carbon nanotubes," Int. J. Multiphase Flow 30:995-1010.
Kushwaha et al., "Carbon nanotubes as a novel drug delivery system for anticancer therapy: a review", Brazilian Journal of Pharmaceutical Sciences, 2013, vol. 49, No. 4, 15 pages.
L. Liu et al., "Ultrashort single-walled carbon nanotubes in a lipid bilayer as a new nanopore sensor", Nature Communications 4, 1-8 (2013).
Lacerda, L. et al. How do functionalized carbon nanotubes land on, bind to and pierce through model and plasma membranes. Nanoscale 5, 10242-10250 (2013).
Langecker, M. et al. Synthetic Lipid Membrane Channels Formed by Designed DNA Nanostructures. Science 338, 932-936 (2012).
Le Duc, Y. et al. Imidazole-Quartet Water and Proton Dipolar Channels. Angew. Chem. Int. Ed. SO, 11366-11372 (2011).
Lee, C.Y. et al. Coherence Resonance in a Single-Walled Carbon Nanotube Ion Channel. Science 329, 1320-1324 (2010).
Leung, K. et al. (2006) "Salt Permeation and Exclusion in Hydroxylated and Functionalized Silica Pores," Phys. Rev. Lett. 96(9):4.
Lev, A. et al. Rapid switching of ion current in narrow pores: implications for biological ion channels. Proc. Roy. Soc. B 252, 187-192 (1993).
Li, J. et al. (1999) "Highly-ordered carbon nanotube arrays for electronics applications," Appl. Phys Lett. 75(3):367-369.
Li, J. et al. Ion-beam sculpting at nanometre length scales. Nature 412, 166-169 (2001).
Li, P.H. et al. (2007) "Tailoring Wettability Change on Aligned and Patterned Carbon Nanotube Films for Selective Assembly," J Phys Chem B. 111(7):1672-1678.

(56) References Cited

OTHER PUBLICATIONS

Liu et al., "Carbon Nanotube Based Artificial Water Channel Protein: Membrane Perturbation and Water Transportation", Nano Letters, 2009, vol. 9, No. 4, pp. 1386-1394.
Liu et al., "Ultrashort single-walled carbon nanotubes in a lipid bilayer as a new nanopore sensor", Nature Communications, Oct. 11, 2013, pp. 1-8.
Liu, H. et al. (2006) "Ion permeation dynamics in carbon nanotubes," J. Chem. Phys. 125:084713-1-084713-14.
Liu, H. et al. Translocation of Single-Stranded DNA Through Single-Walled Carbon Nanotubes. Science 327, 64-67 (2010).
Liu, Z. et al. (2009) "Preparation of carbon nanotube bioconjugates for biomedical applications," Nature Protocols 4(9):1372-1383.
Lopez et al., "Understanding nature's design for a nanosyringe", PNAS, Mar. 30, 2004, vol. 101, No. 13, pp. 4431-4434.
Ma, R.Z. et al. (1998) "Processing and properties of carbon nanotubes-nano-SiC ceramic," J. Mater. Sci. 33:5243-5246.
Majumder, M. et al. (2005) "Effect of Tip Functionalization on Transport through Vertically Oriented Carbon Nanotube Membranes," J Am Chem Soc. 127(25): 9062-9070.
Majumder, M. et al. (2005) "Nanoscale hydrodynamics: Enhanced flow in carbon nanotubes," Nature 438(7064 ): 44.
Majumder, M. et al. (2007) "Voltage gated carbon nanotube membranes," Langmuir 23(16): 8624-8631.
Melechko et al., "Vertically aligned carbon nanofibers and related structures: Controlled synthesis and directed assembly", Applied Physics Reviews, vol. 97, Feb. 3, 2005.
Miller et al., "Electoosmotic Flow in Template-prepared Carbon Nanotube Membranes", J. Am. Chem. Soc. 123:12335-12342 (2004).
Miyazawa, A., et al., "Structure and gating mechanism of the acetylcholine receptor pore," Jun. 26, 2003, Nature, vol. 423, pp. 949-955.
Murakami, Y. et al. (2004) "Growth of vertically aligned single-walled carbon nanotube films on quartz substrates and their optical anisotropy," Chem. Phys. Lett. 385:298-303.
Nagai, Y. et al. (2006) "Slow release of molecules in self assembling peptide nanofiber scaffold," Journal of Controlled Release 115(1):18-25.
Naguib, N. et al.(2004) "Observation of Water Confined in Nanometer Channels of Closed Carbon Nanotubes," Nano Lett. 4(11):2237-2243.
Ned Noor, P. et al. (2005) "Reversible Biochemical Switching of Ionic Transport through Aligned Carbon Nanotube Membranes," J. Chem. Mater. 17:3595-3599.
Ned Noor, P. et al. (2007) "Carbon nanotube based biomimetic membranes: mimicking protein channels regulated by phosphorylation," J. Mater. Chem. 17:1755-1757.
Neher, E. et al. Ionic selectivity, saturation, and block in gramicidin A channels. J Membr. Biol. 40, 97-116 (1978).
Nestorovich, E.M. et al. Residue ionization and ion transport through OmpF channels. Biophys. J 85, 3718-3729 (2003).
Nga No, "Virus-Like Membrane Fusion and Drug Delivery with Carbon Nanotube Porins", Lawrence Livermore National Laboratory, Dec. 19, 2019, 15 pages.
Nightingale, E.R. (1959) "Phenomenological theory of ion salvation—Effective radii of hydrated ions," Journal of Physical Chemistry 63(9):1381-1387.
Non-Final Office Action on U.S. Appl. No. 15/503,983 Dtd Mar. 19, 2020.
Park, J.H. et al. (2006) "Ion separation using a Y-junction carbon nanotube," Nanotechnology 17:895-900.
Peter, C. et al. (2005) "Ion Transport through Membrane-Spanning Nanopores Studied by Molecular Dynamics Simulations and Continuum Electrostatics Calculations," Biophys 89(4): 2222-2234.
Powell, M.R. et al. Electric-field-induced wetting and dewetting in single hydrophobic nanopores. Nat. Nanotechnol. 6, 798-802 (2011).
Powell, M.R. et al. Nanoprecipitation-assisted ion current oscillations. Nat. Nanotechnol. 3, 51-57 (2007).
Rousseau, R. et al. (2004) "Modeling protonated water networks in bacteriorhodopsin," Phys. Chem. Chem. Phys. 6:1848-1859.

S. Wang et al., "Precise cutting of single-walled carbon nanotubes", Nanotechnology 18, Jan. 9, 2007, pp. 1-6.
Sakamoto, Y. et al. (2007) "Preparation and CO2 separation properties of amine-modified mesoporous silica membranes," Microporous and Mesoporous Materials 101 (1-2):303-311.
Schaep, J. et al. (1998) "Influence of ion size and charge in nanofiltration," Separation and Purification Technology 14(1-3):155-162.
Schaep, J. et al. (2001) "Modelling the retention of ionic components for different nanofiltration membranes," Separation and Purification Technology 22-23:169-179.
Shimizu, S. et al. Stochastic Pore Blocking and Gating in PDMS-Glass Nanopores from Vapor-Liquid Phase Transitions. J Phys. Chem. C 117, 9641-9651 (2013).
Shnyrova, A.V. et al. Geometric catalysis of membrane fission driven by flexible dynamin rings. Science 339, 1433-1436 (2013).
Sun, L. et al. (2000) "Single Carbon Nanotube Membranes: A Well-Defined Model for Studying Mass Transport through Nanoporous Materials," J. Am. Chem. Soc. 122:12340-12345.
Sun, X. et al. Optical Properties of Ultrashort Semiconducting Single-Walled Carbon Nanotube Capsules Down to Sub-10 nm. J Am. Chem. Soc. 130, 6551-6555 (2008).
US Office Action on U.S. Appl. No. 15/503,983 Dtd Jan. 10, 2019.
US Office Action on U.S. Appl. No. 15/503,983 Dtd Mar. 19, 2020.
Venkatesan, B.M. & Bashir, R. Nanopore sensors for nucleic acid analysis. Nat. Nanotechnol. 6, 615-624 (2011).
Wallace, E.J. et al. (2009) "Carbon nanotube self-assembly with lipids and detergent: a molecular dynamics study," Nanotechnology 20:045101, 1-6.
Walther, J.H. et al. Barriers to Superfast Water Transport in Carbon Nanotube Membranes. Nano Lett. 13, 1910-1914 (2013).
Wong, S.S. et al. (1998) "Covalently Functionalized Nanotubes as Nanometer-Sized Probes in Chemistry and Biology," Nature 394:52-55.
Wong, S.S. et al. (1998) "Covalently-Functionalized Single-Walled Carbon Nanotube Probe Tips for Chemical Force Microscopy," J. Am. Chem. Soc. 120:8557-8558.
Yang, D.Q. et al. (2005) "Controlled chemical functionalization of multiwalled carbon nanotubes by kiloelectronvolt argon ion treatment and air exposure," Langmuir. 21 (18):8539-8545.
Zimmerli, U. & Koumoutsakos, P. Simulations of Electrophoretic RNA Transport Through Transmembrane Carbon Nanotubes. Biophys. J 94, 2546-2557 (2008).
Bhaskara et al., "Carbon Nanotubes Mediate Fusion of Lipid Vesicles," ACS Nano, Jan. 24, 2017 (Jan. 24, 2017), vol. 11, No. 2, pp. 1273-1280.
Final Office Action on U.S. Appl. No. 15/503,983 Dtd Dec. 9, 2021, 9 pages.
International Search Report and Written Opinion issued in PCT Application No. PCT/US2020/064707 Dtd Mar. 26, 2021, 17 pages.
Non-Final Office Action on U.S. Appl. No. 15/503,983 Dtd May 26, 2021, 14 pages.
Examination Report issued in Singapore Patent Application No. 200801264-3 Dtd Apr. 7, 2011, 7 pages.
International Search Report and Written Opinion received on PCT/US2009/045675, Dtd Jan. 15, 2010, 14 pages.
Substantive Examination Report and Search Report issued in Malaysian Application No. PI20064008 Dtd Nov. 30, 2009, 3 pages.
US Final Office Action on U.S. Appl. No. 12/995,160 Dtd Sep. 6, 2013, 6 pages.
US Notice of Allowance on U.S. Appl. No. 12/995,160 Dtd Sep. 26, 2014, 7 pages.
US Office Action on U.S. Appl. No. 10/613,960, dated Jun. 5, 2006, 10 pages.
US Office Action on U.S. Appl. No. 12/064,604 Dtd Jun. 29, 2010, 11 pages.
US Office Action on U.S. Appl. No. 12/955,843 Dtd Mar. 5, 2013, 7 pages.
US Office Action on U.S. Appl. No. 12/995,160 Dtd Feb. 14, 2013, 11 pages.
US Office Action on U.S. Appl. No. 12/995,160 Dtd Jun. 26, 2014, 8 pages.

(56) References Cited

OTHER PUBLICATIONS

Abraham, M.J., et al., GROMACS: High performance molecular simulations through multi-level parallelism from laptops to supercomputers. SoftwareX 1-2, pp. 19-25 (2015).
Alidori S., et al., "Carbon nanotubes exhibit fibrillar pharmacology in primates.", PloS One 12, e0183902 (2017).
Allen, T. M., et al., "Liposomal drug delivery systems: From concept to clinical applications." Adv. Drug Deliv. Rev. 65, pp. 36-48 (2013).
Barenholz, Y.C., "Doxil—The first FDA-approved nano-drug: Lessons learned.", J. Contr. Release 160, pp. 117-134 (2012).
Bhaskara, R. M. et al., "Carbon nanotubes mediate fusion of lipid vesicles.", ACS Nano 11, pp. 1273-1280 (2017).
Bussi, G., et al., "Canonical sampling through velocity rescaling." J. Chem. Phys. 126, 014101 (2007).
Zylberberg, C., et al., "Pharmaceutical liposomal drug delivery: A review of new delivery systems and a look at the regulatory landscape.", Drug Deliv. 23, pp. 3319-3329 (2016).
Chabner, B.A., et al., "Chemotherapy and the war on cancer.", Nat. Rev. Canc. 5 (1), pp. 65-72 (2005).
Peer, D. et al., "Nanocarriers as an emerging platform for cancer therapy.", Nat. Nanotechnol. 2, pp. 751-760 (2007).
De Jong, D.H., et al., "Martini straight: Boosting performance using a shorter cutoff and GPUs." Comput. Phys. Commun. 199, pp. 1-7 (2016).
Earp, L.J., et al., "The many mechanisms of viral membrane fusion proteins" Membrane Trafficking in Viral Replication, M. Marsh, Ed. (Springer) pp. 25-66 (2004).
Epand, R.M., "Fusion peptides and the mechanism of viral fusion.", Biochim. Biophys. Acta Biomembr. 1614, pp. 116-121 (2003).
Filion, M.C., et al., "Major limitations in the use of cationic liposomes for DNA delivery.", Int. J. Pharm. 162, pp. 159-170 (1998).
Focke, W.W., et al., "Kinetic interpretation of log-logistic dose-time response curves." Sci. Rep. 7, pp. 1-11 (2017).
Fornasiero, F. et al., "PH-tunable ion selectivity in carbon nanotube pores.", Langmuir, 26, pp. 14848-14853 (2010).
François-Martin, C. et al., "Low energy cost for optimal speed and control of membrane fusion." Proc. Natl. Acad. Sci. U.S.A. 114, pp. 1238-1241 (2017).
Galassi, T.V., et al., "Long-term in vivo biocompatibility of single walled carbon nanotubes.", PloS One 15, e0226791 (2020).
Geng, J. et al., "Stochastic transport through carbon nanotubes in lipid bilayers and live cell membranes." Nature 514, pp. 612-615 (2014).
Harrison, S.C., "Viral membrane fusion.", Nat. Struct. Mol. Biol. 15, p. 690 (2008).
Hernandez, J.M., et al., "Variable cooperativity in snare-mediated membrane fusion." Proc. Natl. Acad. Sci. U.S.A. 111, pp. 12037-12042 (2014).
Ho, N.T., et al., "Membrane fusion and drug delivery with carbon nanotube porins" PNAS vol. 118 No. 19 e2016974118, pp. 1-8 (2021).
Kielian, M. et al., "Virus membrane-fusion proteins: More than one way to make a haripin.", Nat. Rev. Microbiol. 4, pp. 67-76 (2005).

Knudsen, K.B., et al., "In vivo toxicity of cationic micelles and liposomes." Nanomedicine 11, pp. 467-477 (2015).
Kowalski, P.S., et al., "Delivering the messenger: Advances in technologies for therapeutic mrna delivery.", Mol. Ther. 27, p. 710 (2019).
Marrink, S.J., et al., The MARTINI force field: Coarse grained model for biomolecular simulations. J. Phys. Chem. B 111, pp. 7812-7824 (2007).
Ong, S.G.M., et al., Influence of the encapsulation efficiency and size of liposome on the oral bioavailability of griseofulvin-loaded liposomes., Pharmaceutics 8 p. 25 (2016).
Parrinello, M., et al., "Polymorphic transitions in single crystals: A new molecular dynamics method." J. Appl. Phys. 52, pp. 7182-7190 (1981).
Rawson, F. J.,et al., "Electron transfer from proteus vulgaris to a covalently assembled, single walled carbon nanotube electrode functionalised with osmium bipyridine complex: Application to a whole cell biosensor." Biosens. Bioelectron. 26, pp. 2383-2389 (2011).
Ruggiero, A., et al., "Paradoxical glomerular filtration of carbon nanotubes.", Proc. Natl. Acad. Sci. U.S.A. 107, pp. 12369-12374 (2010).
Russell, L.M., et al., "Leakage kinetics of the liposomal chemotherapeutic agent doxil: The role of dissolution, protonation, and passive transport, and implications for mechanism of action.", J. Contr. Release 269, pp. 171-176 (2018).
Sercombe L., et al., "Advances and challenges of liposome assisted drug delivery.", Front. Pharmacol. 6, 286, pp. 1-13 (2015).
Seynhaeve, A.L.B., et al., "Intact doxil is taken up intracellularly and released doxorubicin sequesters in the lysosome: Evaluated by in vitro/in vivo live cell imaging.", J. Contr. Release 172, pp. 330-340 (2013).
Soundararajan, A., et al., "Re-liposomal doxorubicin (Doxil): In vitro stability, pharmacokinetics, imaging and biodistribution in a head and neck squamous cell carcinoma xenograft model.", Nucl. Med. Biol. 36, pp. 515-524 (2009).
Struck, D. K. et al., "Use of resonance energy transfer to monitor membrane fusion." Biochemistry 20, pp. 4093-4099 (1981).
Timko B.P., et al., "Advances in drug delivery.", Annu. Rev. Mater. Res. 41, pp. 1-20 (2011).
Tojima, T., et al., "Acquisition of neuronal proteins during differentiation of NG108-15 cells." Neurosci. Res. 37, pp. 153-161 (2000).
Tunuguntla, R.H., et al., "Ultrafast proton transport in sub-1-nm diameter carbon nanotube porins.", Nat. Nanotechnol. 11, pp. 639-644 (2016).
Tunuguntla, R.H., et al., "Synthesis, lipid membrane incorporation, and ion permeability testing of carbon nanotube porins." Nat. Protoc. 11, p. 2029 (2016).
Vögele, M., et al., "Divergent diffusion coefficients in simulations of fluids and lipid membranes." J. Phys. Chem. B 120, pp. 8722-8732 (2016).
Weber, T. et al., "SNAREpins: Minimal machinery for membrane fusion." Cell 92, pp. 759-772 (1998).
Yang, J. et al., "Drug delivery via cell membrane fusion using lipopeptide modified liposomes.", ACS Cent. Sci. 2, pp. 621-630 (2016).

\* cited by examiner

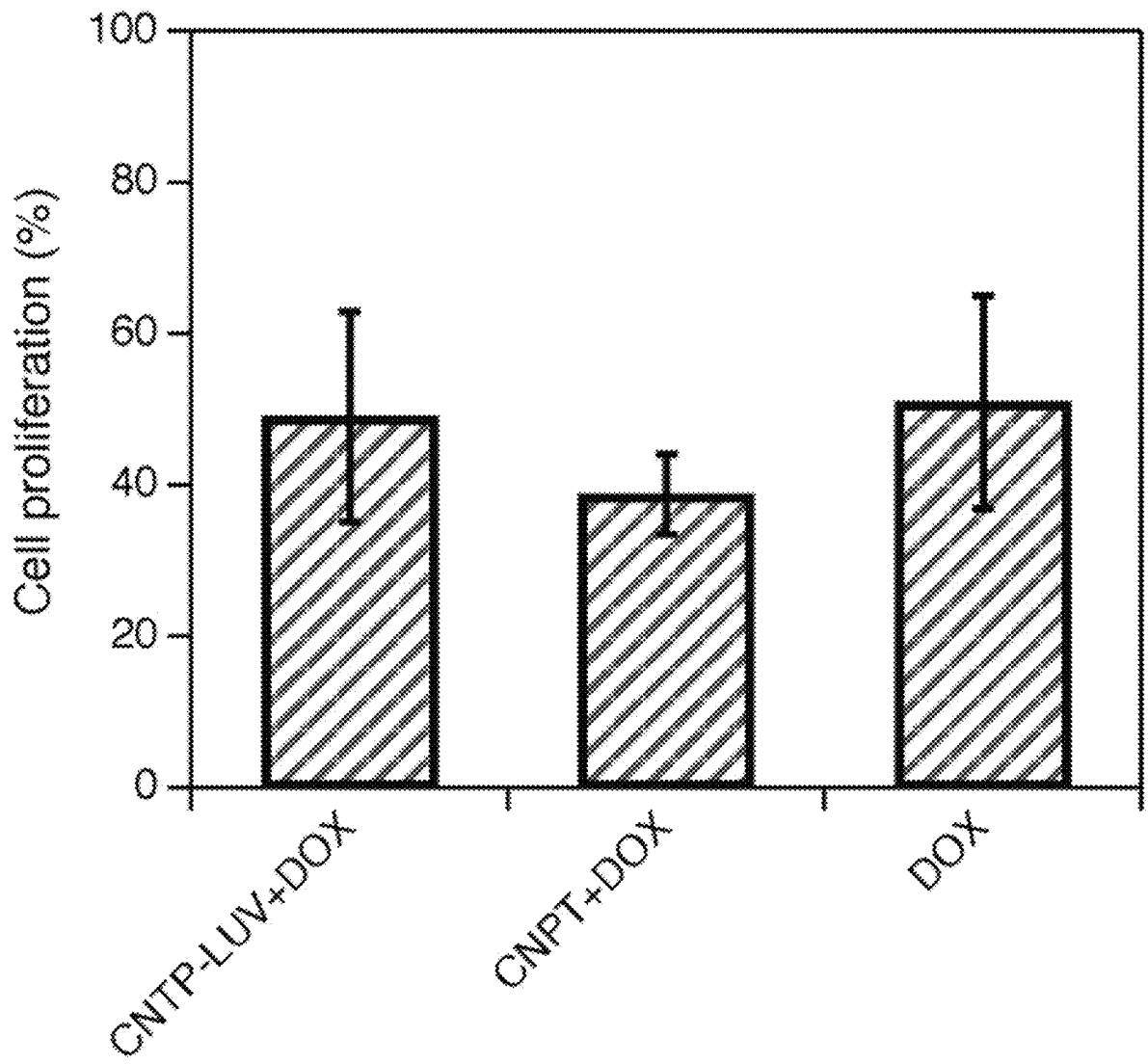

CNTP-LUV      Free CNTP      PBS

DOX encapsulated CNTP-LUV      DOX-LUV      20 µg/ml DOX

NANOTUBE-VESICLE COMPOSITIONS AND USES THEREOF

CROSS-REFERENCE TO RELATED APPLICATION

This application is a continuation application filed under 35 U.S.C. § 111(a) claiming the benefit under 35 U.S.C. § 120 and 365(c) of International Patent Application No. PCT/US2020/064707, filed on Dec. 11, 2020, which is based upon and claims priority under 35 U.S.C. § 119(e) to U.S. Provisional Patent Application No. 62/948,169, filed Dec. 13, 2019, the contents of each of which are hereby incorporated by reference into the present disclosure.

STATEMENT OF GOVERNMENT SUPPORT

The United States Government has rights in this invention pursuant to Contract No. DE-AC52-07NA27344 between the United States Department of Energy and Lawrence Livermore National Security, LLC for the operation of Lawrence Livermore National Laboratory. The United States Government has rights in this invention further pursuant to SCW0972-17 awarded by the U.S. Department of Energy and 1710211 awarded by the National Science Foundation.

BACKGROUND OF THE DISCLOSURE

Cancer along with heart diseases and cerebrovascular diseases rank as the top three killers of the modern society. Drugs such as chemotherapeutic agents are associated with severe, and sometimes fatal, toxicity. Although different delivery systems have been developed to combat toxicity; however, challenges remain including optimizing the biocompatibility and acceptability with the human body. This disclosure addresses this issue and provides related advantages as well.

SUMMARY OF THE DISCLOSURE

Disclosed herein, in certain embodiments, is an engineered lipid-based vesicle for delivery of one or more payloads. In some embodiments, the engineered lipid-based vesicle comprises a nanotube complex (e.g., a nanotube dimer) embedded within the lipid bilayer circumference of a lipid-based vesicle. In some embodiments, the engineered lipid-based vesicle comprises a carbon nanotube (e.g., a single-walled carbon nanotube) complex or dimer or a boron nitride nanotube complex or dimer. In some embodiments, also described herein are compositions, e.g., pharmaceutical compositions, and kits comprising the engineered lipid-based vesicle. In additional embodiments, further described herein are use of the engineered lipid-based vesicle for treating a disease or condition, for delivery to a target, or for labeling of a cell.

Disclosed herein, in certain embodiments, is an engineered lipid-based vesicle comprising a nanotube complex (e.g., a nanotube dimer) embedded within the lipid bilayer circumference of the lipid-based vesicle. In some embodiments, the nanotube complex (e.g., a nanotube dimer) comprises, or consists essentially of, or consists of, a carbon nanotube complex, a boron nitride nanotube (BNNT) complex, a $MoS_2$ nanotube complex, a $MoS_2$-carbon nanotube hybrid complex, or a carbon-$MoS_2$—$WS_2$ nanotube hybrid complex, wherein the complex facilitates fusion of the lipid-based vesicle to a target cell or target vesicle. In some embodiments, the nanotube complex comprises, or consists essentially of, or consists of, a carbon nanotube complex. In some embodiments, the carbon nanotube complex is a single-walled carbon nanotube (SWCNT) complex. In some embodiments, the SWCNT complex comprises, or consists essentially of, or consists of, a conjugated SWCNT complex.

Disclosed herein, in certain embodiments, is a composition comprising, or consisting essentially of, or consisting of, an engineered lipid-based vesicle described herein, and an excipient. In some embodiments, the excipient is a pharmaceutically acceptable excipient.

Disclosed herein, in certain embodiments, is a method of treating a disease or condition in a subject in need thereof, comprising: administering to the subject an engineered lipid-based vesicle described herein or a composition described herein.

Disclosed herein, in certain embodiments, is a method of delivering a payload to a target, comprising: contacting an engineered lipid-based vesicle described herein or a composition described herein to the target, thereby delivering the payload to the target.

Disclosed herein, in certain embodiments, is a method of detectably labeling a cell, comprising: contacting the cell with an engineered lipid-based vesicle described herein or a composition described herein; and visualizing the cell.

Disclosed herein, in certain embodiments, is a kit comprising an engineered lipid-based vesicle described herein or a composition described herein, optionally further comprising a set of instructions.

Disclosed herein, in certain embodiments, is an engineered lipid-based vesicle comprising a SWCNT dimer embedded within the lipid bilayer circumference of the lipid-based vesicle, optionally the lipid-based vesicle comprises of, consisting essentially of, or consisting of DOPC, cholesterol, or PEG-lipids. In some instances, also disclosed is a composition comprising the engineered lipid-based vesicle. In additional instances, disclosed herein is a method of treating a disease or condition utilizing the engineered lipid-based vesicle, method of delivering a payload to a target by utilizing the engineered lipid-based vesicle, or method of detectably labeling a cell by utilizing the engineered lipid-based vesicle.

Disclosed herein, in certain embodiments, is an engineered lipid-based vesicle comprising a BNNT dimer embedded within the lipid bilayer circumference of the lipid-based vesicle, optionally the lipid-based vesicle comprises of, consisting essentially of, or consisting of DOPC, cholesterol, or PEG-lipids. In some instances, also disclosed is a composition comprising the engineered lipid-based vesicle. In additional instances, disclosed herein is a method of treating a disease or condition utilizing the engineered lipid-based vesicle, method of delivering a payload to a target by utilizing the engineered lipid-based vesicle, method of detectably labeling a cell by utilizing the engineered lipid-based vesicle, or vaccine delivery.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A illustrates a schematics of the vesicle fusion assay. CNTP-LUVs fuse to the vesicles containing DOPC lipid labeled with NBD dye in self-quenching concentration, de-quench the dye, and increases its fluorescence signal. FIG. 1B shows kinetics of the vesicle fusion recorded as NBD-LUVs were mixed with CNTP-LUVs with different average number of CNTPs per vesicle (as indicated on the graph). Solid lines represent best fits to the Hill equation. FIG. 1C shows activation energy, $E_a$ for vesicle fusion plotted as a function of pH. An inset shows a representative Arrhenius plot used to obtain the $E_a$ values. (n=3). FIG. 1D shows a plot of the fusion half time as a function of the average number of CNTPs per vesicle (N=3 for 10, 20, and 30 CNTP/LUV and N=2 for 5 CNTP/LUV). Lines represent fits to the first (dash-dotted black line) and second (blue dashed line) order kinetics. FIG. 1E shows a content-mixing assay showing fluorescence signal kinetics recorded as CNTP-LUVs were exposed to LUVs encapsulating SRB dye (N=2) in presence and in absence of an anti-SRB quenching antibody.

FIG. 2A shows snapshots of simulated systems of a CNTP monomer, dimer and trimer ($\Delta N$=632). Inner leaflet phosphate groups are drawn larger for clarity. FIG. 2B shows cumulative number of CNTP-mediated vesicle fusion events as a function of time at different number asymmetries $\Delta N$. Monomer, dimer, and trimer simulations are compared. A total of 30 simulations were performed for each starting configuration (indicated as black dashed line). Simulations were 1.7 µs long. FIG. 2C shows minimal distance of C5A/B tail beads of the opposing inner leaflet lipids at $\Delta N$=632. Exemplary trace shown for monomer, dimer, and trimer respectively. All traces for all systems are shown in FIG. 5. The dashed line at 8 Å indicates contact of the opposing leaflets. FIG. 2D shows zoom-in on CNTP dimer mediated fusion. Time points of snapshots are indicated. Lipids with particles within 8 Å of the CNTP are shown. Inner leaflet lipids drawn thicker for clarity. Outer leaflet phosphate groups are omitted for clarity.

FIG. 3A shows schematic showing CNTP-LUV loaded with the DOX payload fusing to a cancer cell and delivering DOX to the cell interior. FIG. 3B shows cell survival (live/dead) assay results after 48-hr exposure of neuroblastoma-glioma (NG-108-15) and human breast cancer (MDA) cell cultures to DOX-CNTP-LUVs, CNTP-LUVs, free CNTPs, DOX-LUVs, free DOX, and PBS buffer. (n=3, with 3 replicate wells per each experiment). FIG. 3C shows results of MTT cell proliferation assay after 48-hr exposure of mice neuroblastoma and rat-glioma (NG-108-15) and human breast cancer (MDA-MB-231) cell cultures to DOX-CNTP-LUVs, CNTP-LUVs, free CNTPs, DOX-LUVs, free DOX, and PBS buffer. (n=3, with 3 replicate wells per each experiment). FIG. 3D shows fluorescence microscopy images of NG108-15 cell culture with live and dead cells stained with green and red dye, respectively. Prior to imaging the cells were exposed for 48 hrs to (i) PBS buffer; (ii) CNTP-LUVs without the drug payload; (iii) CNTP solution; (iv) LUVs encapsulating DOX; (v) 20 µg/ml of DOX; (vi) CNTP-LUVs with encapsulated DOX. FIG. 3E shows fluorescence microscopy images of MDA-MB-231 cell culture with stained live and dead cells. Prior to imaging the cells were exposed for 48 hrs to (i) PBS buffer; (ii) CNTP-LUVs without the drug payload; (iii) CNTP solution; (iv) LUVs encapsulating DOX; (v) 20 µg/ml of DOX; (vi) CNTP-LUVs with encapsulated DOX.

FIG. 8A shows fusion assay kinetics recorded after mixing CNTP-LUVs made with 100% DOPC and 70% DOPC: 30% cholesterol with NBD-LUVs (see Methods for details). The control experiment used LUVs made with 100% DOPC. FIG. 8B shows a content-mixing assay showing fluorescence signal kinetics recorded as CNTP-LUVs made with 70% DOPC:30% cholesterol were exposed to LUVs encapsulating SRB dye in presence and in absence of an anti-SRB quenching antibody. FIG. 8C shows fusion assay kinetics recorded after mixing CNTP-LUVs made with unmodified CNTPs and 6-AF-CNTPs with NBD-LUVs.

FIG. 9A-FIG. 9E show neuroblastoma/glioma cells (NG108-15) exposure to free DOX in presence of CNTP-LUVs and free CNTPs. FIG. 9A shows cell survival probabilities and FIG. 9B shows cell proliferation rates measured in the MTT assay after exposing neuroblastoma/glioma (NG108-15) cell culture to 5 µg/mL of free DOX in the growth media in presence of CNTP-LUVs or CNTPs. In the control experiment cells were exposed only to the 5 µg/mL of DOX. (All experiments: N=3, with 3 replicate wells per experiment.) FIG. 9C-FIG. 9E show fluorescence microscopy images of the cell culture using live and dead staining dyes after 48 hrs of exposure to (FIG. 9C) 5 µg/mL of DOX and CNTP-LUVs, (FIG. 9D) 5 µg/mL of DOX and CNTPs, and (FIG. 9E) 5 µg/mL of DOX only. Data indicate that CNTPs and CNTP-LUVs do not create openings in the cell wall that allow external DOX to enter NG108-15 cells.

FIG. 10A shows cell survival probabilities and FIG. 10B shows cell proliferation rates measured in the MTT assay after exposing human breast cancer (MDA-MB231) cell culture to 5 μg/mL of free DOX in the growth media in presence of CNTP-LUVs or CNTPs. In the control experiment cells were exposed only to the 5 μg/mL of DOX. (All experiments: N=3, with 3 replicate wells per experiment.) FIG. 10C-FIG. 10E show fluorescence microscopy images of the cell culture using live and dead staining dyes after 48 hrs of exposure to (FIG. 10C) 5 μg/mL of DOX and CNTP-LUVs, (FIG. 10D) 5 μg/mL of DOX and CNTPs, and (FIG. 10E) 5 μg/mL of DOX only. Data indicate that CNTPs and CNTP-LUVs do not create openings in cell walls that allow external DOX to enter MDA-MB231 cells.

FIG. 11A shows fluorescence microscopy image of NG108-15 cells (stained as described in the cell viability assay subsection in the Methods) after 48 hrs incubation with CNTP-LUVs indicating areas (i, ii, iii) where growth of neural network is visible. FIG. 11B shows fluorescence microscopy image of NG108-15 cells (stained as described in the cell viability assay subsection in the Methods) after 48 hrs incubation with PBS buffer indicating randomly chosen sample areas (i, ii, iii) of the same size as in FIG. 11A. Insets on FIG. 11A and FIG. 11B show enlarged versions of those areas.

DETAILED DESCRIPTION OF THE DISCLOSURE

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Throughout this application, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 10%, 50 or 1%.

The section headings used herein are for organizational purposes only and are not to be construed as limiting the subject matter described.

As used herein, the term "comprising" is intended to mean that the methods include the recited steps or elements, but do not exclude others. "Consisting essentially of" shall mean rendering the claims open only for the inclusion of steps or elements, which do not materially affect the basic and novel characteristics of the claimed methods. "Consisting of" shall mean excluding any element or step not specified in the claim. Embodiments defined by each of these transition terms are within the scope of this disclosure.

Figure 4A:
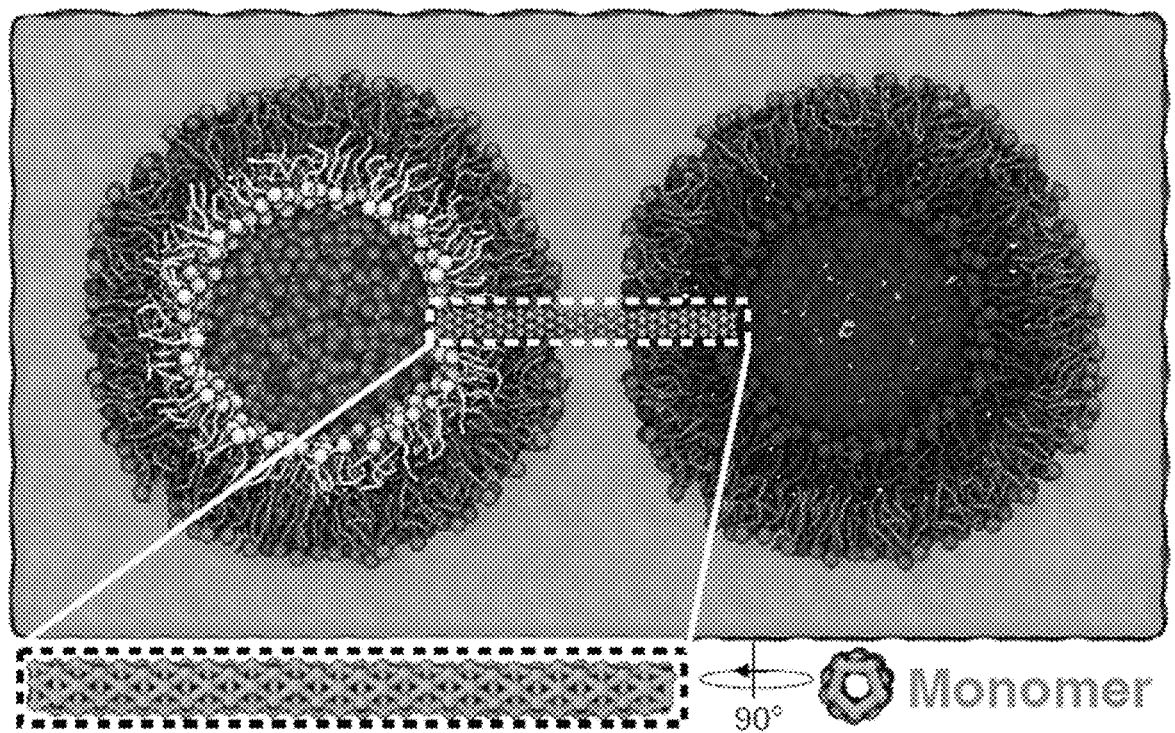
FIG. 4A-FIG. 4C illustrate initial configurations used for coarse-grained simulations. Snapshots of the initial configurations used for simulation of the fusion mediated by CNTP monomer (FIG. 4A), dimer (FIG. 4B), and trimer (FIG. 4C). Water is shown as transparent surface.
Figure 4B:
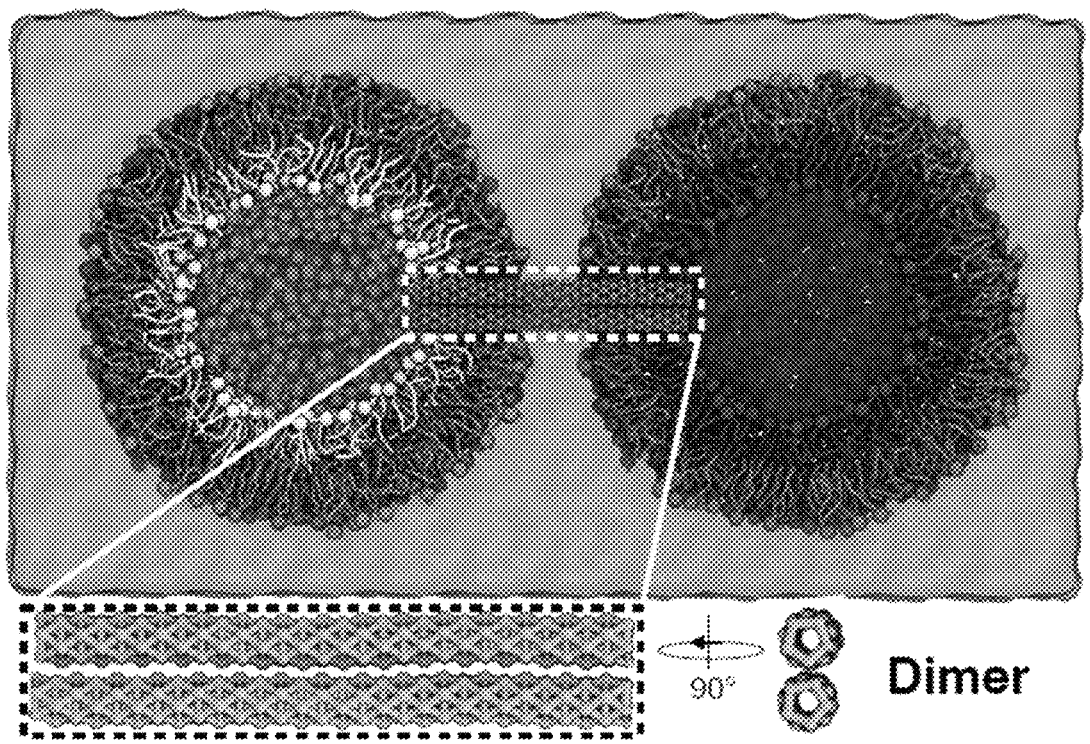
Figure 4C:
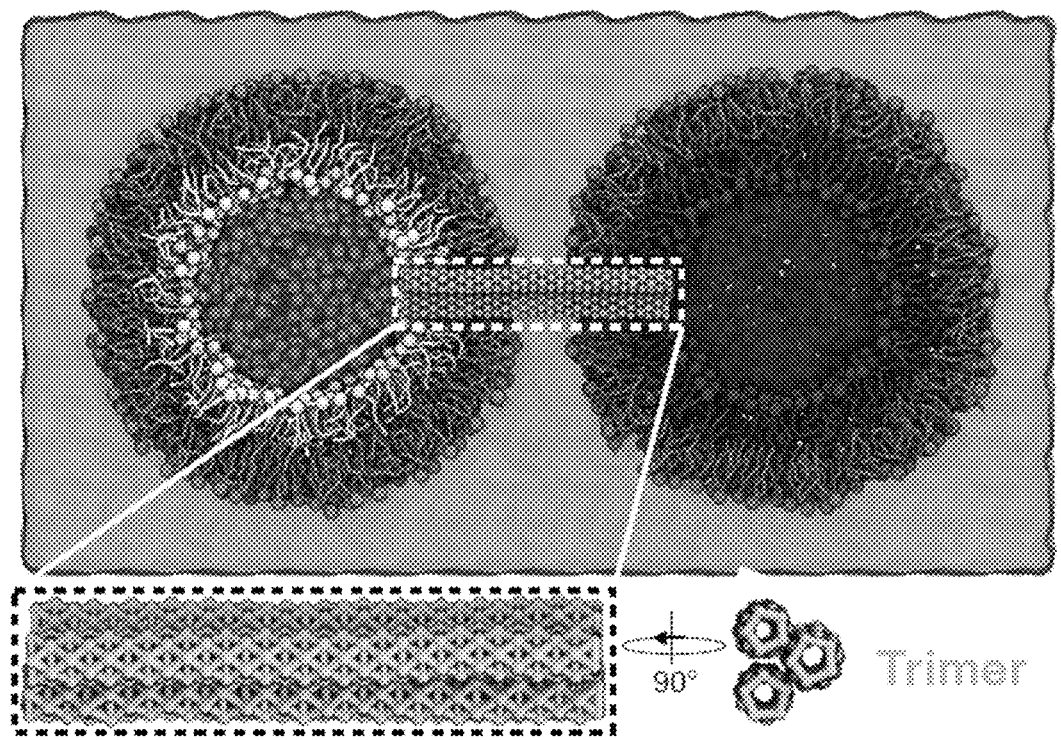

As used herein, the term "nanotube complex" or "SWCNT complex" intends two (dimer) or three (trimer) or more nanotubes or SWCNTs arranged in a non-linear fashion. The trimer or multimer nanotubes can form a complex in a parallel fashion or as a bundle. In some aspect, the complex is embedded in a single lipid-based vesicle. FIG. 4B is illustrative of a nanotube dimer. FIG. 4C is illustrative of a nanotube timer (e.g., a trimer bundle).

Figure 23A:
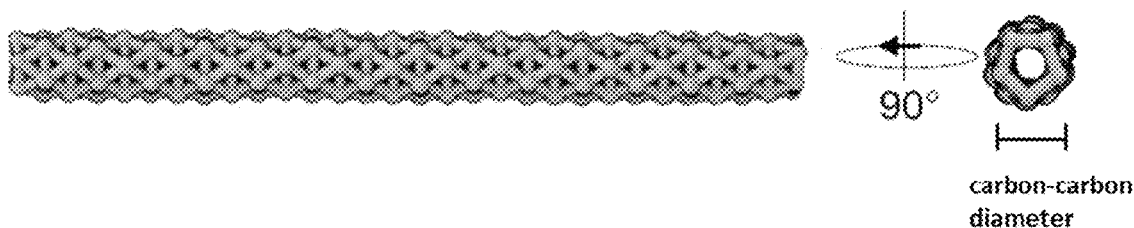
FIG. 23A illustrates a cartoon representation of a carbon nanotube indicating the diameter of the nanotube.

As used herein, the term "inner diameter" is synonymous with "a carbon-carbon diameter" intends for the center-to-center distance between the carbon atoms on the opposite sides of the nanotube rim. Also see FIG. 23A. Unless explicitly stated otherwise stated, when referring to nanotube diameter, the measurement is a "carbon-carbon" diameter.

Modes for Carrying Out the Disclosure

Figure 23B:
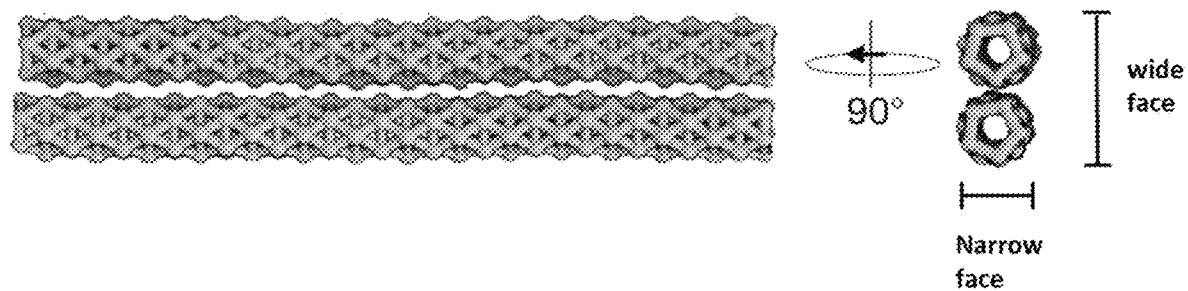
FIG. 23B illustrates a cartoon representation of a nanotube dimer. A cross-section of the nanotube dimer shows a rectangular or rectangular-like shape comprising a narrow face and a wide face.

Disclosed herein, in certain embodiments, is an engineered lipid-based vesicle comprising a nanotube complex embedded or partially embedded within the lipid bilayer circumference of the lipid-based vesicle for delivery of one or more payloads, e.g., drugs. In some aspects, the lipid bilayer is exterior bilayer of the vesicle. In some instances, the nanotube complex is a nanotube dimer. In some cases, the nanotube dimer forms a rectangular or rectangular-like cross-section when viewed from the terminus of the dimer. The rectangular or rectangular-like cross-section comprises a narrow face and a wide face (see FIG. 23B). The rectangular or rectangular-like cross-section of the dimer facilitates a distortion of lipids that comprise the lipid bilayer of the lipid-based vesicle, and facilitates fusion of the lipids of the vesicle with a lipid membrane of a cell. In some cases, the rectangular or rectangular-like cross-section formed by the nanotube dimer provides a superior fusion rate compared to a nanotube monomer comprising an equivalent diameter or a nanotube trimer comprising an equivalent diameter. In one aspect, the total diameter across the major diameter of the nanotube complex is from about 0.7 nm to about 2.8 nm.

In some embodiments, the engineered lipid-based vesicle comprising a nanotube complex embedded within the lipid bilayer circumference of the lipid-based vesicle further enhances therapeutic effect of a payload. In some aspects, the lipid bilayer is exterior bilayer of the vesicle. In some cases, the engineered lipid-based vesicle comprising a nanotube complex embedded within a lipid bilayer of the lipid-based vesicle reduces toxicity that are associated with payload and/or carrier, improves target-site delivery, minimizes off-target effect, improves serum half-life, improves stability, and/or improves efficacy of the payload.

Engineered Lipid-Based Vesicles

In certain embodiments, disclosed herein is an engineered lipid-based vesicle comprising a nanotube complex embedded within a lipid bilayer of a lipid-based vesicle. In some aspects, the lipid bilayer is exterior bilayer of the vesicle. In a further aspect, the nanotube complex is a nanotube dimer. In some instances, the nanotube complex (e.g., a nanotube dimer) is positioned so that a portion of the nanotube (e.g., the nanotube dimer) protrudes out of the lipid-based vesicle and the nanotube does not protrude out of the lipid-based vesicle from both termini. In some instances, the nanotube complex (e.g, the nanotube dimer) is embedded in the lipid bilayer circumference of the vesicle. In some instances, one or more of the nanotube (e.g., the nanotube dimer) is a carbon nanotube, a boron nitride nanotube (BNNT), a $MoS_2$ nanotube, a $MoS_2$-carbon nanotube hybrid, or a carbon-$MoS_2$—$WS_2$ nanotube hybrid. In some cases, the nanotube is a carbon nanotube (e.g., a single-walled carbon nanotube). When a plurality of nanotubes (e.g., nanotube dimers) are present, the nanotubes (e.g., the nanotube dimers) can be the same or different from each other. In some cases, the nanotube (e.g., the nanotube dimer) is a BNNT. In some cases, the nanotube (e.g., the nanotube dimer) is a $MoS_2$ nanotube. In some cases, the nanotube (e.g., the nanotube dimer) is a $MoS_2$-carbon nanotube hybrid or a carbon-$MoS_2$—$WS_2$ nanotube hybrid.

In some embodiments, the nanotube complex comprises, or consists essentially of, or consists of, one or more nanotube monomers. In some instances, the nanotube complex comprises, or consists essentially of, or consists of, a nanotube dimer. In other instances, the nanotube complex comprises, or consists essentially of, or consists of, a nanotube trimer. In additional instances, the nanotube complex comprises, or consists essentially of, or consists of, a conjugated nanotube complex. When a plurality of nanotube complexes (e.g., nanotube dimers) are present, the nanotube complexes (e.g., the nanotube dimers) can be the same or different from each other.

As used herein, the nanotube complex refers to one or more, two or more, three or more, four or more, or five or more nanotube monomers. In some instances, the monomers of the nanotube complex are covalently bound to each other. In other instances, the monomers are non-covalently bound to each other. In some cases, the nanotube complex forms a cluster of monomers, in which the side of each monomer interacts with at least one other monomer within the complex, forming an overall sheet-like structure or as a bundle. In some cases, each monomer within the complex does not bind in tandem with another monomer to elongate the overall length of the complex.

As used herein, a nanotube monomer refers to a single nanotube. In some instances, the nanotube monomer comprises, or consists essentially of, or consists of, an outer diameter of from about 0.7 nm to about 2 nm. In some instances, the nanotube monomer comprises, or consists essentially of, or consists of, a length of from about 6 nm to about 30 nm. In some instances, the nanotube monomer is embedded in the lipid bilayer circumference of the lipid-based vesicle. In some cases, one terminus of the nanotube monomer protrudes out of the lipid-based vesicle while the other terminus is embedded within the lipid bilayer. In additional cases, one terminus of the nanotube monomer protrudes out of the lipid-based vesicle while the other terminus protrudes into the core of the lipid-based vesicle.

As used herein, a nanotube dimer comprises, or consists essentially of, or consists of, two nanotube monomers in which each monomer comprises, or consists essentially of, or consists of, an outer diameter of from about 0.7 nm to about 2 nm. In some instances, each nanotube monomer comprises, or consists essentially of, or consists of, a length of from about 6 nm to about 30 nm. In some cases, the two monomers are covalently bound to each other. In other cases, the two monomers are non-covalently bound to each other. In some cases, the side of the monomers interact, forming a sheet-like structure. From the terminus viewpoint, the dimer forms a rectangular or rectangular-like cross-section (see FIG. 23B). In some cases, the two monomers do not bind in tandem to form an elongated rod. In some cases, one terminus of the nanotube dimer protrudes out of the lipid-based vesicle while the other terminus protrudes into the core of the lipid-based vesicle.

Carbon Nanotube Complexes

In some embodiments, the nanotube complex is a carbon nanotube complex. In some instances, the carbon nanotube is a single-walled carbon nanotube (SWCNT). In some embodiments, the engineered lipid-based vesicle comprises a SWCNT complex embedded within the lipid bilayer circumference of a lipid-based vesicle. In some instances, the SWCNT complex comprises, or consists essentially of, or consists of, one or more SWCNTs. In some instances, the SWCNT complex comprises, or consists essentially of, or consists of, a SWCNT dimer. In other instances, the SWCNT complex comprises, or consists essentially of, or consists of, a SWCNT trimer. In some cases, the SWCNT complex is a conjugated SWCNT complex.

In some embodiments, the SWCNT complex comprises, or consists essentially of, or consists of, at least a first SWCNT monomer and a second SWCNT monomer. In some instances, the first SWCNT monomer comprises a carbon-carbon diameter of from about 0.4 nm to about 1.4 nm, from about 0.4 nm to about 1.3 nm, from about 0.4 nm to about 1.2 nm, from about 0.4 nm to about 1.1 nm, from about 0.4 nm to about 1 nm, from about 0.4 nm to about 0.9 nm, from about 0.4 nm to about 0.8 nm, from about 0.4 nm to about 0.7 nm, from about 0.4 nm to about 0.6 nm, from about 0.5 nm to about 1.4 nm, from about 0.5 nm to about 1.3 nm, from about 0.5 nm to about 1.2 nm, from about 0.5 nm to about 1.1 nm, from about 0.5 nm to about 1 nm, from about 0.5 nm to about 0.9 nm, from about 0.5 nm to about 0.8 nm, from about 0.5 nm to about 0.7 nm, from about 0.6 nm to about 1.4 nm, from about 0.6 nm to about 1.3 nm, from about 0.6 nm to about 1.2 nm, from about 0.6 nm to about 1.1 nm, from about 0.6 nm to about 1 nm, from about 0.6 nm to about 0.9 nm, from about 0.6 nm to about 0.8 nm, from about 0.7 nm to about 1.4 nm, from about 0.7 nm to about 1.3 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 1.4 nm, from about 0.8 nm to about 1.3 nm, from about 0.8 nm to about 1.2 nm, from about 0.8 nm to about 1.1 nm, from about 0.8 nm to about 1 nm, from about 0.9 nm to about 1.4 nm, from about 0.9 nm to about 1.3 nm, from about 0.9 nm to about 1.2 nm, or from about 0.9 nm to about 1.1 nm. In some cases, the first SWCNT monomer comprises a carbon-carbon diameter of about 0.4 nm, about 0.45 nm, about 0.5 nm, about 0.55 nm, about 0.6 nm, about 0.65 nm, about 0.7 nm, about 0.75 nm, about 0.8 nm, about 0.84 nm, about 0.85 nm, about 0.86 nm, about 0.9 nm, about 0.95 nm, about 1 nm, about 1.05 nm, about 1.1 nm, about 1.15 nm, about 1.2 nm, about 1.25 nm, about 1.3 nm, about 1.35 nm, or about 1.4 nm.

In some instances, the first SWCNT monomer comprises an outer diameter of from about 0.7 nm to about 2 nm, from about 0.7 nm to about 1.9 nm, from about 0.7 nm to about 1.85 nm, from about 0.7 nm to about 1.84 nm, from about 0.7 nm to about 1.8 nm, from about 0.7 nm to about 1.7 nm, from about 0.7 nm to about 1.6 nm, from about 0.7 nm to about 1.5 nm, from about 0.7 nm to about 1.4 nm, from about 0.7 nm to about 1.3 nm, from about 0.7 nm to about 1.24 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 2 nm, from about 0.8 nm to about 1.9 nm, from about 0.8 nm to about 1.85 nm, from about 0.8 nm to about 1.84 nm, from about 0.8 nm to about 1.8 nm, from about 0.8 nm to about 1.7 nm, from about 0.8 nm to about 1.6 nm, from about 0.8 nm to about 1.5 nm, from about 0.8 nm to about 1.4 nm, from about 0.8 nm to about 1.3 nm, from about 0.8 nm to about 1.24 nm, from about 0.8 nm to about 1.2 nm, from about 0.8 nm to about 1.1 nm, from about 0.8 nm to about 1 nm, from about 0.9 nm to about 2 nm, from about 0.9 nm to about 1.9 nm, from about 0.9 nm to about 1.85 nm, from about 0.9 nm to about 1.84 nm, from about 0.9 nm to about 1.8 nm, from about 0.9 nm to about 1.7 nm, from about 0.9 nm to about 1.6 nm, from about 0.9 nm to about 1.5 nm, from about 0.9 nm to about 1.4 nm, from about 0.9 nm to about 1.3 nm, from about 0.9 nm to about 1.24 nm, from about 0.9 nm to about 1.2 nm, from about 0.9 nm to about 1.1 nm, from about 1 nm to about 2 nm, from about 1 nm to about 1.9 nm, from about 1 nm to about 1.85 nm, from about 1 nm to about 1.84 nm, from about 1 nm to about 1.8 nm, from about 1 nm to about 1.7 nm, from about 1 nm to about 1.6 nm, from about 1 nm to about 1.5 nm, from about 1 nm to about 1.4 nm, from about 1 nm to about 1.3 nm, from about 1 nm to about 1.24 nm, from about 1 nm to about 1.2 nm, from about 1 nm to about 1.1 nm, from about 1.1 nm to about 2 nm, from about 1.1 nm to about 1.9 nm, from about 1.1 nm to about 1.85 nm, from about 1.1 nm to about 1.84 nm, from about 1.1 nm to about 1.8 nm, from about 1.1 nm to about 1.1 nm, from about 1.1 nm to about 1.6 nm, from about 1.1 nm to about 1.5 nm, from about 1.1 nm to about 1.4 nm, from about 1.1 nm to about 1.3 nm, from about 1.1 nm to about 1.24 nm, from about 1.2 nm to about 2 nm, from about 1.2 nm to about 1.9 nm, from about 1.2 nm to about 1.85 nm, from about 1.2 nm to about 1.84 nm, from about 1.2 nm to about 1.8 nm, from about 1.2 nm to about 1.7 nm, from about 1.2 nm to about 1.6 nm, from about 1.2 nm to about 1.5 nm, from about 1.2 nm to about 1.4 nm.

In some instances, the first SWCNT monomer comprises an outer diameter of about 0.7 nm, about 0.8 nm, about 0.9 nm, about 1 nm, about 1.1 nm, about 1.2 nm, about 1.24 nm, about 1.3 nm, about 1.4 nm, about 1.5 nm, about 1.6 nm, about 1.7 nm, about 1.8 nm, about 1.84 nm, about 1.9 nm, or about 2 nm.

In some instances, the second SWCNT monomer comprises a carbon-carbon diameter of from about 0.4 nm to about 1.4 nm, from about 0.4 nm to about 1.3 nm, from about 0.4 nm to about 1.2 nm, from about 0.4 nm to about 1.1 nm, from about 0.4 nm to about 1 nm, from about 0.4 nm to about 0.9 nm, from about 0.4 nm to about 0.8 nm, from about 0.4 nm to about 0.7 nm, from about 0.4 nm to about 0.6 nm, from about 0.5 nm to about 1.4 nm, from about 0.5 nm to about 1.3 nm, from about 0.5 nm to about 1.2 nm, from about 0.5 nm to about 1.1 nm, from about 0.5 nm to about 1 nm, from about 0.5 nm to about 0.9 nm, from about 0.5 nm to about 0.8 nm, from about 0.5 nm to about 0.7 nm, from about 0.6 nm to about 1.4 nm, from about 0.6 nm to about 1.3 nm, from about 0.6 nm to about 1.2 nm, from about 0.6 nm to about 1.1 nm, from about 0.6 nm to about 1 nm, from about 0.6 nm to about 0.9 nm, from about 0.6 nm to about 0.8 nm, from about 0.7 nm to about 1.4 nm, from about 0.7 nm to about 1.3 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 1.4 nm, from about 0.8 nm to about 1.3 nm, from about 0.8 nm to about 1.2 nm, from about 0.8 nm to about 1.1 nm, from about 0.8 nm to about 1 nm, from about 0.9 nm to about 1.4 nm, from about 0.9 nm to about 1.3 nm, from about 0.9 nm to about 1.2 nm, or from about 0.9 nm to about 1.1 nm. In some cases, the second SWCNT monomer comprises a carbon-carbon diameter of about 0.4 nm, about 0.45 nm, about 0.5 nm, about 0.55 nm, about 0.6 nm, about 0.65 nm, about 0.7 nm, about 0.75 nm, about 0.8 nm, about 0.84 nm, about 0.85 nm, about 0.86 nm, about 0.9 nm, about 0.95 nm, about 1 nm, about 1.05 nm, about 1.1 nm, about 1.15 nm, about 1.2 nm, about 1.25 nm, about 1.3 nm, about 1.35 nm, or about 1.4 nm.

In some instances, the second SWCNT monomer comprises an outer diameter of from about 0.7 nm to about 2 nm, from about 0.7 nm to about 1.9 nm, from about 0.7 nm to about 1.85 nm, from about 0.7 nm to about 1.84 nm, from about 0.7 nm to about 1.8 nm, from about 0.7 nm to about 1.7 nm, from about 0.7 nm to about 1.6 nm, from about 0.7 nm to about 1.5 nm, from about 0.7 nm to about 1.4 nm, from about 0.7 nm to about 1.3 nm, from about 0.7 nm to about 1.24 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 2 nm, from about 0.8 nm to about 1.9 nm, from about 0.8 nm to about 1.85 nm, from about 0.8 nm to about 1.84 nm, from about 0.8 nm to about 1.8 nm, from about 0.8 nm to about 1.7 nm, from about 0.8 nm to about 1.6 nm, from about 0.8 nm to about 1.5 nm, from about 0.8 nm to about 1.4 nm, from about 0.8 nm to about 1.3 nm, from about 0.8 nm to about 1.24 nm, from about 0.8 nm to about 1.2 nm, from about 0.8 nm to about 1.1 nm, from about 0.8 nm to about 1 nm, from about 0.9 nm to about 2 nm, from about 0.9 nm to about 1.9 nm, from about 0.9 nm to about 1.85 nm, from about 0.9 nm to about 1.84 nm, from about 0.9 nm to about 1.8 nm, from about 0.9 nm to about 1.7 nm, from about 0.9 nm to about 1.6 nm, from about 0.9 nm to about 1.5 nm, from about 0.9 nm to about 1.4 nm, from about 0.9 nm to about 1.3 nm, from about 0.9 nm to about 1.24 nm, from about 0.9 nm to about 1.2 nm, from about 0.9 nm to about 1.1 nm, from about 1 nm to about 2 nm, from about 1 nm to about 1.9 nm, from about 1 nm to about 1.85 nm, from about 1 nm to about 1.84 nm, from about 1 nm to about 1.8 nm, from about 1 nm to about 1.7 nm, from about 1 nm to about 1.6 nm, from about 1 nm to about 1.5 nm, from about 1 nm to about 1.4 nm, from about 1 nm to about 1.3 nm, from about 1 nm to about 1.24 nm, from about 1 nm to about 1.2 nm, from about 1 nm to about 1.1 nm, from about 1.1 nm to about 2 nm, from about 1.1 nm to about 1.9 nm, from about 1.1 nm to about 1.85 nm, from about 1.1 nm to about 1.84 nm, from about 1.1 nm to about 1.8 nm, from about 1.1 nm to about 1.1 nm, from about 1.1 nm to about 1.6 nm, from about 1.1 nm to about 1.5 nm, from about 1.1 nm to about 1.4 nm, from about 1.1 nm to about 1.3 nm, from about 1.1 nm to about 1.24 nm, from about 1.2 nm to about 2 nm, from about 1.2 nm to about 1.9 nm, from about 1.2 nm to about 1.85 nm, from about 1.2 nm to about 1.84 nm, from about 1.2 nm to about 1.8 nm, from about 1.2 nm to about 1.7 nm, from about 1.2 nm to about 1.6 nm, from about 1.2 nm to about 1.5 nm, from about 1.2 nm to about 1.4 nm.

In some instances, the second SWCNT monomer comprises an outer diameter of about 0.7 nm, about 0.8 nm, about 0.9 nm, about 1 nm, about 1.1 nm, about 1.2 nm, about 1.24 nm, about 1.3 nm, about 1.4 nm, about 1.5 nm, about 1.6 nm, about 1.7 nm, about 1.8 nm, about 1.84 nm, about 1.9 nm, or about 2 nm.

In some embodiments, the SWCNT complex is a SWCNT dimer comprising a first SWCNT monomer and a second SWCNT monomer. In some instances, the SWCNT dimer comprises a total inner diameter across the major axis of the dimer of from about 0.8 nm to about 2.8 nm, from about 0.8 nm to about 2.6 nm, from about 0.8 nm to about 2.5 nm, from about 0.8 nm to about 2.4 nm, from about 0.8 nm to about 2.2 nm, from about 0.8 nm to about 2 nm, from about 0.8 nm to about 1.8 nm, from about 0.8 nm to about 1.6 nm, from about 0.8 nm to about 1.4 nm, from about 1 nm to about 2.8 nm, from about 1 nm to about 2.6 nm, from about 1 nm to about 2.5 nm, from about 1 nm to about 2.4 nm, from about 1 nm to about 2.2 nm, from about 1 nm to about 2 nm, from about 1 nm to about 1.8 nm, from about 1 nm to about 1.6 nm, from about 1 nm to about 1.4 nm, from about 1.2 nm to about 2.8 nm, from about 1.2 nm to about 2.6 nm, from about 1.2 nm to about 2.5 nm, from about 1.2 nm to about 2.4 nm, from about 1.2 nm to about 2.2 nm, from about 1.2 nm to about 2 nm, from about 1.2 nm to about 1.8 nm, from about 1.2 nm to about 1.6 nm, from about 1.6 nm to about 2.8 nm, from about 1.6 nm to about 2.6 nm, from about 1.6 nm to about 2.5 nm, from about 1.6 nm to about 2.4 nm, from about 1.6 nm to about 2.2 nm, from about 1.6 nm to about 2 nm, or from about 1.6 nm to about 1.8 nm. In some cases, the total inner diameter is calculated as the sum of the carbon-carbon diameter of the first SWCNT monomer and the carbon-carbon diameter of the second SWCNT monomer.

In some embodiments, the SWCNT complex is a SWCNT trimer, comprising a first SWCNT monomer, a second SWCNT monomer, and a third SWCNT monomer, in which the three SWCNTs are arranged in a linear parallel fashion and in which the trimer does not form a bundle. In some instances, the third SWCNT monomer comprises a carbon-carbon diameter of from about 0.4 nm to about 1.4 nm, from about 0.4 nm to about 1.3 nm, from about 0.4 nm to about 1.2 nm, from about 0.4 nm to about 1.1 nm, from about 0.4 nm to about 1 nm, from about 0.4 nm to about 0.9 nm, from about 0.4 nm to about 0.8 nm, from about 0.4 nm to about 0.7 nm, from about 0.4 nm to about 0.6 nm, from about 0.5 nm to about 1.4 nm, from about 0.5 nm to about 1.3 nm, from about 0.5 nm to about 1.2 nm, from about 0.5 nm to about 1.1 nm, from about 0.5 nm to about 1 nm, from about 0.5 nm to about 0.9 nm, from about 0.5 nm to about 0.8 nm, from about 0.5 nm to about 0.7 nm, from about 0.6 nm to about 1.4 nm, from about 0.6 nm to about 1.3 nm, from about 0.6 nm to about 1.2 nm, from about 0.6 nm to about 1.1 nm, from about 0.6 nm to about 1 nm, from about 0.6 nm to about 0.9 nm, from about 0.6 nm to about 0.8 nm, from about 0.7 nm to about 1.4 nm, from about 0.7 nm to about 1.3 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 1.4 nm, from about 0.8 nm to about 1.3 nm, from about 0.8 nm to about 1.2 nm, from about 0.8 nm to about 1.1 nm, from about 0.8 nm to about 1 nm, from about 0.9 nm to about 1.4 nm, from about 0.9 nm to about 1.3 nm, from about 0.9 nm to about 1.2 nm, or from about 0.9 nm to about 1.1 nm. In some cases, the third SWCNT monomer comprises a carbon-carbon diameter of about 0.4 nm, about 0.45 nm, about 0.5 nm, about 0.55 nm, about 0.6 nm, about 0.65 nm, about 0.7 nm, about 0.75 nm, about 0.8 nm, about 0.84 nm, about 0.85 nm, about 0.86 nm, about 0.9 nm, about 0.95 nm, about 1 nm, about 1.05 nm, about 1.1 nm, about 1.15 nm, about 1.2 nm, about 1.25 nm, about 1.3 nm, about 1.35 nm, or about 1.4 nm.

In some embodiments, the SWCNT trimer comprises a total inner diameter of from about 0.8 nm to about 2.8 nm, from about 0.8 nm to about 2.6 nm, from about 0.8 nm to about 2.5 nm, from about 0.8 nm to about 2.4 nm, from about 0.8 nm to about 2.2 nm, from about 0.8 nm to about 2 nm, from about 0.8 nm to about 1.8 nm, from about 0.8 nm to about 1.6 nm, from about 0.8 nm to about 1.4 nm, from about 1 nm to about 2.8 nm, from about 1 nm to about 2.6 nm, from about 1 nm to about 2.5 nm, from about 1 nm to about 2.4 nm, from about 1 nm to about 2.2 nm, from about 1 nm to about 2 nm, from about 1 nm to about 1.8 nm, from about 1 nm to about 1.6 nm, from about 1 nm to about 1.4 nm, from about 1.2 nm to about 2.8 nm, from about 1.2 nm to about 2.6 nm, from about 1.2 nm to about 2.5 nm, from about 1.2 nm to about 2.4 nm, from about 1.2 nm to about 2.2 nm, from about 1.2 nm to about 2 nm, from about 1.2 nm to about 1.8 nm, from about 1.2 nm to about 1.6 nm, from about 1.6 nm to about 2.8 nm, from about 1.6 nm to about 2.6 nm, from about 1.6 nm to about 2.5 nm, from about 1.6 nm to about 2.4 nm, from about 1.6 nm to about 2.2 nm, from about 1.6 nm to about 2 nm, or from about 1.6 nm to about 1.8 nm. In some cases, the total inner diameter is calculated as the sum of the carbon-carbon diameter of the first SWCNT monomer, the carbon-carbon diameter of the second SWCNT monomer, and the carbon-carbon diameter of the third SWCNT monomer.

In some instances, the one or more SWCNT monomers have a CNT length of from about 6 nm to about 30 nm. In some instances, the one or more SWCNT monomers have a CNT length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the first SWCNT monomer has a CNT length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the second SWCNT monomer has a CNT length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the third SWCNT monomer has a CNT length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the one or more SWCNT monomers have a CNT length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the first SWCNT monomer has a CNT length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the second SWCNT monomer has a CNT length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the third SWCNT monomer has a CNT length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the lengths of the first SWCNT monomer, the second SWCNT monomer, and optionally the third SWCNT monomer are substantially the same. As used herein, "substantially the same" in reference to length intends to be less than about 5%, or alternatively less than about 4%, less than about 3%, less than about 2%, or less than about 1% difference from a reference length. The reference length is, e.g., the first SWCNT monomer, the second SWCNT monomer, or optionally the third SWCNT monomer.

In additional instances, the lengths of the first SWCNT monomer, the second SWCNT monomer, and optionally the third SWCNT monomer are different, provided that the SWCNT complex formed facilitate a fusion of the engineered lipid-based vesicle to a target cell.

In some embodiments, the engineered lipid-based vesicle comprises two or more SWCNT complexes. In some cases, the engineered lipid-based vesicle comprises three or more SWCNT complexes, four or more SWCNT complexes, five or more SWCNT complexes, six or more SWCNT complexes, seven or more SWCNT complexes, or eight or more SWCNT complexes. In some cases, each of the SWCNT complexes do not interact or bind to another SWCNT complex within the engineered lipid-based vesicle.

In some instances, the SWCNT complex is a SWCNT dimer. In such instances, the engineered lipid-based vesicle comprises two or more SWCNT dimers, three or more SWCNT dimers, four or more SWCNT dimers, five or more SWCNT dimers, six or more SWCNT dimers, seven or more SWCNT dimers, or eight or more SWCNT dimers. In some cases, each of the SWCNT dimers do not interact or bind to another SWCNT dimer within the engineered lipid-based vesicle.

In some embodiments, a SWCNT complex (e.g., SWCNT dimer) described herein is a conjugated SWCNT complex (e.g., SWCNT dimer). In some instances, the conjugation is a terminal conjugation in which the end of the SWCNTs are linked together. In some cases, the conjugation (e.g., the terminal conjugation) is a covalent conjugation. In other cases, the conjugation (e.g., the terminal conjugation) is a non-covalent conjugation.

In some instances, the terminal conjugation is located at the terminus that is within the lipid-based vesicle (e.g., either within the vesicle lumen or within the bilayer). In other instances, the terminal conjugation is located at the terminus that is outside of the lipid-based vesicle.

In some cases, the terminal conjugation is located at the carboxyl termini of the first SWCNT and the second SWCNT that form the SWCNT dimer. In some cases, the terminal conjugation is located at the carboxyl termini of the first SWCNT, the second SWCNT, and the third SWCNT monomer that form the SWCNT trimer. In some cases, the conjugated carboxyl termini of the SWCNT dimer or the SWCNT trimer is located within the lipid-based vesicle. In additional cases, the conjugated carboxyl termini of the SWCNT dimer or the SWCNT trimer is located outside the lipid-based vesicle.

In some embodiments, the SWCNT complex (e.g., the SWCNT dimer) is crosslinked at the termini which comprises one or more COOH groups. In some cases, the crosslinking chemistry involves a carbodiimide crosslinker that modifies the COOH group to generate a cross-linked complex. Exemplary carbodiimide crosslinkers include, but are not limited to, dicyclohexylcarbodiimide (DCC), N,N'-diisopropylcarbodiimide (DIC), 1-ethyl-3-(3-dimethylaminopropyl)carbodiimide (EDC), or 1-cyclohexyl-(2-morpholinoethyl)carbodiimide metho-p-toluene sulfonate (CMCT or CMC). In some cases, the SWCNT complex is crosslinked via a carbodiimide crosslinker, optionally selected from dicyclohexylcarbodiimide (DCC), N,N'-diisopropylcarbodiimide (DIC), 1-ethyl-3-(3-dimethylaminopropyl)carbodiimide (EDC), or 1-cyclohexyl-(2-morpholinoethyl)carbodiimide metho-p-toluene sulfonate (CMCT or CMC). In some cases, the SWCNT complex is crosslinked via EDC.

In some embodiments, the SWCNT complex (e.g., the SWCNT dimer) is conjugated at the termini which comprise one or more COOH groups and the conjugation chemistry comprises a click chemistry. In some instances, the click chemistry comprises a 1,3-dipolar cycloaddition reaction comprising an azide and a phosphine. In some instances, the conjugation reaction is catalyzed by copper. In some instances, the conjugation reaction comprises reaction of an azide with a strained olefin, a strained alkyne, or a cycloalkyne such as OCT, DIFO, DIFBO, DIBO, BARAC, TMTH, or other strained cycloalkyne, the structures of which are shown in Gong, Y., Pan, L. Tett. Lett. 2015, 56, 2123. In some embodiments, the 1,3-dipolar cycloaddition reaction is catalyzed by light ("photoclick"). In some embodiments, the conjugation reaction comprises reaction of a terminal allyl group with a tetrazole and light or a terminal alkynyl group with a tetrazole and light.

In some embodiments, the SWCNT complex (e.g., the SWCNT dimer) is further coated with an amphiphilic material. In some instances, the amphiphilic material comprises a phospholipid, a block copolymer, or a combination thereof. As used herein, a phospholipid is a natural phospholipid or a synthetic phospholipid. Exemplary natural phospholipids include, but are not limited to, phosphotidylcholine, phosphotidylserine, phosphotidylethanolamine, and phosphatidylinositol. Exemplary synthetic phospholipids include, but are not limited to, phosphatidic acid, phosphatidylcholine, phosphatidylglycerol, phosphatidylethanolamine, phosphatidylserine, and PEG phospholipid. Exemplary block copolymers include, but are not limited to, poly(ethylene oxide) (PEO)-poly(propylene oxide) (PPO) copolymer and PEO-PPO-PEO copolymer. In some instances, about 100%, 90%, 80%, 70%, 60%, 50%, 40%, or 30% of the SWCNT complex is coated with the amphiphilic material.

Boron Nitride Nanotube Complexes

In some embodiments, the nanotube complex is a boron nitride nanotube (BNNT) complex. In some instances, the engineered lipid-based vesicle comprises, or consists essentially of, or consists of, a BNNT complex embedded within the lipid bilayer circumference of a lipid-based vesicle. In some instances, the BNNT complex comprises, or consists essentially of, or consists of, one or more BNNT monomers. In some instances, the BNNT complex comprises, or consists essentially of, or consists of, a BNNT dimer. In other instances, the BNNT complex comprises, or consists essentially of, or consists of, a BNNT trimer. In additional instances, the BNNT complex comprises, or consists essentially of, or consists of, a conjugated BNNT complex.

In some embodiments, the BNNT complex comprises, or consists essentially of, or consists of, at least a first BNNT monomer and a second BNNT monomer. In some instances, the first BNNT monomer comprises an inner diameter of from about 0.4 nm to about 1.4 nm, from about 0.4 nm to about 1.3 nm, from about 0.4 nm to about 1.2 nm, from about 0.4 nm to about 1.1 nm, from about 0.4 nm to about 1 nm, from about 0.4 nm to about 0.9 nm, from about 0.4 nm to about 0.8 nm, from about 0.4 nm to about 0.7 nm, from about 0.4 nm to about 0.6 nm, from about 0.5 nm to about 1.4 nm, from about 0.5 nm to about 1.3 nm, from about 0.5 nm to about 1.2 nm, from about 0.5 nm to about 1.1 nm, from about 0.5 nm to about 1 nm, from about 0.5 nm to about 0.9 nm, from about 0.5 nm to about 0.8 nm, from about 0.5 nm to about 0.7 nm, from about 0.6 nm to about 1.4 nm, from about 0.6 nm to about 1.3 nm, from about 0.6 nm to about 1.2 nm, from about 0.6 nm to about 1.1 nm, from about 0.6 nm to about 1 nm, from about 0.6 nm to about 0.9 nm, from about 0.6 nm to about 0.8 nm, from about 0.7 nm to about 1.4 nm, from about 0.7 nm to about 1.3 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 1.4 nm, from about 0.8 nm to about 1.3 nm, from about 0.8 nm to about 1.2 nm, from about 0.8 nm to about 1.1 nm, from about 0.8 nm to about 1 nm, from about 0.9 nm to about 1.4 nm, from about 0.9 nm to about 1.3 nm, from about 0.9 nm to about 1.2 nm, or from about 0.9 nm to about 1.1 nm. In some cases, the first BNNT monomer comprises an inner diameter of about 0.4 nm, about 0.45 nm, about 0.5 nm, about 0.55 nm, about 0.6 nm, about 0.65 nm, about 0.7 nm, about 0.75 nm, about 0.8 nm, about 0.84 nm, about 0.85 nm, about 0.86 nm, about 0.9 nm, about 0.95 nm, about 1 nm, about 1.05 nm, about 1.1 nm, about 1.15 nm, about 1.2 nm, about 1.25 nm, about 1.3 nm, about 1.35 nm, or about 1.4 nm.

In some instances, the first BNNT monomer comprises an outer diameter of from about 0.7 nm to about 2 nm, from about 0.7 nm to about 1.9 nm, from about 0.7 nm to about 1.85 nm, from about 0.7 nm to about 1.84 nm, from about 0.7 nm to about 1.8 nm, from about 0.7 nm to about 1.7 nm, from about 0.7 nm to about 1.6 nm, from about 0.7 nm to about 1.5 nm, from about 0.7 nm to about 1.4 nm, from about 0.7 nm to about 1.3 nm, from about 0.7 nm to about 1.24 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 2 nm, from about 0.8 nm to about 1.9 nm, from about 0.8 nm to about 1.85 nm, from about 0.8 nm to about 1.84 nm, from about 0.8 nm to about 1.8 nm, from about 0.8 nm to about 1.7 nm, from about 0.8 nm to about 1.6 nm, from about 0.8 nm to about 1.5 nm, from about 0.8 nm to about 1.4 nm, from about 0.8 nm to about 1.3 nm, from about 0.8 nm to about 1.24 nm, from about 0.8 nm to about 1.2 nm, from about 0.8 nm to about 1.1 nm, from about 0.8 nm to about 1 nm, from about 0.9 nm to about 2 nm, from about 0.9 nm to about 1.9 nm, from about 0.9 nm to about 1.85 nm, from about 0.9 nm to about 1.84 nm, from about 0.9 nm to about 1.8 nm, from about 0.9 nm to about 1.7 nm, from about 0.9 nm to about 1.6 nm, from about 0.9 nm to about 1.5 nm, from about 0.9 nm to about 1.4 nm, from about 0.9 nm to about 1.3 nm, from about 0.9 nm to about 1.24 nm, from about 0.9 nm to about 1.2 nm, from about 0.9 nm to about 1.1 nm, from about 1 nm to about 2 nm, from about 1 nm to about 1.9 nm, from about 1 nm to about 1.85 nm, from about 1 nm to about 1.84 nm, from about 1 nm to about 1.8 nm, from about 1 nm to about 1.7 nm, from about 1 nm to about 1.6 nm, from about 1 nm to about 1.5 nm, from about 1 nm to about 1.4 nm, from about 1 nm to about 1.3 nm, from about 1 nm to about 1.24 nm, from about 1 nm to about 1.2 nm, from about 1 nm to about 1.1 nm, from about 1.1 nm to about 2 nm, from about 1.1 nm to about 1.9 nm, from about 1.1 nm to about 1.85 nm, from about 1.1 nm to about 1.84 nm, from about 1.1 nm to about 1.8 nm, from about 1.1 nm to about 1.1 nm, from about 1.1 nm to about 1.6 nm, from about 1.1 nm to about 1.5 nm, from about 1.1 nm to about 1.4 nm, from about 1.1 nm to about 1.3 nm, from about 1.1 nm to about 1.24 nm, from about 1.2 nm to about 2 nm, from about 1.2 nm to about 1.9 nm, from about 1.2 nm to about 1.85 nm, from about 1.2 nm to about 1.84 nm, from about 1.2 nm to about 1.8 nm, from about 1.2 nm to about 1.7 nm, from about 1.2 nm to about 1.6 nm, from about 1.2 nm to about 1.5 nm, from about 1.2 nm to about 1.4 nm.

In some instances, the first BNNT monomer comprises an outer diameter of about 0.7 nm, about 0.8 nm, about 0.9 nm, about 1 nm, about 1.1 nm, about 1.2 nm, about 1.24 nm, about 1.3 nm, about 1.4 nm, about 1.5 nm, about 1.6 nm, about 1.7 nm, about 1.8 nm, about 1.84 nm, about 1.9 nm, or about 2 nm.

In some instances, the second BNNT monomer comprises an inner diameter of from about 0.4 nm to about 1.4 nm, from about 0.4 nm to about 1.3 nm, from about 0.4 nm to about 1.2 nm, from about 0.4 nm to about 1.1 nm, from about 0.4 nm to about 1 nm, from about 0.4 nm to about 0.9 nm, from about 0.4 nm to about 0.8 nm, from about 0.4 nm to about 0.7 nm, from about 0.4 nm to about 0.6 nm, from about 0.5 nm to about 1.4 nm, from about 0.5 nm to about 1.3 nm, from about 0.5 nm to about 1.2 nm, from about 0.5 nm to about 1.1 nm, from about 0.5 nm to about 1 nm, from about 0.5 nm to about 0.9 nm, from about 0.5 nm to about 0.8 nm, from about 0.5 nm to about 0.7 nm, from about 0.6 nm to about 1.4 nm, from about 0.6 nm to about 1.3 nm, from about 0.6 nm to about 1.2 nm, from about 0.6 nm to about 1.1 nm, from about 0.6 nm to about 1 nm, from about 0.6 nm to about 0.9 nm, from about 0.6 nm to about 0.8 nm, from about 0.7 nm to about 1.4 nm, from about 0.7 nm to about 1.3 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 1.4 nm, from about 0.8 nm to about 1.3 nm, from about 0.8 nm to about 1.2 nm, from about 0.8 nm to about 1.1 nm, from about 0.8 nm to about 1 nm, from about 0.9 nm to about 1.4 nm, from about 0.9 nm to about 1.3 nm, from about 0.9 nm to about 1.2 nm, or from about 0.9 nm to about 1.1 nm. In some cases, the second BNNT monomer comprises an inner diameter of about 0.4 nm, about 0.45 nm, about 0.5 nm, about 0.55 nm, about 0.6 nm, about 0.65 nm, about 0.7 nm, about 0.75 nm, about 0.8 nm, about 0.84 nm, about 0.85 nm, about 0.86 nm, about 0.9 nm, about 0.95 nm, about 1 nm, about 1.05 nm, about 1.1 nm, about 1.15 nm, about 1.2 nm, about 1.25 nm, about 1.3 nm, about 1.35 nm, or about 1.4 nm.

In some instances, the second BNNT monomer comprises an outer diameter of from about 0.7 nm to about 2 nm, from about 0.7 nm to about 1.9 nm, from about 0.7 nm to about 1.85 nm, from about 0.7 nm to about 1.84 nm, from about 0.7 nm to about 1.8 nm, from about 0.7 nm to about 1.7 nm, from about 0.7 nm to about 1.6 nm, from about 0.7 nm to about 1.5 nm, from about 0.7 nm to about 1.4 nm, from about 0.7 nm to about 1.3 nm, from about 0.7 nm to about 1.24 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 2 nm, from about 0.8 nm to about 1.9 nm, from about 0.8 nm to about 1.85 nm, from about 0.8 nm to about 1.84 nm, from about 0.8 nm to about 1.8 nm, from about 0.8 nm to about 1.7 nm, from about 0.8 nm to about 1.6 nm, from about 0.8 nm to about 1.5 nm, from about 0.8 nm to about 1.4 nm, from about 0.8 nm to about 1.3 nm, from about 0.8 nm to about 1.24 nm, from about 0.8 nm to about 1.2 nm, from about 0.8 nm to about 1.1 nm, from about 0.8 nm to about 1 nm, from about 0.9 nm to about 2 nm, from about 0.9 nm to about 1.9 nm, from about 0.9 nm to about 1.85 nm, from about 0.9 nm to about 1.84 nm, from about 0.9 nm to about 1.8 nm, from about 0.9 nm to about 1.7 nm, from about 0.9 nm to about 1.6 nm, from about 0.9 nm to about 1.5 nm, from about 0.9 nm to about 1.4 nm, from about 0.9 nm to about 1.3 nm, from about 0.9 nm to about 1.24 nm, from about 0.9 nm to about 1.2 nm, from about 0.9 nm to about 1.1 nm, from about 1 nm to about 2 nm, from about 1 nm to about 1.9 nm, from about 1 nm to about 1.85 nm, from about 1 nm to about 1.84 nm, from about 1 nm to about 1.8 nm, from about 1 nm to about 1.7 nm, from about 1 nm to about 1.6 nm, from about 1 nm to about 1.5 nm, from about 1 nm to about 1.4 nm, from about 1 nm to about 1.3 nm, from about 1 nm to about 1.24 nm, from about 1 nm to about 1.2 nm, from about 1 nm to about 1.1 nm, from about 1.1 nm to about 2 nm, from about 1.1 nm to about 1.9 nm, from about 1.1 nm to about 1.85 nm, from about 1.1 nm to about 1.84 nm, from about 1.1 nm to about 1.8 nm, from about 1.1 nm to about 1.1 nm, from about 1.1 nm to about 1.6 nm, from about 1.1 nm to about 1.5 nm, from about 1.1 nm to about 1.4 nm, from about 1.1 nm to about 1.3 nm, from about 1.1 nm to about 1.24 nm, from about 1.2 nm to about 2 nm, from about 1.2 nm to about 1.9 nm, from about 1.2 nm to about 1.85 nm, from about 1.2 nm to about 1.84 nm, from about 1.2 nm to about 1.8 nm, from about 1.2 nm to about 1.7 nm, from about 1.2 nm to about 1.6 nm, from about 1.2 nm to about 1.5 nm, from about 1.2 nm to about 1.4 nm.

In some instances, the second BNNT monomer comprises an outer diameter of about 0.7 nm, about 0.8 nm, about 0.9 nm, about 1 nm, about 1.1 nm, about 1.2 nm, about 1.24 nm, about 1.3 nm, about 1.4 nm, about 1.5 nm, about 1.6 nm, about 1.7 nm, about 1.8 nm, about 1.84 nm, about 1.9 nm, or about 2 nm.

In some embodiments, the BNNT complex is a BNNT dimer comprising a first BNNT monomer and a second BNNT monomer. In some instances, the BNNT dimer comprises a total inner diameter across the major axis of the dimer of from about 0.8 nm to about 2.8 nm, from about 0.8 nm to about 2.6 nm, from about 0.8 nm to about 2.5 nm, from about 0.8 nm to about 2.4 nm, from about 0.8 nm to about 2.2 nm, from about 0.8 nm to about 2 nm, from about 0.8 nm to about 1.8 nm, from about 0.8 nm to about 1.6 nm, from about 0.8 nm to about 1.4 nm, from about 1 nm to about 2.8 nm, from about 1 nm to about 2.6 nm, from about 1 nm to about 2.5 nm, from about 1 nm to about 2.4 nm, from about 1 nm to about 2.2 nm, from about 1 nm to about 2 nm, from about 1 nm to about 1.8 nm, from about 1 nm to about 1.6 nm, from about 1 nm to about 1.4 nm, from about 1.2 nm to about 2.8 nm, from about 1.2 nm to about 2.6 nm, from about 1.2 nm to about 2.5 nm, from about 1.2 nm to about 2.4 nm, from about 1.2 nm to about 2.2 nm, from about 1.2 nm to about 2 nm, from about 1.2 nm to about 1.8 nm, from about 1.2 nm to about 1.6 nm, from about 1.6 nm to about 2.8 nm, from about 1.6 nm to about 2.6 nm, from about 1.6 nm to about 2.5 nm, from about 1.6 nm to about 2.4 nm, from about 1.6 nm to about 2.2 nm, from about 1.6 nm to about 2 nm, or from about 1.6 nm to about 1.8 nm. In some cases, the total inner diameter is calculated as the sum of the inner diameter of the first BNNT monomer and the inner diameter of the second BNNT monomer.

In some embodiments, the BNNT complex is a BNNT trimer, comprising a first BNNT monomer, a second BNNT monomer, and a third BNNT monomer, in which the three BNNTs are arranged in a linear parallel fashion and in which the trimer does not form a bundle. In some instances, the third BNNT monomer comprises an inner diameter of from about 0.4 nm to about 1.4 nm, from about 0.4 nm to about 1.3 nm, from about 0.4 nm to about 1.2 nm, from about 0.4 nm to about 1.1 nm, from about 0.4 nm to about 1 nm, from about 0.4 nm to about 0.9 nm, from about 0.4 nm to about 0.8 nm, from about 0.4 nm to about 0.7 nm, from about 0.4 nm to about 0.6 nm, from about 0.5 nm to about 1.4 nm, from about 0.5 nm to about 1.3 nm, from about 0.5 nm to about 1.2 nm, from about 0.5 nm to about 1.1 nm, from about 0.5 nm to about 1 nm, from about 0.5 nm to about 0.9 nm, from about 0.5 nm to about 0.8 nm, from about 0.5 nm to about 0.7 nm, from about 0.6 nm to about 1.4 nm, from about 0.6 nm to about 1.3 nm, from about 0.6 nm to about 1.2 nm, from about 0.6 nm to about 1.1 nm, from about 0.6 nm to about 1 nm, from about 0.6 nm to about 0.9 nm, from about 0.6 nm to about 0.8 nm, from about 0.7 nm to about 1.4 nm, from about 0.7 nm to about 1.3 nm, from about 0.7 nm to about 1.2 nm, from about 0.7 nm to about 1.1 nm, from about 0.7 nm to about 1 nm, from about 0.7 nm to about 0.9 nm, from about 0.8 nm to about 1.4 nm, from about 0.8 nm to about 1.3 nm, from about 0.8 nm to about 1.2 nm, from about 0.8 nm to about 1.1 nm, from about 0.8 nm to about 1 nm, from about 0.9 nm to about 1.4 nm, from about 0.9 nm to about 1.3 nm, from about 0.9 nm to about 1.2 nm, or from about 0.9 nm to about 1.1 nm. In some cases, the third BNNT monomer comprises an inner diameter of about 0.4 nm, about 0.45 nm, about 0.5 nm, about 0.55 nm, about 0.6 nm, about 0.65 nm, about 0.7 nm, about 0.75 nm, about 0.8 nm, about 0.84 nm, about 0.85 nm, about 0.86 nm, about 0.9 nm, about 0.95 nm, about 1 nm, about 1.05 nm, about 1.1 nm, about 1.15 nm, about 1.2 nm, about 1.25 nm, about 1.3 nm, about 1.35 nm, or about 1.4 nm.

In some embodiments, the BNNT trimer comprises a total inner diameter of from about 0.8 nm to about 2.8 nm, from about 0.8 nm to about 2.6 nm, from about 0.8 nm to about 2.5 nm, from about 0.8 nm to about 2.4 nm, from about 0.8 nm to about 2.2 nm, from about 0.8 nm to about 2 nm, from about 0.8 nm to about 1.8 nm, from about 0.8 nm to about 1.6 nm, from about 0.8 nm to about 1.4 nm, from about 1 nm to about 2.8 nm, from about 1 nm to about 2.6 nm, from about 1 nm to about 2.5 nm, from about 1 nm to about 2.4 nm, from about 1 nm to about 2.2 nm, from about 1 nm to about 2 nm, from about 1 nm to about 1.8 nm, from about 1 nm to about 1.6 nm, from about 1 nm to about 1.4 nm, from about 1.2 nm to about 2.8 nm, from about 1.2 nm to about 2.6 nm, from about 1.2 nm to about 2.5 nm, from about 1.2 nm to about 2.4 nm, from about 1.2 nm to about 2.2 nm, from about 1.2 nm to about 2 nm, from about 1.2 nm to about 1.8 nm, from about 1.2 nm to about 1.6 nm, from about 1.6 nm to about 2.8 nm, from about 1.6 nm to about 2.6 nm, from about 1.6 nm to about 2.5 nm, from about 1.6 nm to about 2.4 nm, from about 1.6 nm to about 2.2 nm, from about 1.6 nm to about 2 nm, or from about 1.6 nm to about 1.8 nm. In some cases, the total inner diameter is calculated as the sum of the inner diameter of the first BNNT monomer, the inner diameter of the second BNNT monomer, and the inner diameter of the third BNNT monomer.

In some instances, the one or more BNNT monomers have a nanotube length of from about 6 nm to about 30 nm. In some instances, the one or more BNNT monomers have a nanotube length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the first BNNT monomer has a nanotube length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the second BNNT monomer has a nanotube length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the third BNNT monomer has a nanotube length of from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm.

In some instances, the one or more BNNT monomers have a nanotube length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the first BNNT monomer has a nanotube length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the second BNNT monomer has a nanotube length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the third BNNT monomer has a nanotube length of about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, or about 30 nm.

In some instances, the lengths of the first BNNT monomer, the second BNNT monomer, and optionally the third BNNT monomer are substantially the same. As used herein, "substantially the same" in reference to length intends to be less than about 5%, or alternatively less than about 4%, less than about 3%, less than about 2%, or less than about 1% difference from a reference length. The reference length is, e.g., the first BNNT monomer, the second BNNT monomer, or optionally the third BNNT monomer.

In additional instances, the lengths of the first BNNT monomer, the second BNNT monomer, and optionally the third BNNT monomer are different, provided that the BNNT complex formed facilitate a fusion of the engineered lipid-based vesicle to a target cell.

In some embodiments, the engineered lipid-based vesicle comprises two or more BNNT complexes. In some cases, the engineered lip BNNT complexes, four or more BNNT complexes, five or more BNNT complexes, six or more BNNT complexes, seven or more BNNT complexes, or eight or more BNNT complexes. In some cases, each of the BNNT complexes do not interact or bind to another BNNT complex within the engineered lipid-based vesicle.

In some instances, the BNNT complex is a BNNT dimer. In such instances, the engineered lipid-based vesicle comprises two or more BNNT dimers, three or more BNNT dimers, four or more BNNT dimers, five or more BNNT dimers, six or more BNNT dimers, seven or more BNNT dimers, or eight or more BNNT dimers. In some cases, each of the BNNT dimers do not interact or bind to another BNNT dimer within the engineered lipid-based vesicle.

In some embodiments, a BNNT complex (e.g., BNNT dimer) described herein is a conjugated BNNT complex (e.g., BNNT dimer). In some instances, the conjugation is a terminal conjugation in which the end of the BNNTs are linked together. In some cases, the conjugation (e.g., the terminal conjugation) is a covalent conjugation. In other cases, the conjugation (e.g., the terminal conjugation) is a non-covalent conjugation.

In some instances, the terminal conjugation is located at the terminus that is within the lipid-based vesicle. In other instances, the terminal conjugation is located at the terminus that is outside of the lipid-based vesicle.

In some cases, the terminal conjugation is located at the carboxyl termini of the first BNNT and the second BNNT that form the BNNT dimer. In some cases, the terminal conjugation is located at the carboxyl termini of the first BNNT, the second BNNT, and the third BNNT monomer that form the BNNT trimer. In some cases, the conjugated carboxyl termini of the BNNT dimer or the BNNT trimer is located within the lipid-based vesicle. In additional cases, the conjugated carboxyl termini of the BNNT dimer or the BNNT trimer is located outside the lipid-based vesicle.

In some embodiments, the BNNT complex (e.g., BNNT dimer) is crosslinked at the termini which comprise one or more COOH groups. In some cases, the crosslinking chemistry involves a carbodiimide crosslinker that modifies the COOH group to generate a cross-linked complex. Exemplary carbodiimide crosslinkers include, but are not limited to, dicyclohexylcarbodiimide (DCC), N,N'-diisopropylcarbodiimide (DIC), 1-ethyl-3-(3-dimethylaminopropyl)carbodiimide (EDC), or 1-cyclohexyl-(2-morpholinoethyl)carbodiimide metho-p-toluene sulfonate (CMCT or CMC). In some cases, the BNNT complex is crosslinked via a carbodiimide crosslinker, optionally selected from dicyclohexylcarbodiimide (DCC), N,N'-diisopropylcarbodiimide (DIC), 1-ethyl-3-(3-dimethylaminopropyl)carbodiimide (EDC), or 1-cyclohexyl-(2-morpholinoethyl)carbodiimide metho-p-toluene sulfonate (CMCT or CMC). In some cases, the BNNT complex is crosslinked via EDC.

In some embodiments, the BNNT complex (e.g., BNNT dimer) is conjugated at the termini which comprise one or more COOH groups and the conjugation chemistry comprises a click chemistry. In some instances, the click chemistry comprises a 1,3-dipolar cycloaddition reaction comprising an azide and a phosphine. In some instances, the conjugation reaction is catalyzed by copper. In some instances, the conjugation reaction comprises reaction of an azide with a strained olefin, a strained alkyne, or a cycloalkyne such as OCT, DIFO, DIFBO, DIBO, BARAC, TMTH, or other strained cycloalkyne, the structures of which are shown in Gong, Y., Pan, L. Tett. Lett. 2015, 56, 2123. In some embodiments, the 1,3-dipolar cycloaddition reaction is catalyzed by light ("photoclick"). In some embodiments, the conjugation reaction comprises reaction of a terminal allyl group with a tetrazole and light or a terminal alkynyl group with a tetrazole and light.

In some embodiments, the BNNT complex (e.g., BNNT dimer) is further coated with an amphiphilic material. In some instances, the amphiphilic material comprises a phospholipid, a block copolymer, or a combination thereof. As used herein, a phospholipid is a natural phospholipid or a synthetic phospholipid. Exemplary natural phospholipids include, but are not limited to, phosphotidylcholine, phosphotidylserine, phosphotidylethanolamine, and phosphatidylinositol. Exemplary synthetic phospholipids include, but are not limited to, phosphatidic acid, phosphatidylcholine, phosphatidylglycerol, phosphatidylethanolamine, phosphatidylserine, and PEG phospholipid. Exemplary block copolymers include, but are not limited to, poly(ethylene oxide) (PEO)-poly(propylene oxide) (PPO) copolymer and PEO-PPO-PEO copolymer. In some instances, about 100%, 90%, 80%, 70%, 60%, 50%, 40%, or 30% of the BNNT complex is coated with the amphiphilic material.

Lipid-Based Vesicles

In some embodiments, the lipid-based vesicle is a liposome. Liposomes are artificially-prepared spherical vesicles that compose a lamellar phase lipid bilayer and an aqueous core. There are several types of liposomes, such as multilamellar vesicle (MLV or LMV), small unilamellar liposome vesicle (SUV), large unilamellar vesicle (LUV), giant unilamellar liposome (GUV), and the cochleate vesicle. SUV, LUV, and GUV are single lipid bilayer vesicles. MLVs comprise several lamellar phase lipid bilayers and have a size range of about 200 nm to about 3 μm in diameter. SUVs have a size range of from 20 nm to about 100 nm in diameter. LUVs have a size range of from about 100 nm to about 1000 nm in diameter. GUVs have a size range of from about 1 μm to about 200 μm in diameter. Cochleate vesicles are multilamellar cylinders in which the lamellae within the cylinder is folded in a spiral configuration. Cochleate vesicle has a diameter of about 100 nm or larger.

In some instances, the lipid-based vesicle (e.g., liposome) has a diameter across the major axis of the vesicle of at least about 28 nm, at least about 30 nm, at least about 35 nm, at least about 40 nm, at least about 50 nm, at least about 60 nm, at least about 70 nm, at least about 80 nm, at least about 90 nm, at least about 100 nm, at least about 150 nm, at least about 200 nm, at least about 300 nm, at least about 400 nm, at least about 500 nm, at least about 600 nm, at least about 700 nm, at least about 800 nm, at least about 900 nm, at least about 1000 nm, at least about 1200 nm, at least about 1500 nm, at least about 2000 nm, or larger. In some cases, the lipid-based vesicle (e.g., liposome) has a diameter across the major axis of the vesicle of at least about 28 nm or larger. In some cases, the lipid-based vesicle (e.g., liposome) has a diameter across the major axis of the vesicle of at least about 30 nm or larger. In some cases, the lipid-based vesicle (e.g., liposome) has a diameter across the major axis of the vesicle of at least about 35 nm or larger. In some cases, the lipid-based vesicle (e.g., liposome) has a diameter across the major axis of the vesicle of at least about 40 nm or larger. In some cases, the lipid-based vesicle (e.g., liposome) has a diameter across the major axis of the vesicle of at least about 50 nm or larger. In some cases, the lipid-based vesicle (e.g., liposome) has a diameter across the major axis of the vesicle of at least about 100 nm or larger. In some cases, the lipid-based vesicle (e.g., liposome) has a diameter across the major axis of the vesicle of at least about 200 nm or larger. In some cases, the lipid-based vesicle (e.g., liposome) has a diameter across the major axis of the vesicle of at least about 500 nm or larger. In some cases, the lipid-based vesicle (e.g., liposome) has a diameter across the major axis of the vesicle of at least about 1000 nm or larger.

In some instances, the liposome comprises a natural phospholipid, a synthetic phospholipid, an unsaturated lipid, a sphingolipid, a glycosphingolipid, a steroid, a charge-inducing lipid, or a combination thereof.

In some instances, the liposome comprises, or consists essentially of, or consists of, a natural phospholipid, a synthetic phospholipid, or a combination thereof. Exemplary natural phospholipids include, but are not limited to, phosphotidylcholine, phosphotidylserine, phosphotidylethanolamine, and phosphatidylinositol. Exemplary synthetic phospholipids include, but are not limited to, phosphatidic acid, phosphatidylcholine, phosphatidylglycerol, phosphatidylethanolamine, phosphatidylserine, and PEG phospholipid.

In some instances, the phosphatidic acid comprises 1,2-Dierucoyl-sn-glycero-3-phosphate (Sodium Salt) (DEPA-NA), 1,2-Dilauroyl-sn-glycero-3-phosphate (Sodium Salt) (DLPA-NA), 1,2-Dimyristoyl-sn-glycero-3-phosphate (Sodium Salt) (DMPA-NA), 1,2-Dioleoyl-sn-glycero-3-phosphate (Sodium Salt) (DOPA-NA), 1,2-Dipalmitoyl-sn-glycero-3-phosphate (Sodium Salt) (DPPA-NA), or 1,2-Distearoyl-sn-glycero-3-phosphate (Sodium Salt) (DSPA-NA).

In some instances, the phosphatidylcholine comprises 1,2-Didecanoyl-sn-glycero-3-phosphocholine (DDPC), 1,2-Dierucoyl-sn-glycero-3-phosphocholine (DEPC), 1,2-Dilinoleoyl-sn-glycero-3-phosphocholine (DLOPC), 1,2-Dilauroyl-sn-glycero-3-phosphocholine (DLPC), 1,2-Dimyristoyl-sn-glycero-3-phosphocholine (DMPC), 1,2-Dioleoyl-sn-glycero-3-phosphocholine (DOPC), 1,2-Dipalmitoyl-sn-glycero-3-phosphocholine (DPPC), 1,2-Distearoyl-sn-glycero-3-phosphocholine (DSPC), 1-Myristoyl-2-palmitoyl-sn-glycero 3-phosphocholine (Milk Sphingomyelin MPPC), 1-Myristoyl-2-stearoyl-sn-glycero-3-phosphocholine (MSPC), 1-Palmitoyl-2-myristoyl-sn-glycero-3-phosphocholine (PMPC), 1-Palmitoyl-2-oleoyl-sn-glycero-3-phosphocholine (POPC), 1-Palmitoyl-2-stearoyl-sn-glycero-3-phosphocholine (PSPC), 1-Stearoyl-2-myristoyl-sn-glycero-3-phosphocholine (SMPC), 1-Stearoyl-2-oleoyl-sn-glycero-3-phosphocholine (SOPC), or 1-Stearoyl-2-palmitoyl-sn-glycero-3-phosphocholine (SPPC).

In some instances, the phosphatidylcholine is a lysophosphatidylcholine. In some cases, the lysophosphatidylcholine comprises 1-Myristoyl-sn-glycero-3-phosphocholine (LYSOPC MYRISTIC), 1-Palmitoyl-sn-glycero-3-phosphocholine (LYSOPC PALMITIC), or 1-Stearoyl-sn-glycero-3-phosphocholine (LYSOPC STEARIC).

In some instances, the phosphatidylglycerol comprises 1,2-Dierucoyl-sn-glycero-3[Phospho-rac-(1-glycerol) (Sodium Salt) (DEPG-NA), 1,2-Dilauroyl-sn-glycero-3[Phospho-rac-(1-glycerol) (Sodium Salt) (DLPG-NA), 1,2-Dilauroyl-sn-glycero-3[Phospho-rac-(1-glycerol) (Ammonium Salt) (DLPG-NH4), 1,2-Dimyristoyl-sn-glycero-3[Phospho-rac-(1-glycerol) (Sodium Salt) (DMPG-NA), 1,2-Dimyristoyl-sn-glycero-3[Phospho-rac-(1-glycerol) (Ammonium Salt) (DMPG-NH4), 1,2-Dimyristoyl-sn-glycero-3[Phospho-rac-(1-glycerol) (Sodium/Ammonium Salt) (DMPG-NH4/NA), 1,2-Dioleoyl-sn-glycero-3[Phospho-rac-(1-glycerol) (Sodium Salt) (DOPG-NA), 1,2-Dipalmitoyl-sn-glycero-3[Phospho-rac-(1-glycerol) (Sodium Salt) (DPPG-NA), 1,2-Dipalmitoyl-sn-glycero-3[Phospho-rac-(1-glycerol) (Ammonium Salt) (DPPG-NH4), 1,2-Distearoyl-sn-glycero-3[Phospho-rac-(1-glycerol) (Sodium Salt) (DSPG-NA), 1,2-Distearoyl-sn-glycero-3[Phospho-rac-(1-glycerol) (Ammonium Salt) (DSPG-NH4), or 1-Palmitoyl-2-oleoyl-sn-glycero-3[Phospho-rac-(1-glycerol)] (Sodium Salt) (POPG-NA).

In some instances, the phosphatidylethanolamine comprises 1,2-Dierucoyl-sn-glycero-3-phosphoethanolamine (DEPE), 1,2-Dilauroyl-sn-glycero-3-phosphoethanolamine (DLPE), 1,2-Dimyristoyl-sn-glycero-3-phosphoethanolamine (DMPE), 1,2-Dioleoyl-sn-glycero-3-phosphoethanolamine (DOPE), 1,2-Dipalmitoyl-sn-glycero-3-phosphoethanolamine (DPPE), 1,2-Distearoyl-sn-glycero-3-phosphoethanolamine (DSPE), or 1-Palmitoyl-2-oleoyl-sn-glycero-3-phosphoethanolamine (POPE).

In some instances, the phosphatidylserine comprises 1,2-Dilauroyl-sn-glycero-3-phosphoserine (Sodium Salt) (DLPS-NA), 1,2-Dimyristoyl-sn-glycero-3-phosphoserine (Sodium Salt) (DMPS-NA), 1,2-Dioleoyl-sn-glycero-3-phosphoserine (Sodium Salt) (DOPS-NA), 1,2-Dipalmitoyl-sn-glycero-3-phosphoserine (Sodium Salt) (DPPS-NA), or 1,2-Distearoyl-sn-glycero-3-phosphoserine (Sodium Salt) (DSPS-NA).

In some instances, the PEG phospholipid comprises mPEG-phospholipid, polyglycerin-phospholipid, functionalized-phospholipid, or terminal activated-phospholipid.

In some embodiments, phospholipids are separated into those with diacylglyceride structures or those derived from phosphosphingolipids. In some embodiments, the diacylglyceride structures include phosphatidic acid (phosphatidate) (PA), phosphatidylethanolamine (cephalin) (PE), phosphatidylcholine (lecithin) (PC), phosphatidylserine (PS), and phosphoinositides such as phosphatidylinositol (PI), phosphatidylinositol phosphate (PIP), phosphatidylinositol bisphosphate (PIP2), and phosphatidylinositol triphosphate (PIP3). In some embodiments, phosphosphingolipids include ceramide phosphorylcholine, ceramide phosphorylethanolamine, and ceramide phosphoryllipid.

In some embodiments, the liposome comprises, or consists essentially of, or consists of, DEPA-NA, DLPA-NA, DMPA-NA, DOPA-NA, DPPA-NA, DSPA-NA, DEPE, DLPE, DMPE, DOPE, DPPE, DSPE, POPE, DLPS-NA, DMPS-NA, DOPS-NA, DPPS-NA, DSPS-NA, DDPC, DEPC, DLOPC, DLPC, DMPC, DOPC, DPPC, DSPC, LYSOPC MYRISTIC, LYSOPC PALMITIC, LYSOPC STEARIC, Milk Sphingomyelin MPPC, MSPC, PMPC, POPC, PSPC, SMPC, SOPC, SPPC, DEPG-NA, DLPG-NA, DLPG-NH4, DMPG-NA, DMPG-NH4, DMPG-NH4/NA, DOPG-NA, DPPG-NA, DPPG-NH4, DSPG-NA, DSPG-NH4, POPG-NA, HSPC, or a combination thereof.

In some instances, the liposome comprises, or consists essentially of, or consists of, diacylglycerol (DAG). In some cases, the diacylglycerol comprises, or consists essentially of, or consists of, triacylglycerol or glyceryl trioleate.

In some instances, the liposome comprises, or consists essentially of, or consists of, a saturated lipid. As used herein, the term "saturated" refers to lipid comprising carbon-carbon single bonds.

In some instances, the unsaturated lipid comprises 1-stearoyl-2-linoleoyl-sn-glycero-3-[phosphor-L-serine] or dioleaylphosphtidylcholine.

In some instances, the sphingolipid comprises sphingomyelin.

In some instances, the glycosphingolipid comprises ganglioside.

In some instances, the steroid comprises cholesterol or a cholesterol derivative, optionally DC-cholesterol.

In some instances, the charge-inducing lipid comprises diotadecyldimethyl ammonium bromide/chloride (DODAB/

C), dioleoyl trimethylammonium propane (DOTAP), or ionizable lipids (e.g., DLIN-MC3-DMA).

In some instances, the liposome comprises, or consists essentially of, or consists of, lysolipid. A lysolipid is a derivative of a lipid in which one or both acyl group has been removed by hydrolysis. In some instances, the lysolipid is a lysophospholipid. In other instances, the lysolipid is a lysoglycerophospholipid.

In some instances, the liposome comprises, or consists essentially of, or consists of, PEG-lipids. Exemplary PEG-lipids include, but are not limited to, DSPE-PEG(2000) succinyl, DSPE-PEG(5000) folate, DSPE-PEG(2000) maleimide, DSPE-PEG(2000)-TMS, 18:1 PE-PEG2000-benzylguanine, 8DSPE-PEG(2000)-DBCO, DPPE-PEG(2000) azide, DOPE-PEG(2000) azide, DOPE-PEG(2000) amine, or DOPE-PEG(2000)-HALO-TAG.

In some instances, the liposome comprises, or consists essentially of, or consists of, a lipid described in //cgmartini.nl/index.php/force-field-parameters/lipids.

In some embodiments, the lipids are selected based on its transition phase temperature (Tm), or the temperature interface between the liquid crystalline phase and the gel phase. In some embodiments, the Tm is governed by the head group species, hydrocarbone length, unsaturation, and the charge. For example, short lipids (lipids containing 8, 10, or 12 tail carbon chain length) have liquid crystalline phase at temperatures below 4° C. However, liposomes manufactured from these short chain carbon lipids are toxic to cells because they dissolve cell membranes. Liposomes manufactured from longer carbon-chain lipids are not toxic to cells, but their transition temperatures are higher. For example, 1,2-dipalmitoyl-sn-glycero-3-phosphocholine (DPPC) which has a 16 tail carbon length, has a Tm of about 41° C. In some embodiments, the lipids used herein have a Tm of between about 10° C. and about 37° C., 15° C. and about 30° C., 18° C. and about 27° C., or 21° C. and about 25° C. In some embodiments, the lipids used herein have a Tm of at least 22° C., 23° C., 24° C., or more. In some embodiments, the lipids used herein have a tail carbon length of at least about 12, 13, 14, or more.

In some embodiments, the lipids are selected based on the net charge of the liposome. In some embodiments, the liposome has a net charge of 0 at a pH of between about 4.0 and about 10.0, about 5.0 and about 9.0, about 6.5 and about 8.0, about 7.0 and about 7.8, or about 7.2 and about 7.6. In some embodiments, the liposome has a net charge of 0 at a pH of about 7.3, about 7.4, or about 7.5. In some embodiments, the liposome has a net positive charge at a pH of between about 4.0 and about 10.0, about 5.0 and about 9.0, about 6.5 and about 8.0, about 7.0 and about 7.8, or about 7.2 and about 7.6. In some embodiments, the liposome has a net positive charge at a pH of about 7.3, about 7.4, or about 7.5. In some embodiments, the liposome has a net negative charge at a pH of between about 4.0 and about 10.0, about 5.0 and about 9.0, about 6.5 and about 8.0, about 7.0 and about 7.8, or about 7.2 and about 7.6. In some embodiments, the liposome has a net negative charge at a pH of about 7.3, about 7.4, or about 7.5.

In some embodiments, the engineered lipid-based vesicle comprises, or consists essentially of, or consists of, one or more of the natural phospholipid, synthetic phospholipid, unsaturated lipid, sphingolipid, glycosphingolipid, steroid, saturated lipid, diacylglycerol, lysolipid, or charge-inducing lipid described supra. In some instances, the engineered lipid-based vesicle comprises a mixture of one or more natural or synthetic phospholipids. For example, the engineered lipid-based vesicle can comprise from about 10% to about 100% of one or more natural or synthetic phospholipids. The engineered lipid-based vesicle can comprise from about 10% to about 100%, from about 20% to about 100%, from about 50% to about 100%, from about 60% to about 80%, or from about 50% to about 70% of one or more phospholipids selected from DEPA-NA, DLPA-NA, DMPA-NA, DOPA-NA, DPPA-NA, DSPA-NA, DEPE, DLPE, DMPE, DOPE, DPPE, DSPE, POPE, DLPS-NA, DMPS-NA, DOPS-NA, DPPS-NA, DSPS-NA, DDPC, DEPC, DLOPC, DLPC, DMPC, DOPC, DPPC, DSPC, LYSOPC MYRISTIC, LYSOPC PALMITIC, LYSOPC STEARIC, Milk Sphingomyelin MPPC, MSPC, PMPC, POPC, PSPC, SMPC, SOPC, SPPC, DEPG-NA, DLPG-NA, DLPG-NH4, DMPG-NA, DMPG-NH4, DMPG-NH4/NA, DOPG-NA, DPPG-NA, DPPG-NH4, DSPG-NA, DSPG-NH4, HSPC, and POPG-NA. In some cases, the engineered lipid-based vesicle comprises about 10%, 20%, 30%, 40%, 50%, 60%, 70%, 80%, 90%, or 100% of one or more phospholipids selected from DEPA-NA, DLPA-NA, DMPA-NA, DOPA-NA, DPPA-NA, DSPA-NA, DEPE, DLPE, DMPE, DOPE, DPPE, DSPE, POPE, DLPS-NA, DMPS-NA, DOPS-NA, DPPS-NA, DSPS-NA, DDPC, DEPC, DLOPC, DLPC, DMPC, DOPC, DPPC, DSPC, LYSOPC MYRISTIC, LYSOPC PALMITIC, LYSOPC STEARIC, Milk Sphingomyelin MPPC, MSPC, PMPC, POPC, PSPC, SMPC, SOPC, SPPC, DEPG-NA, DLPG-NA, DLPG-NH4, DMPG-NA, DMPG-NH4, DMPG-NH4/NA, DOPG-NA, DPPG-NA, DPPG-NH4, DSPG-NA, DSPG-NH4, HSPC, and POPG-NA. In additional instances, the engineered lipid-based vesicle comprises about 10%, 20%, 30%, 40%, 50%, 60%, 70%, 80%, 90%, or 100% of a phospholipid selected from DEPA-NA, DLPA-NA, DMPA-NA, DOPA-NA, DPPA-NA, DSPA-NA, DEPE, DLPE, DMPE, DOPE, DPPE, DSPE, POPE, DLPS-NA, DMPS-NA, DOPS-NA, DPPS-NA, DSPS-NA, DDPC, DEPC, DLOPC, DLPC, DMPC, DOPC, DPPC, DSPC, LYSOPC MYRISTIC, LYSOPC PALMITIC, LYSOPC STEARIC, Milk Sphingomyelin MPPC, MSPC, PMPC, POPC, PSPC, SMPC, SOPC, SPPC, DEPG-NA, DLPG-NA, DLPG-NH4, DMPG-NA, DMPG-NH4, DMPG-NH4/NA, DOPG-NA, DPPG-NA, DPPG-NH4, DSPG-NA, DSPG-NH4, HSPC, and POPG-NA.

In some embodiments, the engineered lipid-based vesicle comprises, or consists essentially of, or consists of, a phospholipid-based liposome that further comprises, or consists essentially of, or consists of, one or more unsaturated lipids, sphingolipids, glycosphingolipids, steroids, or charge-inducing lipids. In some instances, the addition of one or more unsaturated lipids, sphingolipids, glycosphingolipids, steroids, or charge-inducing lipids aid in the fluidity of the liposome.

In some instances, the phospholipid-based liposome further comprises, or consists essentially of, or consists of, one or more steroids. In some cases, a ratio of the phospholipids to the steroids within the liposome is from about 100%:0% phospholipid:steroid to about 50%:50% phospholipid:steroid. In some cases, a ratio of the phospholipids to the steroids within the liposome is about 60%:40% phospholipid:steroid. In some cases, a ratio of the phospholipids to the steroids within the liposome is about 70%:30% phospholipid:steroid. In some cases, a ratio of the phospholipids to the steroids within the liposome is about 80%:20% phospholipid:steroid. In some cases, a ratio of the phospholipids to the steroids within the liposome is about 90%:10% phospholipid:steroid.

In some instances, the steroid is cholesterol or a cholesterol derivative (e.g., DC-chol or DC-cholesterol). In some cases, a ratio of the phospholipid to cholesterol or a cholesterol derivative with the liposome is from about 100%:0% phospholipid:cholesterol to about 50%:50% phospholipid:cholesterol. In some cases, a ratio of the phospholipids to cholesterol within the liposome is about 60%:40% phospholipid:cholesterol. In some cases, a ratio of the phospholipids to cholesterol within the liposome is about 70%:30% phospholipid:cholesterol. In some cases, a ratio of the phospholipids to cholesterol within the liposome is about 80%:20% phospholipid:cholesterol. In some cases, a ratio of the phospholipids to cholesterol within the liposome is about 90%:10% phospholipid:cholesterol.

In some embodiments, the phospholipids comprise, or consist essentially of, or consist of, DOPC. In some cases, a ratio of DOPC to cholesterol or a cholesterol derivative with the liposome is from about 100%:0% DOPC:cholesterol to about 50%:50% DOPC:cholesterol. In some cases, a ratio of DOPC to cholesterol within the liposome is about 60%:40% DOPC:cholesterol. In some cases, a ratio of DOPC to cholesterol within the liposome is about 70%:30% DOPC:cholesterol. In some cases, a ratio of DOPC to cholesterol within the liposome is about 80%:20% DOPC:cholesterol. In some cases, a ratio of DOPC to cholesterol within the liposome is about 90%:10% DOPC:cholesterol.

In some instances, the engineered lipid-based vesicle comprises, or consists essentially of, or consists of, one or more nanotube complexes (e.g., SWCNT dimers or BNNT dimers) per liposomal vesicle. As used herein, the number of the nanotube complexes (e.g., SWCNT dimers or BNNT dimers) per liposome is referred to as the "valency" of the engineered lipid-based vesicle. In some instances, the valency ranges from about 1 nanotube complex (e.g., SWCNT dimer or BNNT dimer) to 1 liposomal vesicle to about 100 nanotube complexes (e.g., SWCNT dimers or BNNT dimers) to 1 liposomal vesicle. In some instances, the valency ranges of nanotube to liposomal vesicle is from about 2:1 to about 100:1, from about 3:1 to about 100:1, from about 4:1 to about 100:1, from about 5:1 to about 100:1, from about 10:1 to about 100:1, from about 20:1 to about 100:1, from about 30:1 to about 100:1, from 50:1 to about 100:1, or from about 80:1 to about 100:1. In some cases, the valency of nanotube to liposomal vesicle is about 1:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, or about 100:1.

In some embodiments, the engineered lipid-based vesicle has a defined valency per surface area of the liposomal vesicle (also referred to herein as "density"). In such cases, the nanotube complex (e.g., SWCNT complex or dimer or BNNT complex or dimer) density per liposome is from about 1 nanotube complex or dimer (e.g., SWCNT complex or dimer or BNNT complex or dimer)/100 $nm^2$ to about 100 nanotube complexes or dimer (e.g., SWCNT complexes or dimers or BNNT complexes or dimers)/100 $nm^2$ of the surface area of the liposome. In some cases, the density is from about 2 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 3 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 5 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 10 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 20 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 30 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, or from about 50 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$ of the surface area of the liposome. In such cases, the nanotube complex or dimer (e.g., SWCNT complex or dimer or BNNT complex or dimer) density per liposome is about 1 nanotube complex or dimer (e.g., SWCNT complex or dimer or BNNT complex or dimer)/100 $nm^2$, about 2 nanotube complexes or dimers (e.g., SWCNT complexes or dimers or BNNT complexes or dimers)/100 $nm^2$, about 3 nanotube complexes or dimers (e.g., SWCNT complexes or dimers or BNNT complexes or dimers)/100 $nm^2$, about 4 nanotube complexes or dimers (e.g., SWCNT complexes or dimers or BNNT complexes or dimers)/100 $nm^2$, about 5 nanotube complexes or dimers (e.g., SWCNT complexes or dimers or BNNT complexes or dimers)/100 $nm^2$, about 6 nanotube complexes or dimers (e.g., SWCNT complexes or dimers or BNNT complexes or dimers)/100 $nm^2$, about 7 nanotube complexes or dimers (e.g., SWCNT complexes or dimers or BNNT complexes or dimers)/100 $nm^2$, about 8 nanotube complexes or dimers (e.g., SWCNT complexes or dimers or BNNT complexes or dimers)/100 $nm^2$, about 9 nanotube complexes or dimers (e.g., SWCNT complexes or dimers or BNNT complexes or dimers)/100 $nm^2$, about 10 nanotube complexes or dimers (e.g., SWCNT complexes or dimers or BNNT complexes or dimers)/100 $nm^2$, about 20 nanotube complexes or dimers (e.g., SWCNT complexes or dimers or BNNT complexes or dimers)/100 $nm^2$, about 30 nanotube complexes or dimers (e.g., SWCNT complexes or dimers or BNNT complexes or dimers)/100 $nm^2$, about 40 nanotube complexes or dimers (e.g., SWCNT complexes or dimers or BNNT complexes or dimers)/100 $nm^2$, about 50 nanotube complexes or dimers (e.g., SWCNT complexes or dimers or BNNT complexes or dimers)/100 $nm^2$, about 60 nanotube complexes or dimers (e.g., SWCNT complexes or dimers or BNNT complexes or dimers)/100 $nm^2$, about 70 nanotube complexes or dimers (e.g., SWCNT complexes or dimers or BNNT complexes or dimers)/100 $nm^2$, about 80 nanotube complexes or dimers (e.g., SWCNT complexes or dimers or BNNT complexes or dimers)/100 $nm^2$, about 90 nanotube complexes or dimers (e.g., SWCNT complexes or dimers or BNNT complexes or dimers)/100 $nm^2$, or about 100 nanotube complexes or dimers (e.g., SWCNT complexes or dimers or BNNT complexes or dimers)/100 $nm^2$ of the surface area of the liposome.

In some embodiments, the lipid-based vesicle is an extracellular vesicle (EV). In some instances, the extracellular vesicle is an exosome. Exosome is produced in the endosomal compartment of an eukaryotic cell and ranges in size from about 30 nm to about 150 nm in diameter. In some instances, the exosome has a diameter across the major axis of the vesicle of at least about 30 nm, at least about 40 nm, at least about 50 nm, at least about 60 nm, at least about 70 nm, at least about 80 nm, at least about 90 nm, at least about 100 nm, at least about 110 nm, at least about 120 nm, at least about 130 nm, or at least about 140 nm. In some instances, exosome comprises small molecules, therapeutics, proteins, lipids, and/or nucleic acids such as DNA and/or RNA molecules.

In some instances, the engineered lipid-based vesicle comprises, or consists essentially of, or consists of, one or more nanotube complexes (e.g., SWCNT complexes or dimers or BNNT complexes or dimers) per exosome. As used herein, the number of the nanotube complexes (e.g., SWCNT complexes or dimers or BNNT complexes or dimers) per exosome is referred to as the "valency" of the engineered lipid-based vesicle. In some instances, the valency ranges from about 1 nanotube complex or dimer (e.g., SWCNT complex or dimer or BNNT complex or dimer) to 1 exosome to about 100 nanotube complexes or dimers (e.g., SWCNT complexes or dimers or BNNT complexes or dimers) to 1 exosome. In some instances, the valency ranges of nanotube to exosome is from about 2:1 to about 100:1, from about 3:1 to about 100:1, from about 4:1 to about 100:1, from about 5:1 to about 100:1, from about 10:1 to about 100:1, from about 20:1 to about 100:1, from about 30:1 to about 100:1, from 50:1 to about 100:1, or from about 80:1 to about 100:1. In some cases, the valency of nanotube to exosome is about 1:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, or about 100:1.

In some embodiments, the engineered lipid-based vesicle has a defined valency per surface area of the exosome (also referred to herein as "density"). In such cases, the nanotube complex or dimer (e.g., SWCNT complex or dimer or BNNT complex or dimer) density per exosome is from about 1 nanotube complex or dimer (e.g., SWCNT complex or dimer or BNNT complex or dimer)/100 nm$^2$ to about 100 nanotube complexes or dimers (e.g., SWCNT complexes or dimers or BNNT complexes or dimers)/100 nm$^2$ of the surface area of the exosome. In some cases, the density is from about 2 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$, from about 3 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$, from about 5 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$, from about 10 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$, from about 20 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$, from about 30 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$, or from about 50 nanotube complexes or dimers (e.g., SWCNT complexes or dimers or BNNT complexes or dimers)/100 nm$^2$ to about 100 nanotube complexes or dimers (e.g., SWCNT complexes or dimers or BNNT complexes or dimers)/100 nm$^2$ of the surface area of the exosome. In such cases, the nanotube complex or dimer (e.g., SWCNT complex or dimer or BNNT complex or dimer) density per exosome is about 1 nanotube complex or dimer (e.g., SWCNT complex or dimer or BNNT complex or dimer)/100 nm$^2$, about 2 nanotube complexes or dimers (e.g., SWCNT complexes or dimers or BNNT complexes or dimers)/100 nm$^2$, about 3 nanotube complexes or dimers (e.g., SWCNT complexes or dimers or BNNT complexes or dimers)/100 nm$^2$, about 4 nanotube complexes or dimers (e.g., SWCNT complexes or dimers or BNNT complexes or dimers)/100 nm$^2$, about 5 nanotube complexes or dimers (e.g., SWCNT complexes or dimers or BNNT complexes or dimers)/100 nm$^2$, about 6 nanotube complexes or dimers (e.g., SWCNT complexes or dimers or BNNT complexes or dimers)/100 nm$^2$, about 7 nanotube complexes or dimers (e.g., SWCNT complexes or dimers or BNNT complexes or dimers)/100 nm$^2$, about 8 nanotube complexes or dimers (e.g., SWCNT complexes or dimers or BNNT complexes or dimers)/100 nm$^2$, about 9 nanotube complexes or dimers (e.g., SWCNT complexes or dimers or BNNT complexes or dimers)/100 nm$^2$, about 10 nanotube complexes or dimers (e.g., SWCNT complexes or dimers or BNNT complexes or dimers)/100 nm$^2$, about 20 nanotube complexes or dimers (e.g., SWCNT complexes or dimers or BNNT complexes or dimers)/100 nm$^2$, about 30 nanotube complexes or dimers (e.g., SWCNT complexes or dimers or BNNT complexes or dimers)/100 nm$^2$, about 40 nanotube complexes or dimers (e.g., SWCNT complexes or dimers or BNNT complexes or dimers)/100 nm$^2$, about 50 nanotube complexes or dimers (e.g., SWCNT complexes or dimers or BNNT complexes or dimers)/100 nm$^2$, about 60 nanotube complexes or dimers (e.g., SWCNT complexes or dimers or BNNT complexes or dimers)/100 nm$^2$, about 70 nanotube complexes or dimers (e.g., SWCNT complexes or dimers or BNNT complexes or dimers)/100 nm$^2$, about 80 nanotube complexes or dimers (e.g., SWCNT complexes or dimers or BNNT complexes or dimers)/100 nm$^2$, about 90 nanotube complexes or dimers (e.g., SWCNT complexes or dimers or BNNT complexes or dimers)/100 nm$^2$, or about 100 nanotube complexes or dimers (e.g., SWCNT complexes or dimers or BNNT complexes or dimers)/100 nm$^2$ of the surface area of the exosome.

In some embodiments, the extracellular vesicle is a microvesicle (also referred to as ectosome or microparticle). Microvesicle is released from a cell membrane and can range in size from about 30 nm to about 1000 nm in diameter. In some instances, the microvesicle has a diameter across the major axis of the vesicle of at least about 30 nm, at least about 40 nm, at least about 50 nm, at least about 60 nm, at least about 70 nm, at least about 80 nm, at least about 90 nm, at least about 100 nm, at least about 110 nm, at least about 120 nm, at least about 130 nm, at least about 140 nm, at least about 150 nm, at least about 200 nm, at least about 300 nm, at least about 400 nm, at least about 500 nm, at least about 600 nm, at least about 700 nm, at least about 800 nm, or at least about 900 nm. In some cases, microvesicle comprises small molecules, therapeutics, proteins, lipids, and/or nucleic acids such as DNA and/or RNA molecules.

In some instances, the engineered lipid-based vesicle comprises, or consists essentially of, or consists of, one or more nanotube complexes (e.g., SWCNT complexes or dimers or BNNT complexes or dimers) per microvesicle. As used herein, the number of the nanotube complexes or dimers (e.g., SWCNT complexes or dimers or BNNT complexes or dimers) per microvesicle is referred to as the "valency" of the engineered lipid-based vesicle. In some instances, the valency ranges from about 1 nanotube complex or dimer (e.g., SWCNT complex or dimer or BNNT complex or dimer) to 1 microvesicle to about 100 nanotube complexes or dimers (e.g., SWCNT complexes or dimers or BNNT complexes or dimers) to 1 microvesicle. In some instances, the valency ranges of nanotube to microvesicle is from about 2:1 to about 100:1, from about 3:1 to about 100:1, from about 4:1 to about 100:1, from about 5:1 to about 100:1, from about 10:1 to about 100:1, from about 20:1 to about 100:1, from about 30:1 to about 100:1, from 50:1 to about 100:1, or from about 80:1 to about 100:1. In some cases, the valency of nanotube to microvesicle is about 1:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, or about 100:1.

In some embodiments, the engineered lipid-based vesicle has a defined valency per surface area of the microvesicle (also referred to herein as "density"). In such cases, the nanotube complex or dimer (e.g., SWCNT complex or dimer or BNNT complex or dimer) density per microvesicle is from about 1 nanotube complex or dimer (e.g., SWCNT complex or dimer or BNNT complex or dimer)/100 $nm^2$ to about 100 nanotube complexes or dimers (e.g., SWCNT complexes or dimers or BNNT complexes or dimers)/100 $nm^2$ of the surface area of the microvesicle. In some cases, the density is from about 2 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 3 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 5 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 10 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 20 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, from about 30 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$, or from about 50 nanotube complexes or dimers (e.g., SWCNT complexes or dimers or BNNT complexes or dimers)/100 $nm^2$ to about 100 nanotube complexes or dimers (e.g., SWCNT complexes or dimers or BNNT complexes or dimers)/100 $nm^2$ of the surface area of the microvesicle. In such cases, the nanotube complex or dimer (e.g., SWCNT complex or dimer or BNNT complex or dimer) density per microvesicle is about 1 nanotube complex or dimer (e.g., SWCNT complex or dimer or BNNT complex or dimer)/100 $nm^2$, about 2 nanotube complexes or dimers (e.g., SWCNT complexes or dimers or BNNT complexes or dimers)/100 $nm^2$, about 3 nanotube complexes or dimers (e.g., SWCNT complexes or dimers or BNNT complexes or dimers)/100 $nm^2$, about 4 nanotube complexes or dimers (e.g., SWCNT complexes or dimers or BNNT complexes or dimers)/100 $nm^2$, about 5 nanotube complexes or dimers (e.g., SWCNT complexes or dimers or BNNT complexes or dimers)/100 $nm^2$, about 6 nanotube complexes or dimers (e.g., SWCNT complexes or dimers or BNNT complexes or dimers)/100 $nm^2$, about 7 nanotube complexes or dimers (e.g., SWCNT complexes or dimers or BNNT complexes or dimers)/100 $nm^2$, about 8 nanotube complexes or dimers (e.g., SWCNT complexes or dimers or BNNT complexes or dimers)/100 $nm^2$, about 9 nanotube complexes or dimers (e.g., SWCNT complexes or dimers or BNNT complexes or dimers)/100 $nm^2$, about 10 nanotube complexes or dimers (e.g., SWCNT complexes or dimers or BNNT complexes or dimers)/100 $nm^2$, about 20 nanotube complexes or dimers (e.g., SWCNT complexes or dimers or BNNT complexes or dimers)/100 $nm^2$, about 30 nanotube complexes or dimers (e.g., SWCNT complexes or dimers or BNNT complexes or dimers)/100 $nm^2$, about 40 nanotube complexes or dimers (e.g., SWCNT complexes or dimers or BNNT complexes or dimers)/100 $nm^2$, about 50 nanotube complexes or dimers (e.g., SWCNT complexes or dimers or BNNT complexes or dimers)/100 $nm^2$, about 60 nanotube complexes or dimers (e.g., SWCNT complexes or dimers or BNNT complexes or dimers)/100 $nm^2$, about 70 nanotube complexes or dimers (e.g., SWCNT complexes or dimers or BNNT complexes or dimers)/100 $nm^2$, about 80 nanotube complexes or dimers (e.g., SWCNT complexes or dimers or BNNT complexes or dimers)/100 $nm^2$, about 90 nanotube complexes or dimers (e.g., SWCNT complexes or dimers or BNNT complexes or dimers)/100 $nm^2$, or about 100 nanotube complexes or dimers (e.g., SWCNT complexes or dimers or BNNT complexes or dimers)/100 $nm^2$ of the surface area of the microvesicle.

Target-Binding Moieties

In some embodiments, an engineered lipid-based vesicle described herein further comprises a target-binding moiety. In some instances, the target-binding moiety is conjugated to the surface of the lipid-based vesicle, optionally with a linker. In other instances, the target-binding moiety comprises a transmembrane domain which is embedded within the lipid-based vesicle. In some cases, the linker is a hydrophobic linker, a hydrophilic linker, a pH sensitive linker, a cleavable linker (e.g., a chemically cleavable linker or an enzymatically cleavable linker), or a non-cleavable linker. In some cases, the linker comprises a polypeptide, for example, of at least 5, 10, 15, 20, 30, 50, or more amino acid residues in length. In some cases, the linker comprises a poly-Ala linker, a poly-Gly linker, or a series of Ala and Gly residues. In some cases, the linker comprises a (Gly4Ala)n linker in which n is an integer from about 1 to about 10, from about 1 to about 5, or from about 1 to about 3. In some cases, the linker is a polymeric linker (e.g., a polyethylene glycol linker).

In some embodiments, the target-binding moiety recognizes a surface receptor of a target. In some instances, the target is a target cell. In some cases, the target cell is a cancer cell. In some cases, the surface receptor is present on the cancer cell. In some cases, the surface receptor present on the cancer cell is a tumor-associated antigen. Exemplary tumor-associated antigens include, but are not limited to, alphafetoprotein (AFP), carcinoembryonic antigen (CEA), CA-125, MUC-1, epithelial tumor antigen (ETA), tyrosinase, melanoma-associated antigen (MAGE), RAS, p53, HER2, EpCAM, and PSMA.

In some embodiments, the target-binding moiety recognizes a surface receptor of an immune cell. As used herein, the term "immune cells" includes, e.g., white blood cells (leukocytes) that are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3, including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

The term "effector T cells", as used herein, refers to T cells that can specifically bind an antigen and mediate an immune response (effector function) without the need for further differentiation. Examples of effector T cells include CTLs, TH1 cells, TH2 cells, effector memory cells and T helper cells. In contrast to effector T cells, naïve T cells have not encountered their specific antigen:MHC complex, nor responded to it by proliferation and differentiation into an effector T cell. Effector T cells can be resting (in the G0 phase of the cell cycle) or activated (proliferating).

The term "anti-inflammatory T cell" refers to a T cell that promotes an anti-inflammatory response. The anti-inflammatory function of the T cell may be accomplished through production and/or secretion of anti-inflammatory proteins, cytokines, chemokines, and the like. Anti-inflammatory proteins are also intended to encompass anti-proliferative signals that suppress immune responses. Anti-inflammatory proteins include IL-4, IL-10, IL-13, IL-21, IL-23, IL-27, IFN-α, TGF-β, IL-1ra, G-CSF, and soluble receptors for TNF and IL-6.

In some cases, the target-binding moiety recognizes a surface receptor of a T-cell lymphocyte, a B-cell lymphocyte, a Nature Killer (NK) cell, a neutrophil, a monocyte, a macrophage, or a dendritic cell. In some cases, the target-binding moiety recognizes a surface receptor of a T-cell lymphocyte, a B-cell lymphocyte, a Nature Killer (NK) cell, a macrophage, or a dendritic cell. In some cases, exemplary immune cell receptors include, but are not limited to, CD3 and CD19.

In some instances, the target-binding moiety recognizes a surface receptor that activates an immune checkpoint pathway. In some cases, the surface receptor is located on a cancer cell and include, for example, PD-L1, PD-L2, CD80, CD86, B7RP1, B7-H3, HVEM, CD137L, OX40L, CD70, CD40, GAL9, or a MHC class I or II receptor. In some cases, the surface receptor is located on a T cell and include, for example, PD1, CD28, CTLA4, ICOS, BTLA, KIR, TCR, LAG3, CD137, OX40, CD27, CD40L, TIM3, and A2aR.

In some embodiments, the target-binding moiety recognizes a surface protein of a viral particle. In some cases, the virus is a DNA virus or an RNA virus. The DNA viruses include single-stranded (ss) DNA viruses, double-stranded (ds) DNA viruses, or DNA viruses that contain both ss and ds DNA regions. The RNA viruses include single-stranded (ss) RNA viruses or double-stranded (ds) RNA viruses. In some cases, the ssRNA viruses are further classified into positive-sense RNA viruses or negative-sense RNA viruses.

Payloads

In some embodiments, an engineered lipid-based vesicle further comprises, or consists essentially of, or consists of, a payload. In some instances, the payload is a small molecule, a protein, a polypeptide, a nucleic acid molecule, a protein conjugate, a polypeptide conjugate, a nucleic acid conjugate, a polymer (e.g., a polymer conjugate), a gene-editing system, or a vaccine. In some instances, the payload is an antitumor agent, an antimicrobial agent, a contrast agent, an antioxidant, or an anti-inflammatory agent. In some instances, the payload is an enzyme inhibitor, a receptor antagonist, a receptor agonist, an opioid, a steroid, a calcium channel blocker, a beta blocker, an angiotensin II receptor blocker, a diuretic, an antidepressant, an analgesic, a stimulant, a hormone, an enzyme, an antihypertensive drug, an anticonvulsant, a nonsteroidal anti-inflammatory drug, an anticoagulant, an antibiotic, an antiviral drug, an antifungal drug, or an antihistamine.

In some instances, the payload comprises a first-line therapy. As used herein, "first-line therapy" comprises a primary treatment for a subject, optionally a subject with a cancer. In some instances under a cancer setting, the cancer is a primary cancer. In other instances, the cancer is a metastatic or recurrent cancer. In some cases, the first-line therapy comprises chemotherapy. In other cases, the first-line treatment comprises radiation therapy. A skilled artisan would readily understand that different first-line treatments may be applicable to different type of cancers.

In some cases, the payload comprises a second-line therapy, a third-line therapy, a fourth-line therapy, or a fifth-line therapy, optionally under a cancer setting. As used herein, a second-line therapy encompasses treatments that are utilized after the primary or first-line treatment stops. A third-line therapy, a fourth-line therapy, or a fifth-line therapy encompass subsequent treatments. As indicated by the naming convention, a third-line therapy encompass a treatment course upon which a primary and second-line therapy have stopped.

In some instances, the payload is a chemotherapeutic agent, an immunotherapeutic agent, a monoclonal antibody, or an antibody-drug conjugate. Exemplary payloads include, but are not limited to, alkylating agents such as altretamine, busulfan, carboplatin, carmustine, chlorambucil, cisplatin, cyclophosphamide, dacarbazine, lomustine, melphalan, oxaliplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin (DOX), epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone. In some cases, the payload comprises doxorubicin (DOX).

In some instances, the payload comprises, or consists essentially of, or consists of, an immune checkpoint modulator. Exemplary checkpoint modulators include pembrolizumab, nivolumab, tremelimumab, or ipilimumab. In some instances, the payload comprises a modulator of PD-L1, PD-1, CTLA-4, LAG3, B7-H3, KIR, CD137, PS, TFM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some instances, the payload comprises, or consists essentially of, or consists of, an inhibitor of the enzyme poly ADP ribose polymerase (PARP). Exemplary PARP inhibitors include, but are not limited to, olaparib (AZD-2281, Lynparza®, from Astra Zeneca), rucaparib (PF-01367338, Rubraca®, from Clovis Oncology), niraparib (MK-4827, Zejula®, from Tesaro), talazoparib (BMN-673, from BioMarin Pharmaceutical Inc.), veliparib (ABT-888, from Abb Vie), CK-102 (formerly CEP 9722, from Teva Pharmaceutical Industries Ltd.), E7016 (from Eisai), iniparib (BSI 201, from Sanofi), and pamiparib (BGB-290, from BeiGene).

In some cases, the payload comprises, or consists essentially of, or consists of, a cytokine. Exemplary cytokines include, but are not limited to, IL-Iβ, IL-6, IL-7, IL-10, IL-12, IL-15, IL-21, or TNFα.

In some embodiments, the payload comprises, or consists essentially of, or consists of, a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2p, CFA, or Flagellin.

In some instances, the payload comprises, or consists essentially of, or consists of, an antibiotic or an antiviral therapeutic agent. Exemplary antibiotics and antiviral therapeutic agents include, but are not limited to, acyclovir, brivudine, docosanol, famciclovir, foscarnet, idoxuridine, penciclovir, trifluridine, valacyclovir, and pritelivir.

In some instances, the payload comprises, or consists essentially of, or consists of, a therapeutic agent for the treatment of an autoimmune disease or disorder. In some cases, exemplary payloads include, but are not limited to, corticosteroids such as prednisone, budesonide, or prednisolone; calcineurin inhibitors such as cyclosporine or tacrolimus; mTOR inhibitors such as sirolimus or everolimus; EVIDH inhibitors such as azathioprine, leflunomide, or mycophenolate; biologics such as abatacept, adalimumab, anakinra, certolizumab, etanercept, golimumab, infliximab, ixekizumab, natalizumab, rituximab, secukinumab, tocilizumab, ustekinumab, or vedolizumab; and monoclonal antibodies such as basiliximab, daclizumab, or muromonab.

In some instances, the payload comprises, or consists essentially of, or consists of, a therapeutic agent for the treatment of an inflammatory condition. In some cases, the payload comprises nonsteroidal anti-inflammatory drugs (NSAIDs) such as aspirin, celecoxib, diclofenac, diflunisal, etodolac, ibuprofen, indomethacin, ketoprofen, ketorolac, nabumetone, naproxen, oxaprozin, piroxicam, salsalate, sulindac, or tolmetin; and corticosteroids such as prednisone.

In some instances, the payload comprises, or consists essentially of, or consists of, a gene-editing system. Exemplary gene-editing system include Clustered Regularly Interspaced Short Palindromic Repeats (CRISPR) system, zinc-finger nuclease (ZFN) system, and transcription activator-like effector nuclease (TALEN) system.

In some embodiments, the gene editing system is a CRISPR/Cas system. Any suitable CRISPR/Cas system may be contemplated for delivery by an engineered lipid-based vesicle disclosed herein. The CRISPR/Cas system may be referred to using a variety of naming systems. Exemplary naming systems are provided in Makarova, K. S. et al, "An updated evolutionary classification of CRISPR-Cas systems," Nat Rev Microbiol (2015) 13:722-736 and Shmakov, S. et al, "Discovery and Functional Characterization of Diverse Class 2 CRISPR-Cas Systems," Mol Cell (2015) 60: 1-13. The CRISPR/Cas system may be a type I, a type II, a type III, a type IV, a type V, a type VI system, or any other suitable CRISPR/Cas system. The CRISPR/Cas system as used herein may be a Class 1, Class 2, or any other suitably classified CRISPR/Cas system. The Class 1 CRISPR/Cas system may use a complex of multiple Cas proteins to effect regulation. The Class 1 CRISPR/Cas system may comprise, for example, type I (e.g., I, IA, IB, IC, ID, IE, IF, IU), type III (e.g., Ill, IIIA, IIIB, IIIC, HID), and type IV (e.g., IV, IVA, IVB) CRISPR/Cas type. The Class 2 CRISPR/Cas system may use a single large Cas protein to effect regulation. The Class 2 CRISPR/Cas systems may comprise, for example, type II (e.g., II, IIA, IIB) and type V CRISPR/Cas type. CRISPR systems may be complementary to each other, and/or can lend functional units in trans to facilitate CRISPR locus targeting. [0074] The Cas protein may be a type I, type II, type III, type IV, type V, or type VI Cas protein. The Cas protein may comprise one or more domains. Non-limiting examples of domains include, a guide nucleic acid recognition and/or binding domain, nuclease domains (e.g., DNase or RNase domains, RuvC, HNH), DNA binding domain, RNA binding domain, helicase domains, protein-protein interaction domains, and dimerization domains. The guide nucleic acid recognition and/or binding domain may interact with a guide nucleic acid. The nuclease domain may comprise catalytic activity for nucleic acid cleavage. The nuclease domain may lack catalytic activity to prevent nucleic acid cleavage. The Cas protein may be a chimeric Cas protein that is fused to other proteins or polypeptides. The Cas protein may be a chimera of various Cas proteins, for example, comprising domains from different Cas proteins.

Non-limiting examples of Cas proteins include c2c1, C2c2, c2c3, Cas1, Cas1B, Cas2, Cas3, Cas4, Cas5, Cas5e (CasD), Cas6, Cas6e, Cas6f, Cas7, Cas8a, Cas8a1, Cas8a2, Cas8b, Cas8c, Cas9 (Csn1 or Csx12), Cas 10, Cas1Od, Cas1O, Cas1Od, CasF, CasG, CasH, Cpf1, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx7, Csx14, Csx1O, Csx16, CsaX, Csx3, Csx1, Csx15, Csf1, Csf2, Csf3, Csf4, and Cu966, and homologs or modified versions thereof.

The Cas protein may be from any suitable organism. Non-limiting examples include *Streptococcus pyogenes, Streptococcus thermophilus, Streptococcus* sp., *Staphylococcus aureus, Nocardiopsis dassonvillei, Streptomyces pristinae spiralis, Streptomyces viridochromo* genes, *Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Pseudomonas aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxi-*

*dans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Leptotrichia shahii,* and *Francisella novicida.* In some aspects, the organism is *Streptococcus pyogenes (S. pyogenes).* In some aspects, the organism is *Staphylococcus aureus (S. aureus).* In some aspects, the organism is *Streptococcus thermophilus (S. thermophilus).*

In some instances, the Cas protein and the guide RNA are delivered by the engineered lipid-based vesicle in a vector format, e.g., as a single vector comprising one or more promoters, or as two or more vectors. In some instances, the vector is a viral vector. Exemplary viral vectors include, but are not limited to, vectors based on or derived from vaccinia virus, poliovirus, adenovirus, adeno-associated virus, SV40, herpes simplex virus, human immunodeficiency virus, a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In some cases, the vector is a non-viral vector, and include, for example, pXT1, pSG5, pSVK3, pBPV, pMSG, and pSVLSV40.

In some cases, the Cas protein and the guide RNA are formulated as a protein-RNA complex prior to encapsulating into the engineered lipid-based vesicle.

In some embodiments, the gene editing system is a zinc-finger nuclease (ZFN) system. Zinc-finger nuclease is an engineered restriction enzyme generated by fusing a zinc finger DNA-binding domain to a DNA-cleavage domain. In some instances, the ZFN is delivered by the engineered lipid-based vesicle in a vector format. In some instances, the vector is a viral vector. Exemplary viral vectors include, but are not limited to, vectors based on or derived from vaccinia virus, poliovirus, adenovirus, adeno-associated virus, SV40, herpes simplex virus, human immunodeficiency virus, a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In some cases, the vector is a non-viral vector, and include, for example, pXT1, pSG5, pSVK3, pBPV, pMSG, and pSVLSV40. In other instances, the ZFN is delivered by the engineered lipid-based vesicle as a protein complex.

In some embodiments, the gene editing system is a transcription activator-like effector nuclease (TALEN) system. Transcription activator-like effector nuclease is an engineered restriction enzyme generated by fusing a TAL effector DNA-binding domain to a DNA cleavage domain. In some instances, TALEN is delivered by the engineered lipid-based vesicle in a vector format. In some instances, the vector is a viral vector. Exemplary viral vectors include, but are not limited to, vectors based on or derived from vaccinia virus, poliovirus, adenovirus, adeno-associated virus, SV40, herpes simplex virus, human immunodeficiency virus, a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In some cases, the vector is a non-viral vector, and include, for example, pXT1, pSG5, pSVK3, pBPV, pMSG, and pSVLSV40. In other instances, TALEN is delivered by the engineered lipid-based vesicle as a protein complex.

In some embodiments, the gene editing system (e.g., the CRISPR system, the ZFN system, or the TALEN system) is utilized to modulate a target associated with a disease or condition. In some instances, an expression level of the target (e.g., either at an mRNA level or at a protein level) is decreased to treat a disease or condition. In some instances, an expression level of the target (e.g., either at an mRNA level or at a protein level) is increased to treat a disease or condition. Exemplary targets include, but are not limited to, DMD, HTT, FGFR3, SOD1, PCSK9, TTR, IL2RG, HIV (e.g., CCR5), and HBV. Exemplary diseases or conditions of which the gene editing system can be applicable include, but are not limited to, a muscular dystrophy such as Duchenne muscular dystrophy (DMD) and Becker muscular dystrophy (BMD), hemophilia B, HIV, HBV, SCID, cataract, cystic fibrosis, and hereditary tyrosinemia.

In some embodiments, the payload comprises, or consists essentially of, or consists of, a contrasting agent. In some instances, the contrasting agent is a dye. In some cases, the dye is a fluorescent dye (e.g., a fluorophore). Exemplary dyes include, but are not limited to, hydroxycoumarin, aminocoumarin, methoxycoumarin, *Lucifer* yellow, Cy2, Cy3, Cy3B, Cy3.5, Cy5, Cy5.5, Cy7, FluorX, Fluorescein, BODIPY-FL, and Texas Red.

In some embodiments, the payload comprises, or consists essentially of, or consists of, a mRNA. In some instances, the mRNA encodes one or more proteins of interest, e.g., for use in vaccination, protein replacement therapy, or treatment of genetic disease. In some instances, the mRNA is a monocistronic mRNA, a bicistronic mRNA, or a polycistronic mRNA. In some instances, the mRNA encodes a protein of interest that is foreign to the host for which an immune response canbeinduced.

In some embodiments, the payload comprises, or consists essentially of, or consists of, a vaccine. In some instances, the vaccine comprises a vector vaccine, e.g., comprising one or more vectors (e.g., viral or non-viral vector) that encodes one or more proteins for inducing an immune response. In some instances, the vaccine comprises a protein subunit vaccine, e.g., a recombinant wild-type or mutant protein or more than one recombinant protein for inducing an immune response. In additional instances, the vaccine comprises a messenger RNA (mRNA) vaccine, in which the mRNA encodes one or more proteins for inducing an immune response.

In some embodiments, the payload comprises, or consists essentially of, or consists of, a self-amplifying mRNA (SAM) vaccine. In some instances, the SAM vaccine utilizes an alphavirus genome. In some cases, the SAM vaccine encodes one or more proteins from human cytomegalovirus (CMV), hepatitis (e.g., hepatitis C) virus, rabies virus, HIV-1 virus, Ebola virus, influenza virus, Zika virus, or severe acute respiratory syndrome coronavirus 2 (SARS-CoV-2).

In some embodiments, the payload comprises, or consists essentially of, or consists of, two or more, three or more, or four or more, five or more, six or more, seven or more, eight or more, nine or more, or ten or more therapeutic agents described supra. In some instances, the payload comprises two or more, three or more, four or more, or five or more therapeutic agents described supra. In some instances, the payload comprises two or more, three or more, or four or more therapeutic agents described supra.

In some embodiments, the payload comprises, or consists essentially of, or consists of, two or more, three or more, or four or more, five or more, six or more, seven or more, eight or more, nine or more, or ten or more different therapeutic agents described supra. In some instances, the payload comprises two or more, three or more, four or more, or five or more different therapeutic agents described supra. In some instances, the payload comprises two or more, three or more, or four or more different therapeutic agents described supra.

In some embodiments, the payload comprises, or consists essentially of, or consists of, two or more, three or more, or four or more, five or more, six or more, seven or more, eight or more, nine or more, or ten or more therapeutic agents described supra in which the therapeutic agents are the same. In some instances, the payload comprises two or more, three or more, four or more, or five or more therapeutic agents described supra in which the therapeutic agents are the same. In some instances, the payload comprises two or more, three or more, or four or more therapeutic agents described supra in which the therapeutic agents are the same.

Engineered Lipid-Based Vesicles and Compositions

In some embodiments, described herein is an engineered lipid-based vesicle as described herein that facilitates a decreased toxicity to a target cell. In some embodiments, the engineered lipid-based vesicle further facilitates an increase in payload delivery to a target cell. In some instances, the engineered lipid-based vesicle comprises a nanotube complex (e.g., a SWCNT complex or a BNNT complex) that facilitates a distortion of lipids that comprise the lipid-based vesicle and thereby facilitates fusion of the lipids with a lipid membrane of a target cell. In additional instances, the engineered lipid-based vesicle comprises a BNNT complex that facilitates a distortion of lipids that comprise the lipid-based vesicle and thereby facilitates fusion of the lipids with a lipid membrane of a target cell.

In some embodiments, described herein is a composition comprising an engineered lipid-based vesicle as described herein and an excipient. In some instances, the excipient is a pharmaceutically acceptable excipient. In some cases, the composition is formulated for systemic administration. In other cases, the composition is formulated for local administration. In some cases, the composition is formulated for parenteral administration, for example, but not limited to, subcutaneous, intravenous, intraperitoneal, intradermal, or intramuscular administration.

Methods of Use

In certain embodiments, disclosed herein is a method of treating a disease or condition by administering to a subject an engineered lipid-based vesicle described herein that optionally comprises a payload selected to treat the disease or condition. In some instances, the disease or condition is a cancer, a pathogenic infection, an autoimmune disease or condition, or an inflammatory condition. As is apparent to the skilled artisan, the methods can also be practiced in vitro and used as an assay to test the therapy prior to clinical use. In this embodiment, the cells are cultured in the presence of the engineered vesicles and subsequently monitored for their effect in vitro.

In some embodiments, the disease or condition is a cancer, e.g., a solid tumor or a hematologic malignancy. In some instances, the solid tumor is a carcinoma or a sarcoma. In some cases, the solid tumors include, but are not limited to, bladder cancer, bone cancer, brain cancer, breast cancer, colorectal cancer, endometrial cancer, esophageal cancer, eye cancer, head and neck cancer, kidney cancer, lung cancer, melanoma, ovarian cancer, pancreatic cancer, prostate cancer, stomach cancer, or thyroid cancer. In some cases, the solid tumor is a metastatic cancer. In some cases, the solid tumor is a relapsed or refractory solid tumor. In one aspect the payload is an anticancer therapy such as DOX and the cancer or cancer cell is breast cancer, a brain cancer such as neuroblastoma, glioma or neuroblastoma-glioma.

In some embodiments, the cancer is a hematologic malignancy. In some cases, the hematologic malignancy is a leukemia or a lymphoma. In some cases, the hematologic malignancy is a B-cell or a T-cell lymphoma. In some cases, the hematologic malignancy is a Hodgkin's lymphoma or a non-Hodgkin's lymphoma. Exemplary hematologic malignancy include, but are not limited to, chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the hematologic malignancy is a metastatic hematologic malignancy. In some cases, the hematologic malignancy is a relapsed or refractory hematologic malignancy.

In some embodiments, the treatment method further comprises administering an additional therapeutic agent with an engineered lipid-based vesicle described herein. In some cases, an additional therapeutic agent comprises, or consists essentially of, or consists of, a chemotherapeutic agent, an immunotherapeutic agent, a targeted therapy, radiation therapy, or a combination thereof. Illustrative additional therapeutic agents include, but are not limited to, alkylating agents such as altretamine, busulfan, carboplatin, carmustine, chlorambucil, cisplatin, cyclophosphamide, dacarbazine, lomustine, melphalan, oxaliplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some cases, the additional therapeutic agent comprises, or consists essentially of, or consists of, an inhibitor of the enzyme poly ADP ribose polymerase (PARP). Exemplary PARP inhibitors include, but are not limited to, olaparib (AZD-2281, Lynparza®, from Astra Zeneca), rucaparib (PF-01367338, Rubraca®, from Clovis Oncology), niraparib (MK-4827, Zejula®, from Tesaro), talazoparib (BMN-673, from BioMarin Pharmaceutical Inc.), veliparib (ABT-888, from Abb Vie), CK-102 (formerly CEP 9722, from Teva Pharmaceutical Industries Ltd.), E7016 (from Eisai), iniparib (BSI 201, from Sanofi), and pamiparib (BGB-290, from BeiGene).

In some cases, the additional therapeutic agent comprises, or consists essentially of, or consists of, an immune checkpoint inhibitor. Exemplary checkpoint inhibitors include pembrolizumab, nivolumab, tremelimumab, or ipilimumab. In some instances, the additional therapeutic agent comprises a modulator of PD-L1, PD-1, CTLA-4, LAG3, B7-H3, KIR, CD137, PS, TFM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some cases, the additional therapeutic agent comprises, or consists essentially of, or consists of, an antibody such as alemtuzumab, trastuzumab, ibritumomab tiuxetan, brentuximab vedotin, ado-trastuzumab emtansine, or blinatumomab In some cases, the additional therapeutic agent comprises, or consists essentially of, or consists of, a cytokine. Exemplary cytokines include, but are not limited to, IL-Iβ, IL-6, IL-7, IL-10, IL-12, IL-15, IL-21, or TNFα.

In some embodiments, the additional therapeutic agent comprises, or consists essentially of, or consists of, a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2p, CFA, or Flagellin.

In some cases, the additional therapeutic agent comprises, or consists essentially of, or consists of, an adoptive T cell transfer (ACT) therapy. In one embodiment, ACT involves identification of autologous T lymphocytes in a subject with, e.g., anti-tumor activity, expansion of the autologous T lymphocytes in vitro, and subsequent reinfusion of the expanded T lymphocytes into the subject. In another embodiment, ACT comprises use of allogeneic T lymphocytes with, e.g., anti-tumor activity, expansion of the T lymphocytes in vitro, and subsequent infusion of the expanded allogeneic T lymphocytes into a subject in need thereof.

In some instances, the additional therapeutic agent is a vaccine, optionally, an oncolytic virus. Exemplary oncolytic viruses include T-Vec (Amgen), G47A (Todo et al.), JX-594 (Sillajen), CG0070 (Cold Genesys), and Reolysin (Oncolytics Biotech).

In some cases, the additional therapeutic agent comprises, or consists essentially of, or consists of, a first-line therapy. As used herein, "first-line therapy" comprises a primary treatment for a subject with a cancer. In some instances, the cancer is a primary cancer. In other instances, the cancer is a metastatic or recurrent cancer. In some cases, the first-line therapy comprises chemotherapy. In other cases, the first-line treatment comprises radiation therapy. A skilled artisan would readily understand that different first-line treatments may be applicable to different type of cancers.

In some cases, the additional therapeutic agent comprises, or consists essentially of, or consists of, a second-line therapy, a third-line therapy, a fourth-line therapy, or a fifth-line therapy. As used herein, a second-line therapy encompasses treatments that are utilized after the primary or first-line treatment stops. A third-line therapy, a fourth-line therapy, or a fifth-line therapy encompass subsequent treatments. As indicated by the naming convention, a third-line therapy encompass a treatment course upon which a primary and second-line therapy have stopped.

In some cases, the additional therapeutic agent comprises, or consists essentially of, or consists of, a salvage therapy.

In some cases, the additional therapeutic agent comprises, or consists essentially of, or consists of, a palliative therapy.

In some instances, the engineered lipid-based vesicle described herein is administered in combination with a radiation therapy.

In some instances, the engineered lipid-based vesicle described herein is administered in combination with surgery.

In some embodiments, the disease or condition is a pathogenic disease. In some instances, the pathogen is a virus, a bacterium, protozoan, helminth, prion, or fungus. In some embodiments, the virus is a DNA virus or an RNA virus. The DNA viruses include single-stranded (ss) DNA viruses, double-stranded (ds) DNA viruses, or DNA viruses that contain both ss and ds DNA regions. The RNA viruses include single-stranded (ss) RNA viruses or double-stranded (ds) RNA viruses. In some cases, the ssRNA viruses are further classified into positive-sense RNA viruses or negative-sense RNA viruses.

Exemplary dsDNA viruses include viruses from the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

Exemplary ssDNA viruses include viruses from the family: Anelloviridae, Bacillariodnaviridae, Bidnaviridae, Circoviridae, Geminiviridae, Inoviridae, Microviridae, Nanoviridae, Parvoviridae, and Spiraviridae.

Exemplary DNA viruses that contain both ss and ds DNA regions include viruses from the group of pleolipoviruses. In some cases, the pleolipoviruses include Haloarcula *hispanica* pleomorphic virus 1, Halogeometricum pleomorphic virus 1, Halorubrum pleomorphic virus 1, Halorubrum pleomorphic virus 2, Halorubrum pleomorphic virus 3, and Halorubrum pleomorphic virus 6.

Exemplary dsRNA viruses include viruses from the family: Birnaviridae, Chrysoviridae, Cystoviridae, Endornaviridae, Hypoviridae, Megavirnaviridae, Partitiviridae, Picobirnaviridae, Reoviridae, Rotavirus, and Totiviridae.

Exemplary positive-sense ssRNA viruses include viruses from the family: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Marnaviridae, Mesoniviridae, Narnaviridae, Nodaviridae, Permutotetraviridae, Picornaviridae, Potyviridae, Roniviridae, Retroviridae, Secoviridae, Togaviridae, Tombusviridae, Tymoviridae, and Virgaviridae.

Exemplary negative-sense ssRNA viruses include viruses from the family: Arenaviridae, Bornaviridae, Bunyaviridae, Filoviridae, Nyamiviridae, Ophioviridae, Orthomyxoviridae, Paramyxoviridae, and Rhabdoviridae.

In some instances, an additional therapeutic agent in the context of a pathogenic infection comprises an antibiotic or an antiviral treatments such as, but not limited to, acyclovir, brivudine, docosanol, famciclovir, foscarnet, idoxuridine, penciclovir, trifluridine, valacyclovir, and pritelivir.

In some instances, the pathogen is human immunodeficiency virus (HIV). In some cases, the additional therapeutic agent comprises an HIV antiretroviral therapy. Exemplary HIV antiretroviral therapy includes: nucleoside reverse transcriptase inhibitors (RTIs) such as abacavir, emtricitabine, lamivudine, tenofovir disoproxil fumarate, and zidovudine;

non-nucleoside reverse transcriptase inhibitors (NNRTIs) such as efavirenz, etravirine, nevirapine, or rilpivirine; protease inhibitors (Pis) such as atazanavir, darunavir, fosamprenavir, ritonavir, saquinavir, and tipranavir; fusion inhibitors such as enfuvirtide; CCR5 antagonists such as maraviroc; integrase inhibitors such as dolutegravir and raltegravir; post-attachment inhibitors such as ibalizumab; pharmacokinetic enhancers such ac cobicistat; and cocktails such as abacavir and lamivudine; abacavir, dolutegravir, and lamivudine; abacavir, lamivudine, and zidovudine; atazanavir and cobicistat; bictegravir, emtricitabine, and tenofovir alafenamide; darunavir and cobicistat; dolutegravir and rilpivirine; efavirenz, emtricitabine, and tenofovir disoproxil fumarate; efavirenz, lamivudine, and tenofovir disoproxil fumarate; efavirenz, lamivudine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and tenofovir disoproxil fumarate; lamivudine and zidovudine; and lopinavir and ritonavir.

In some instances, the pathogen is a hepatitis virus, e.g., hepatitis A, B, C, D, or E. In some cases, an additional therapeutic agent comprises an antiviral therapy for hepatitis. Exemplary antiviral therapy for hepatitis include ribavirin; NS3/4A protease inhibitors such as paritaprevir, simeprevir, and grazoprevir; NS5A protease inhibitors such as ledipasvir, ombitasvir, elbasvir, and daclatasvir; NS5B nucleotide/nucleoside and nonnucleoside polymerase inhibitors such as sofosbuvir and dasabuvir; and combinations such as ledipasvir-sofosbuvir, dasabuvir-ombitasvir-paritaprevir-ritonavir; elbasvir-grazoprevir, ombitasvir-paritaprevir-ritonavir, sofosbuvir-velpatasvir, sofosbuvir-velpatasvir-voxilaprevir, and glecaprevir-pibrentasvir; and interferons such as peginterferon alfa-2a, peginterferon alfa-2b, and interferon alfa-2b.

In some embodiments, the disease or condition is an autoimmune disease or condition. Exemplary autoimmune disease or disorder include, but are not limited to, alopecia areata, autoimmune hemolytic anemia, autoimmune hepatitis, dermatomyositis, type 1 diabetes, juvenile idiopathic arthritis, glomerulonephritis, Graves' disease, Guillain-Barre syndrome, idiopathic thrombocytopenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjogren's syndrome, systemic lupus erythematosus, thyroiditis, uveitis, vitiligo, or Wegener's granulomatosis.

Exemplary additional therapeutic agents for the treatment of an autoimmune disease or disorder include, but are not limited to, corticosteroids such as prednisone, budesonide, or prednisolone; calcineurin inhibitors such as cyclosporine or tacrolimus; mTOR inhibitors such as sirolimus or everolimus; EVIDH inhibitors such as azathioprine, leflunomide, or mycophenolate; biologics such as abatacept, adalimumab, anakinra, certolizumab, etanercept, golimumab, infliximab, ixekizumab, natalizumab, rituximab, secukinumab, tocilizumab, ustekinumab, or vedolizumab; and monoclonal antibodies such as basiliximab, daclizumab, or muromonab.

In some embodiments, the disease or condition is an inflammatory condition. Exemplary inflammatory conditions include, but are not limited to, asthma, chronic peptic ulcer, tuberculosis, rheumatoid arthritis, ulcerative colitis, and Crohn's disease.

In some embodiments, the engineered lipid-based vesicle and the additional therapeutic agent are formulated as a separate dosage.

In some embodiments, the engineered lipid-based vesicle and the additional therapeutic agent are formulated as a combined dosage.

In some embodiments, the engineered lipid-based vesicle and the additional therapeutic agent are administered simultaneously.

In some embodiments, the engineered lipid-based vesicle and the additional therapeutic agent are administered sequentially.

In some embodiments, the engineered lipid-based vesicle is administered prior to administering the additional therapeutic agent.

In some embodiments, the engineered lipid-based vesicle is administered after administering the additional therapeutic agent.

In some embodiments, one or more of the methods described herein further comprise a diagnostic step. In some instances, a sample is first obtained from a subject suspected of having a disease or condition described above or for inducing an immune response in the subject. Exemplary samples include, but are not limited to, cell sample, tissue sample, tumor biopsy, liquid samples such as blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some instances, the sample is a tumor biopsy. In some cases, the sample is a liquid sample, e.g., a blood sample. In some cases, the sample is a cell-free DNA sample.

Various methods known in the art can be utilized to determine the presence of a disease or condition described herein or to determine whether an immune response has been induced in a subject. Assessment of one or more biomarkers associated with a disease or condition, or for characterizing whether an immune response has been induced, can be performed by any appropriate method. Expression levels or abundance can be determined by direct measurement of expression at the protein or mRNA level, for example by microarray analysis, quantitative PCR analysis, or RNA sequencing analysis. Alternatively, labeled antibody systems may be used to quantify target protein abundance in the cells, followed by immunofluorescence analysis, such as FISH analysis.

In some embodiments, the engineered lipid-based vesicle decreases toxicity associated with a naked payload, or associated with a payload-carrier composition in which the carrier is not the engineered lipid-based vesicle.

In some embodiments, the engineered lipid-based vesicle increases payload delivery to a target cell.

In some embodiments, the nanotube complex (e.g., a SWCNT complex or a BNNT complex) facilitates a distortion of lipids that comprise the lipid-based vesicle and thereby facilitates fusion of the lipids with a lipid membrane of a target cell.

In some embodiments, the engineered lipid-based vesicle decreases cell proliferation to a target cell.

In some embodiments, also described herein is a method of delivering a payload to a target, comprising: contacting an engineered lipid-based vesicle described herein or a composition described herein to the target, thereby delivering the payload to the target. In some embodiments, the target is a target cell. In some embodiments, the target cell is a cancer cell. In some embodiments, the target cell is a cell that is infected with a pathogen. In some embodiments, the target cell is a cell that is associated with an autoimmune disease. In some embodiments, the target cell is a cell that is associated with an inflammation. In some embodiments, the engineered lipid-based vesicle fused into the target cell through a hydrophobic interaction between the nanotube complex, optionally the SWCNT complex or the BNNT complex, and a lipid membrane of the target cell. In some embodiments, the target is an extracellular vesicle or a viral particle, wherein the extracellular vesicle is optionally an exosome or a microvesicle.

In some embodiments, further described herein is a method of detectably labeling a cell, comprising: contacting the cell with an engineered lipid-based vesicle described herein or a composition described herein; and visualizing the cell. In some embodiments, the cell is from a biopsy, optionally a tumor biopsy.

In some embodiments, the method described supra is an in vivo method.

In some embodiments, the method described supra is an in vitro method.

In some embodiments, the method described supra is an ex vivo method.

As used herein, the terms "treating," "treatment" and the like mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder. In one aspect, the term "treatment" excludes prophylaxis.

As used herein, to "treat" further includes systemic amelioration of the symptoms associated with the pathology and/or a delay in onset of symptoms. Clinical and subclinical evidence of "treatment" will vary with the pathology, the individual and the treatment. In one aspect, treatment excludes prophylaxis.

The term "ameliorate" means a detectable improvement in a subject's condition. A detectable improvement includes a subjective or objective decrease, reduction, inhibition, suppression, limit or control in the occurrence, frequency, severity, progression, or duration of a symptom caused by or associated with a disease or condition, such as one or more adverse symptoms, disorders, illnesses, pathologies, diseases, or complications caused by or associated with the disease or condition, or an improvement in an underlying cause or a consequence of the disease or condition, or a reversal of the disease or condition.

Treatment can therefore result in decreasing, reducing, inhibiting, suppressing, limiting, controlling or preventing a disease or condition, or an associated symptom or consequence, or underlying cause; decreasing, reducing, inhibiting, suppressing, limiting, controlling or preventing a progression or worsening of a disease, condition, symptom or consequence, or underlying cause; or further deterioration or occurrence of one or more additional symptoms of the disease condition, or symptom. Thus, a successful treatment outcome leads to a "therapeutic effect," or "benefit" of decreasing, reducing, inhibiting, suppressing, limiting, controlling or preventing the occurrence, frequency, severity, progression, or duration of one or more symptoms or underlying causes or consequences of a condition, disease or symptom in the subject, such as one or more adverse symptoms, disorders, illnesses, pathologies, diseases, or complications caused by or associated with a disease or condition. Treatment methods affecting one or more underlying causes of the condition, disease or symptom are therefore considered to be beneficial. Stabilizing a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial decrease, reduction, inhibition, suppression, limit, control or prevention in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, such as one or more adverse symptoms, disorders, illnesses, pathologies, diseases, or complications caused by or associated with the disease or condition, over a short or long duration of time (hours, days, weeks, months, etc.).

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Pharmaceutical Compositions and Formulations

In some embodiments, the pharmaceutical composition and formulations described herein are administered to a subject by multiple administration routes, including but not limited to, parenteral, oral, buccal, rectal, sublingual, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration. In some cases, the pharmaceutical composition is formulated as a lyophilized formulation.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995), Hoover, John E., Remington's Pharmaceutical Sciences, Mack Publishing Co., Easton, Pennsylvania 1975, Liberman, H. A. and Lachman, L., Eds., Pharmaceutical Dosage Forms, Marcel Decker, New York, N.Y., 1980, and Pharmaceutical Dosage Forms and Drug Delivery Systems, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethyl citrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkyl ethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits or Articles of Manufacture

In certain embodiments, a kit or article of manufacture described herein include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

EXAMPLES

These examples are provided for illustrative purposes only and not to limit the scope of the claims provided herein.

Example 1—Chemical Synthesis of Carbon Nanotube (CNT) Dimers

CNTPs contain a number of COOH groups at pore rim that represent a suitable target for chemical coupling reactions.

EDC coupling reaction. COOH groups at the CNT rim can be modified with EDC ((1-ethyl-3-(3-dimethylaminopropyl)carbodiimide hydrochloride) crosslinker to form an unstable O-acylisourea intermediate that then can react with the primary diamine molecule to form a cross-linking connection between two CNTPs. In a variation of this approach, O-acylisourea intermediate can first react with Sulfo-NHS to form a stable Sulfo-NHS ester intermediate, which then can react with the diamine molecule to again cross-link two CNTPs. To increase the yield and avoid self cross-linking, the cross-linking can be dome in two stages, where first CNTP-sulfo-NHS ester reacts with the excess of the diamine to couple only one CNTP to the linker moiety, followed by the second step where CNTP-sulfo-NHS is in excess to cross-link through the second amine group. See Scheme I.

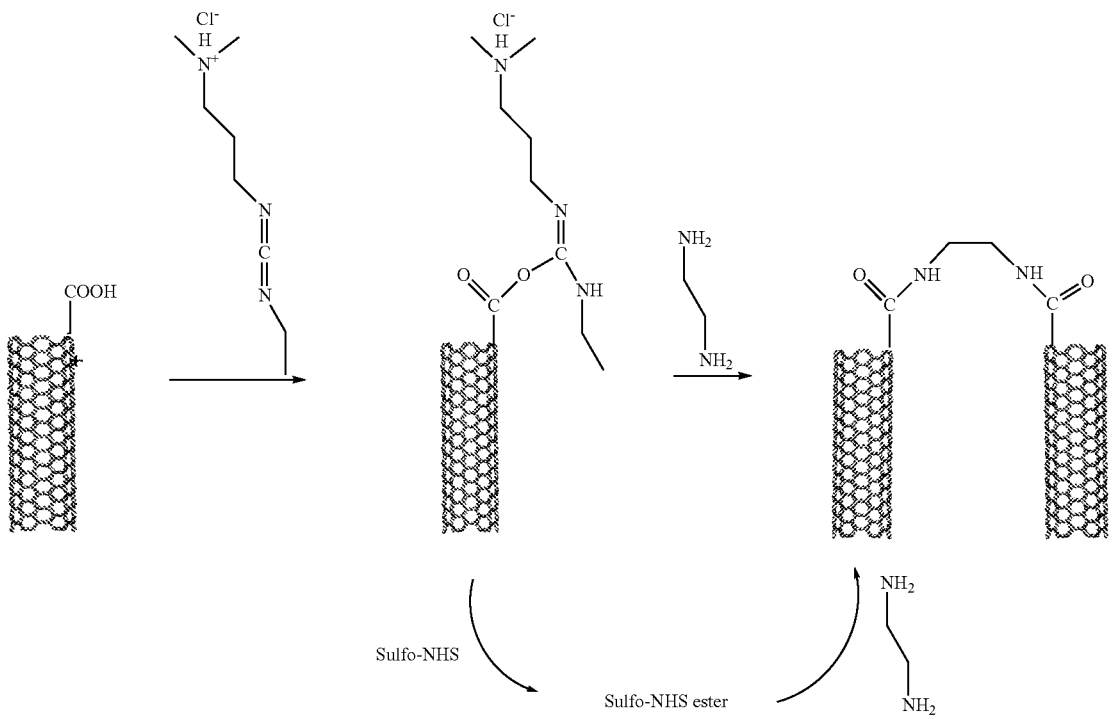

Scheme I

Alkine-Azide click chemistry. This preparation method involves using Huisgen azide-alkyne 1,3-dipolar cycloaddition reaction to couple two CNTP moieties, one functionalized with the aryl group and another with the azide group.

The azide-functionalized CNTPs can be prepared by reacting the native COOH-terminated CNTPs with trichloroacetonitrile, triphenylphosphine and sodium azide at room temperature. CNTPs functionalized with the aryl groups can be prepared by first converting the COOH groups on the CNTP mouth into CH2-OH groups by reacting them with $LiAlH_4$, then by converting the alcohol moiety into chloride by reacting the product with thionyl chloride, then finally by reacting the product of that reaction with $HC_2Li/H_2NC_2H_4NH_2$ (lithium acetylenide/ethylenediamine complex). See Scheme II.

Scheme II

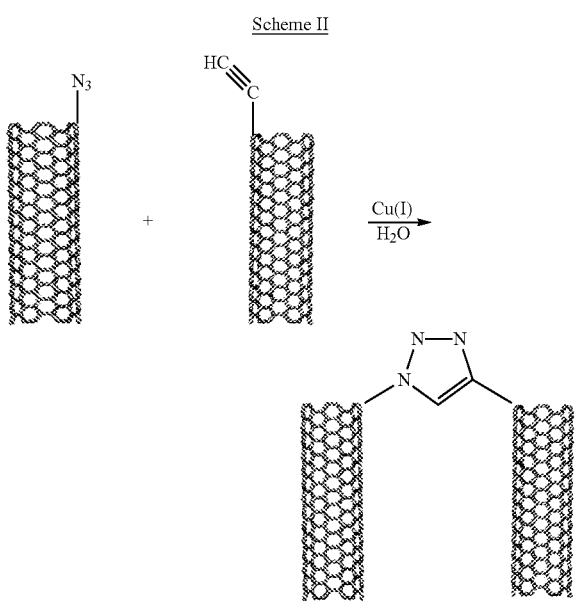

Example 2—Virus-Like Membrane Fusion and Drug Delivery with Carbon Nanotube Porins After more than a billion years of evolution viruses acquired highly efficient and precise machinery that allows them to evade host's defenses and deliver their genetic payload. On the way to the target the viral genome is protected inside robust capsids that also carry sophisticated protein apparatus that can hone onto the target cell membrane and fuse the virus particle to the cell, releasing the capsid content directly into the interior. In contrast, modern clinical pharmacology often struggled to deliver potentially life-saving drugs to target organs and tissues. Drugs are often poorly soluble, strongly toxic to other tissues, have a tendency to accumulate in non-target tissues, bind to other cellular components, or have a problem internalizing into the cell. To mitigate these problems, researchers have been developing a number of drug delivery approaches that encapsulate drugs in external carriers that circulate through the blood stream. Drug delivery systems that are on the market, in clinical trials or in development are based on nanoparticles, nanogels, antibody conjugates, and other systems; however, some of the most successful approaches are based on encapsulating drugs in liposomal carriers.

Liposome-based delivery strategy encapsulates payload drugs in a carrier whose surface resembles a cell membrane, thus allowing them to be administered systemically and avoid rapid degradation and a lot of toxicity effects. However, even those carriers still tend to accumulate plasma proteins and get retained in reticuloendothelial system instead of reaching their target. PEG-functionalized liposomes tend to be significantly more resistant to this mechanism and the majority of clinically successful liposomal drug formulations used PEG functionalization and also added cholesterol to the membrane as a way to suppress phospholipid exchange. Yet, these strategies carry an inherent tradeoff between enhancing liposomal stability on the way to the target and the ease of payload release once that target has been reached. Researchers introduced a number of delivery approaches are based on pH, ultrasound, or heat-triggered release; however, targeting these stimuli to the appropriate tissues brought their own set of complications and often was not very effective in penetrating the cell membrane.

A potentially attractive alternative approach would involve a mechanism that would facilitate direct payload delivery from liposomes into the cell interior in a way that mimic viral infection mechanism. The structure of viral fusion machinery provides some clues for designing such an approach. Most of the effective viral fusion proteins, such as hemagglutinin [other examples here and references] share some structural similarities. They often form hydrophobic stalks that have membrane-perturbing activity, can insert into the opposite membrane and promote formation of hemi-fusion intermediates and subsequent transition to full fusion. Previous molecular dynamics (MD) simulations predicted5 that carbon nanotube porins (CNTPs)—short pieces of carbon nanotubes inserted into lipid membranes—should be capable of mimicking some of these gross behaviors and facilitating vesicle fusion.

Here small (0.8 nm) diameter CNTPs were shown to be incorporated into large unilamellar vesicles (LUV) to facilitate leakage-free full fusion to the other LUVs. A combination of experimental measurements and coarse-grained MD simulations were used to explore the kinetics of the fusion process and reveal its molecular-scale mechanism. It was found that the fusion process is sensitive to the precise geometry of CNTPs in the membrane and depends critically on the presence of CNTP dimers. It was also demonstrated that virus-like CNTP-containing liposomes are effective for delivering a common first line of defense chemotherapeutic agent, doxorubicin, to cancer cells.

CNTPs-Mediated Vesicle Fusion

Figure 1A:
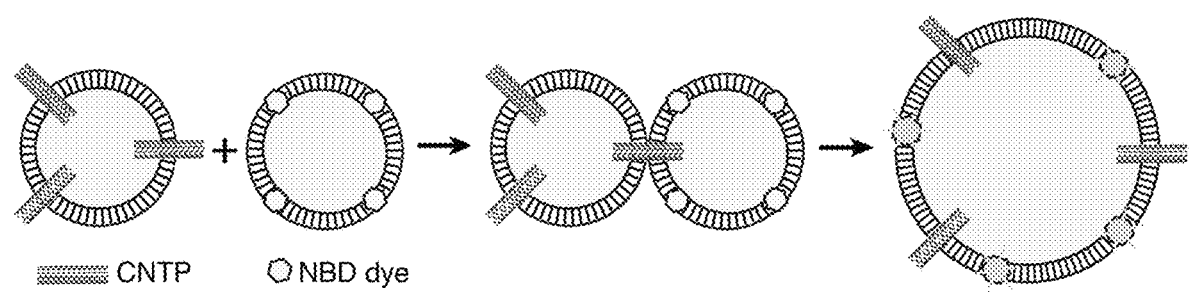
FIG. 1A-FIG. 1E illustrate membrane fusion facilitated by CNTPs.
Figure 1B:
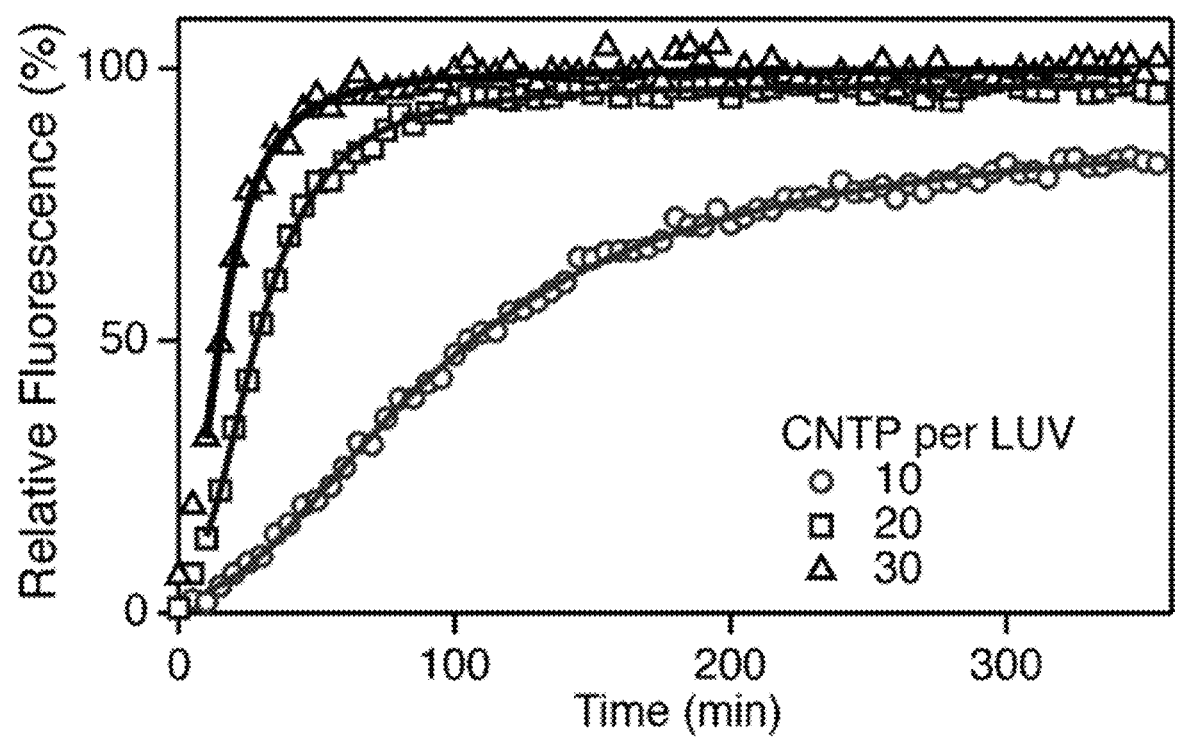

To test the hypothesis that CNTPs can promote vesicle fusion the de-quenching assay was used where large unilamellar vesicles was mixed with 0.8 nm CNTPs (CNTP-LUVs) inserted into the lipid shell with DOPC vesicles labeled with an NBD dye (NBD-LUVs) at a concentration just above the self-quenching threshold. Mixing of the lipid content during fusion de-quenched the NBD dye. (FIG. 1A), allowing us to quantify the fusion process by monitoring the dye fluorescence. After mixing of these two vesicle populations NDB dye fluorescence showed strong increase on the scale of tens of minutes, indicating that vesicle fusion was indeed taking place in this system. In contrast, fluorescence kinetics recorded in control experiments where CNTP-LUVs were replaced by pure DOPC vesicles did not show a measurable signal change, indicating that the presence of CNTPs in the vesicle shell was critical to inducing fusion events. Fluorescence races showed a short incubation period, likely related to the initial time it takes vesicles from different populations to establish contact, followed by a rapid rise in fluorescence signal before eventually plateauing out. As the CNTP concentration was increased in vesicles, the de-quenching signal would reach the plateau faster (FIG. 1B), again indicating that CNTPs were responsible for the fusion events. In contrast, the control experiment where vesicles did not contain any CNTPs showed only monotonic fluorescence decrease.

To further quantify the fusion kinetics the fluorescence traces was fitted to the Hill equation:

$$F=(1+(\tau/t)^n)^{-1} \qquad (1)$$

Where F is normalized fluorescence signal; $\tau$ is the fusion halftime; t is the time; and n is Hill coefficient. The fusion rate, calculated as $2/2/\tau$, increased with the increased loading of CNTPs in the vesicle. However, a surprising finding was that the fusion rate did not scale linearly with the CNTP concentration and instead followed a quadratic dependence (FIG. 1). These data suggest that the key step of the fusion process is mediated by a CNTP dimer, that is, formed by CNTP associating in the membrane.

Activation energy measurements provide further information about the fusion process. As the temperature was increased, fusion rate showed rapid increase (FIG. 1C, inset), with the corresponding Arrhenius activation energy in the range of 25 kJ/mole. This value of ca. $10k_BT$ is significantly smaller than the lower boundary of the activation energy barrier reported by recently by Pincet and Rothman for spontaneous collision-induced fusion of 60 nm vesicles. Note that the LUVs used in our experiments had a significantly larger radii or 200 nm, which should further reduce the intrinsic bilayer strain and increase the barrier for spontaneous vesicle fusion. These data also reinforce our conclusion that CNTPs played a key enabling role in the processes that was observed.

The role of the charge state of the CNTP ends also plays in these events was explored by determining activation energy values as a function of pH. CNTPs are terminated with COOH groups that are ionized at pH values above 5.5. The activation energy for the fusion process generally showed little dependence on pH (FIG. 1C), suggesting that hydrophobic interactions between the lipid tails and CNTP surface play the dominant role relative to the electrostatic interactions. Interestingly, the activation energy value reduced by about 20% around the pH 5.5, which corresponds to the $pK_a$ of the COOH end groups, suggesting that, perhaps, a mixture of charged and uncharged CNTPs can be an even more efficient fusion mediator.

In general, mixing of the lipid components does not always indicate full fusion. The lipid content of the interacting vesicles could be fully mixed, but the vesicles could still remain in the hemi-fused state where the two compartments are still separated. Thus, it was important to prove that CNTP-mediated fusion proceeds to full fusion by using another dye de-quenching assay where the target DOPC vesicles were filled with a solution of sulforhodamin B (SRB) dye in a concentration above its self-quenching threshold. After these vesicles were mixed with the CNTP-LUVs gradual de-quenching of the SRB dye fluorescence (FIG. 1E) was observed, suggesting that fusion proceeded all the way to full content mixing. As expected, the timescale for the content mixing was about twice as slow as the timescale observed in the corresponding NDB membrane dye assay, indicating that hemifusion and the corresponding lipid mixing happened first, followed by full fusion and content mixing. The absence of content leakage is another characteristic of the fidelity of the fusion. It was quantified by adding a dye-scavenging tetramethylrhodamine (TRIC) polyclonal antibody to the vesicle solution. As the addition of this antibody did not lead to any significant modification of the fluorescence kinetics (FIG. 1E), it was concluded that there was very little if any free dye present in solution after fusion. The gradual increase of the SRB dye fluorescence signal is also consistent with the content mixing, as opposed to a much more sudden signal spike that would have been expected in case of content leakage. Full content mixing and absence of content leakage in similar CNTP-mediated experiments were observed with DOPC vesicles that contained 30% of cholesterol. See FIG. 7.

Figure 1C:
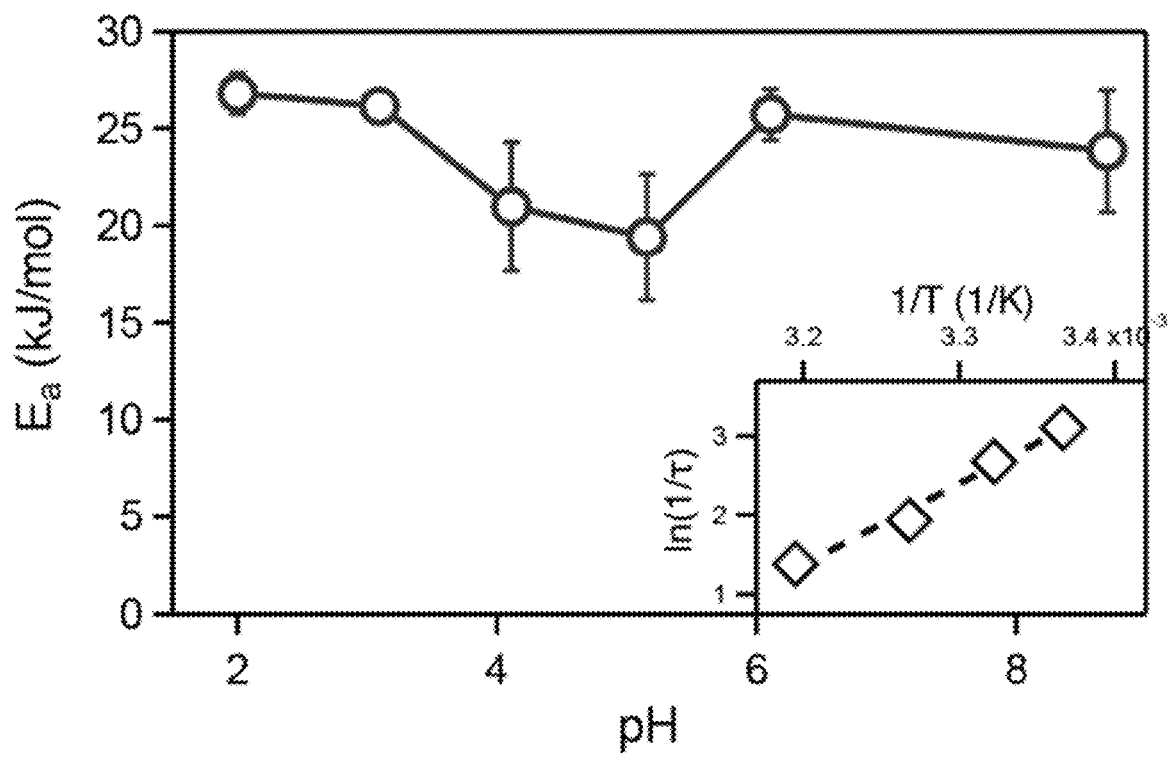
Figure 1D:
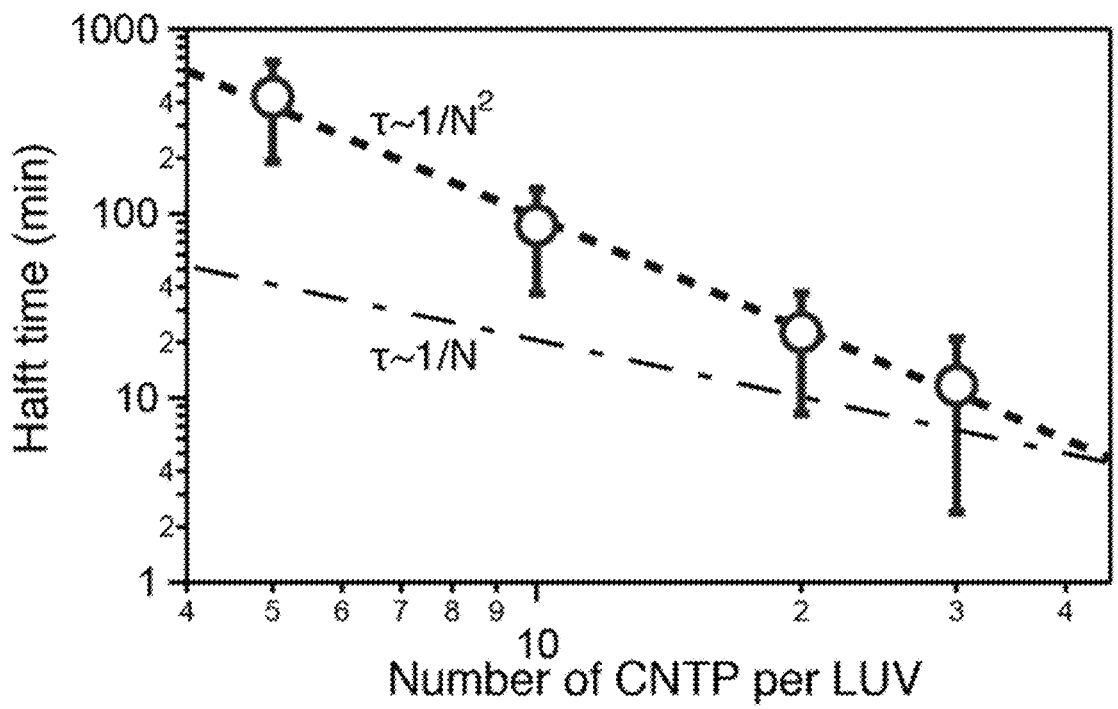
Figure 1E:
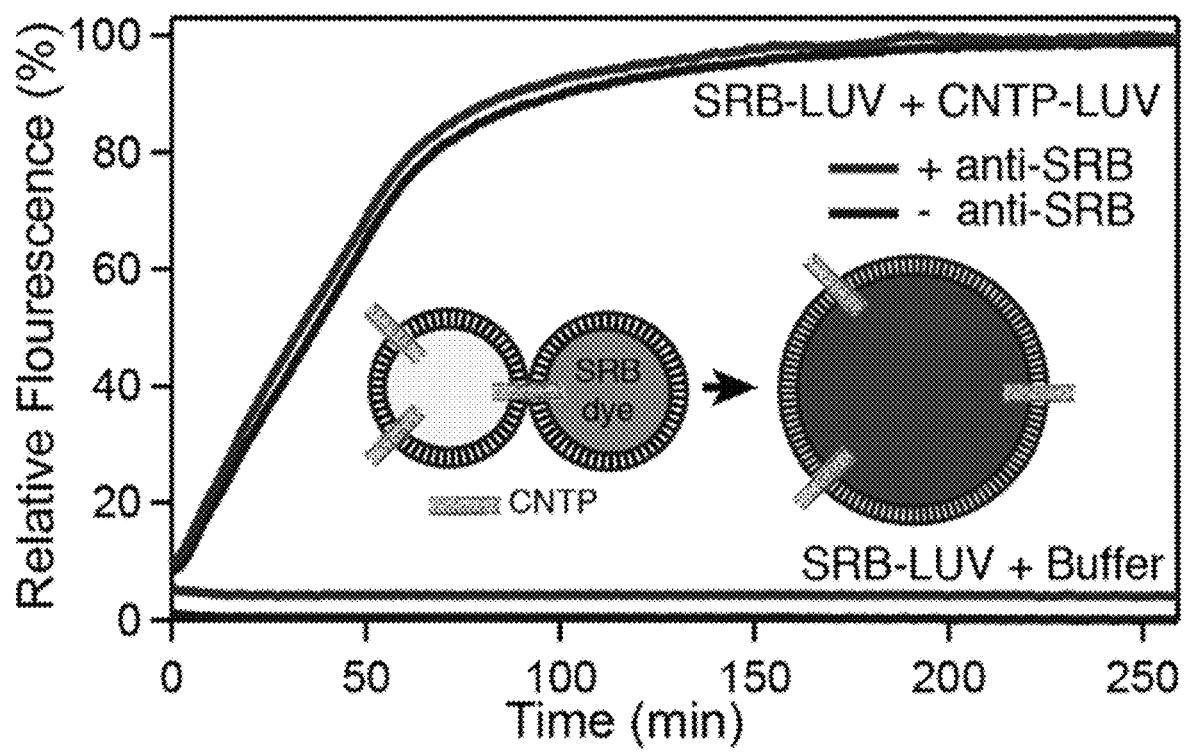

To explore the thermodynamics of this process further, fusion kinetics was monitored at different temperatures. Fusion rate followed an Arrhenius dependence (FIG. 1C, inset) with the corresponding activation energy, $E_a$, of ca. 25 kJ/mol or ca. 10 $k_BT$ (FIG. 1C). This value is significantly smaller than the activation energy of $30k_BT$ that was recently reported for spontaneous fusion of small diameter vesicles, indicating that CNTPs indeed lower the barrier to fusion. Interestingly, the activation energy showed weak dependence on pH (FIG. 1C) with the barrier lowering by an additional $2k_BT$ at pH values between 4 and 5, and recovering back to the original value of 10 $k_BT$ at pH values below. As DOPC remains in a zwitterionic charge state over the whole range of pH used in the measurements, it was believed that this behavior originates in the charge state of the CNTP ends, which indeed become protonated at the pH interval between 4 and 5. It was speculated that COOH/COO⁻ interactions stabilize the CNTP dimers that facilitate fusion.

To gain further insights into the molecular details of the fusion process, coarse-grained MD simulations of 15 nm DOPC vesicles stapled by monomers, dimers or trimers of 0.8 nm CNTPs were performed (FIG. 2A, FIG. 4A-FIG. 4C, Table 1). To control the driving force and kinetic rate of vesicle fusion, the asymmetry in the number of lipids in the outer and inner leaflets of the two vesicles was varied, defined as $\Delta N = N_{lipids\ outer} - N_{lipids\ inner}$. By increasing the number asymmetry, the bilayer strain and fusion propensity of vesicles were lowered, allowing to differentiate more clearly among the fusiogenic characteristics of CNTP monomers, dimers, and trimers.

The structure of the CNT dimer plays an important role in facilitating fusion, as evidenced by the experimental observation of the second order fusion kinetics in a system when CNTs are allowed to diffuse in the lipid bilayer and associate freely. The dimer structure and geometry facilitate distortion of the inner lipid layers of the interacting vesicles in a way that promotes membrane fusion. Specifically, a wider hydrophobic facet of the dimer facilitates lipid tail migration. Crucially, a narrower facet of the CNT dimer then allows the lipid tails to reach across and establish tail-tail contact that represents the critical step towards fusion.

In contrast to the structure of the CNT dimer, the small diameter of the CNT monomer does not provide enough surface area to generate sufficient lipid distortion. A trimer bundle is too thick for allowing strong tail-tail contact that ultimately leads to fusion.

Figure 2A:
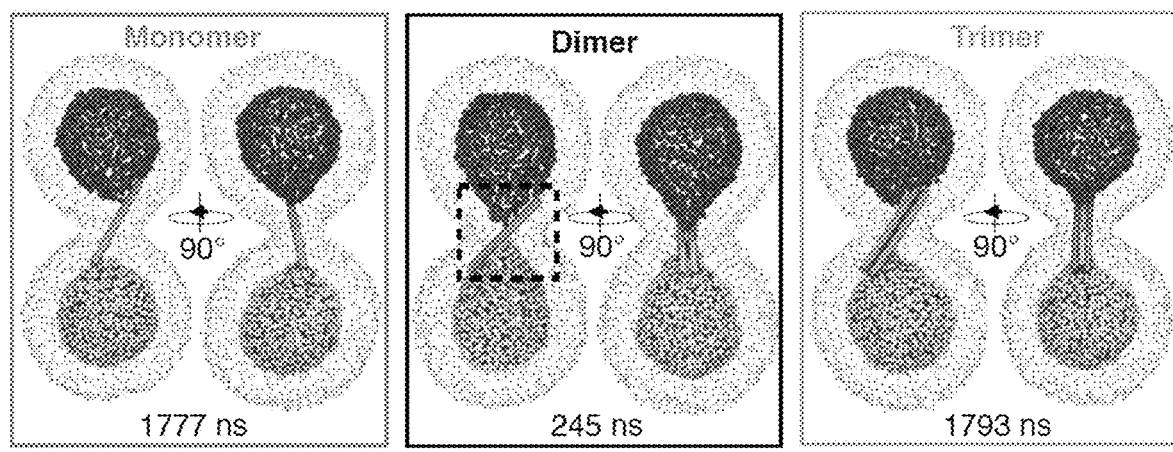
FIG. 2A-FIG. 2D show coarse-grained MD simulations of CNTP-mediated vesicle fusion.
Figure 2B:
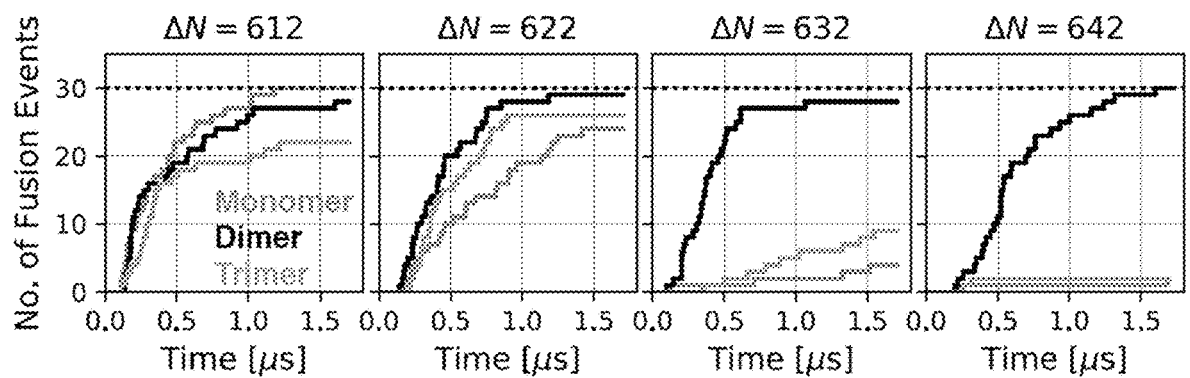

CNTP dimers rapidly fused vesicles without any significant changes in fusion time over the full range of tested asymmetries. In contrast, CNTP monomers and trimers fused only vesicles with low number asymmetry, i.e. only in presence of significant bilayer strain (FIG. 2B). At high number asymmetry, monomer and trimer fusion slowed down dramatically, with only few fusion events observed during the simulation time.

Figure 2C:
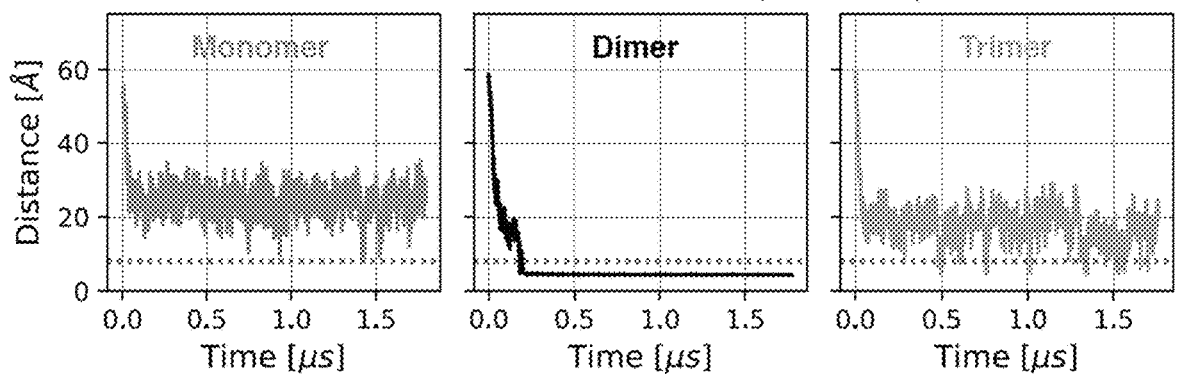
Figure 5:
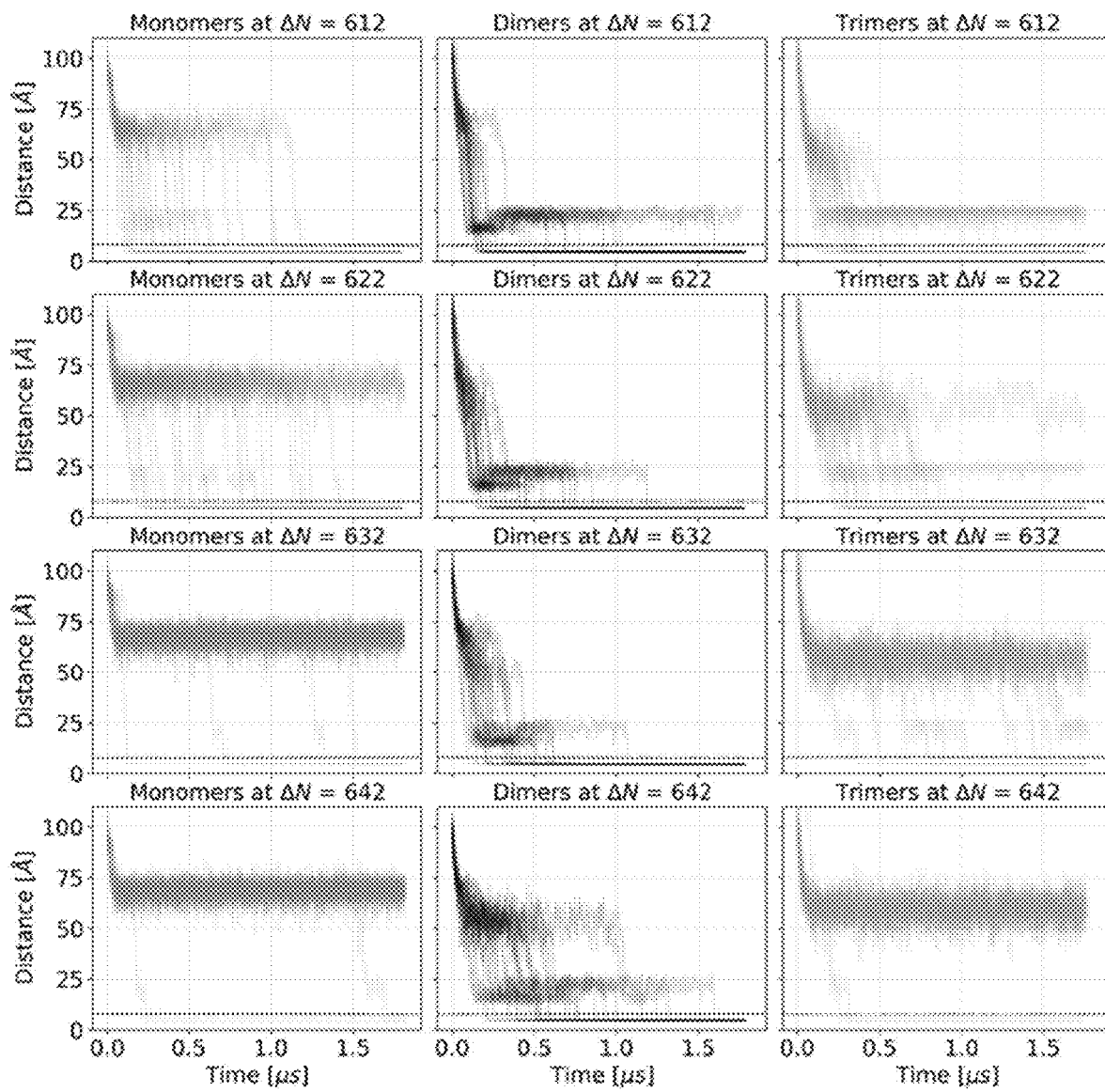
FIG. 5 illustrates minimal lipid headgroup-headgroup distances. Minimal P04/PO4 phosphate bead distance of the opposing inner leaflets for monomer, dimer, and trimer mediated fusion simulations at $\Delta N$=612, 622, 632 and 642, respectively. The time traces of all 30 replicas for each system are shown. The dashed lines are drawn at 8 Å distance which defines contact and fusion.
Figure 6:
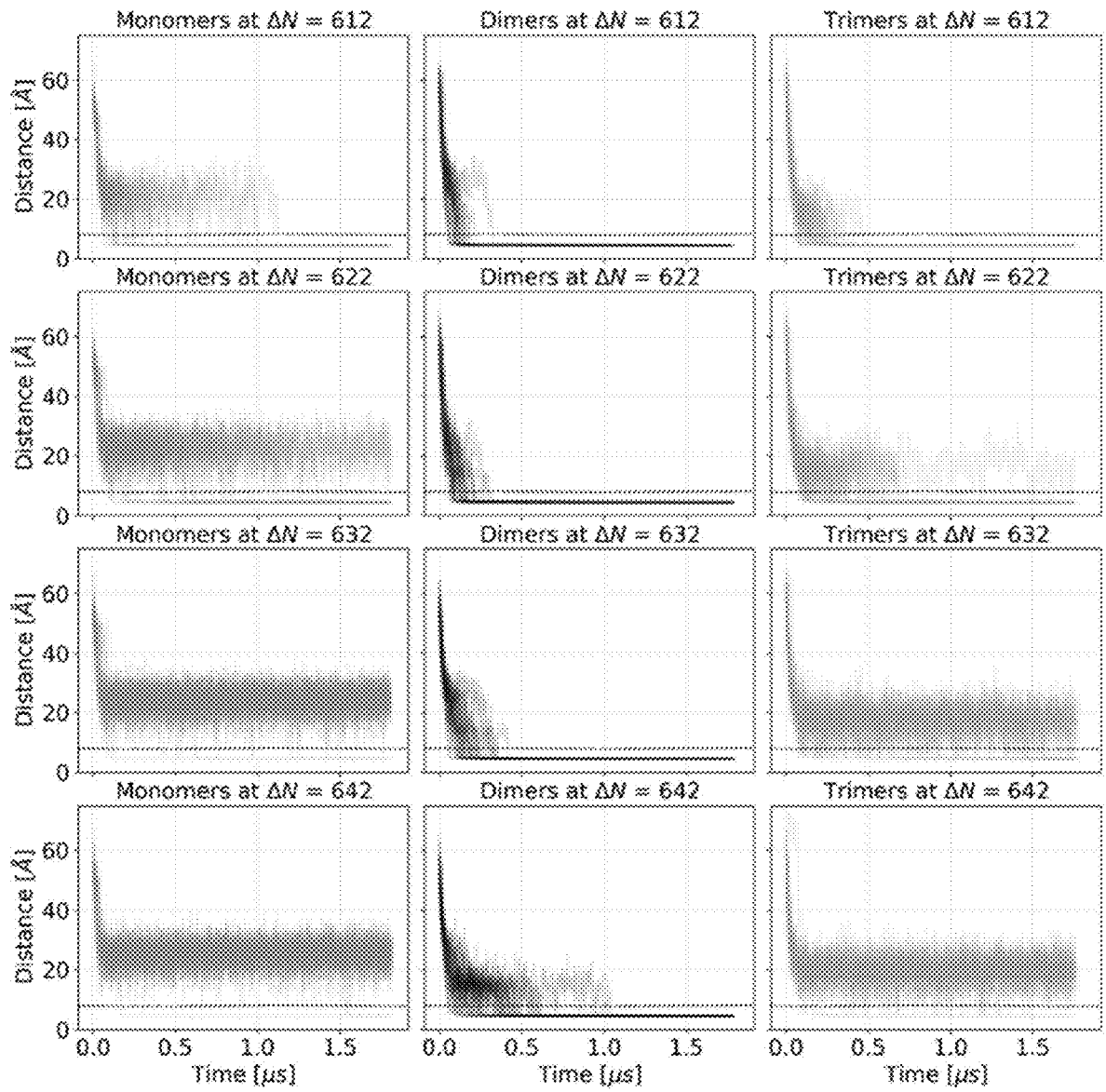
FIG. 6 illustrates minimal tail-tail distances. Minimal distance of C5A/B tail beads of the opposing inner leaflet lipids for monomer, dimer, and trimer mediated fusion simulations at $\Delta N$=612, 622, 632 and 642, respectively. The time traces of all 30 replicas for each system are shown. The dashed lines are drawn at 8 Å distance which defines contact.

A more detailed insight into the fusion dynamics was gained by monitoring the minimal distance between any two tails in the inner leaflets of the two vesicles. In all simulations, CNTP dimers achieved initial inner-leaflet contact, which is a prerequisite for fusion, more rapidly than CNTP monomers (FIG. 2C, FIG. 5). Consistently, in all relaxed pre-fusion systems, CNTP dimers distorted inner leaflets to a higher degree than monomers and trimers, leading to rapid inner leaflet contact and subsequent fusion (FIG. 2C, FIG. 6).

Figure 2D:
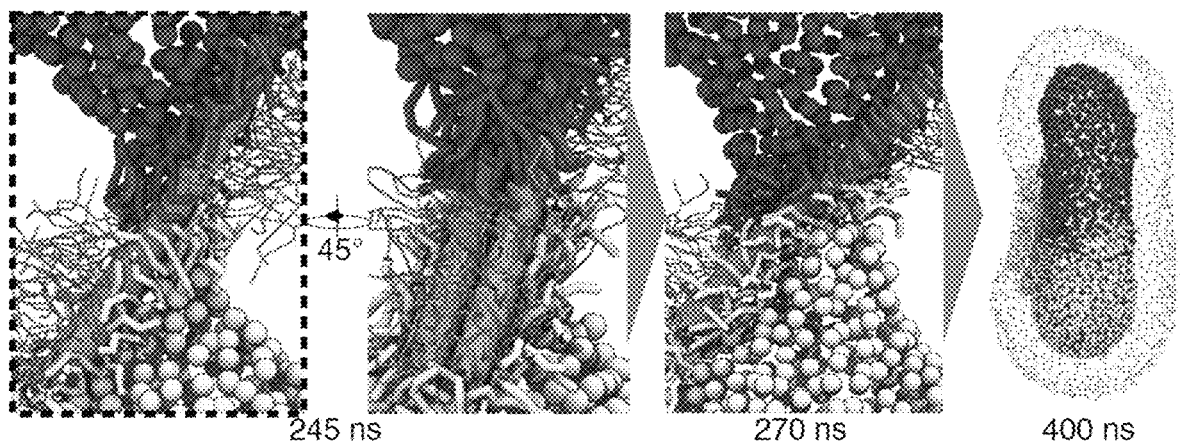

The asymmetric shape of the CNTP dimer explains its distinct fusogenic properties. The energetic drive to cover the hydrophobic surface of the wide faces by lipid tails (FIG. 2D) pulls the two vesicles together and causes significant distortion of the distal leaflets. The narrow edges of the CNTP dimer facilitate tail-tail contacts between the opposing inner leaflets. In contrast, single thin CNTPs are not coated as densely with lipid tails and consequently do not distort the distal leaflets as much (FIG. 2A, FIG. 2C, FIG. 5), impeding fusion. Trimers are too thick to establish sufficient tail-tail interactions (FIG. 2A, FIG. 2C, FIG. 5) due to considerable distance separating distal leaflets, and thus fail to induce fusion on the MD simulations timescale.

Figure 7:
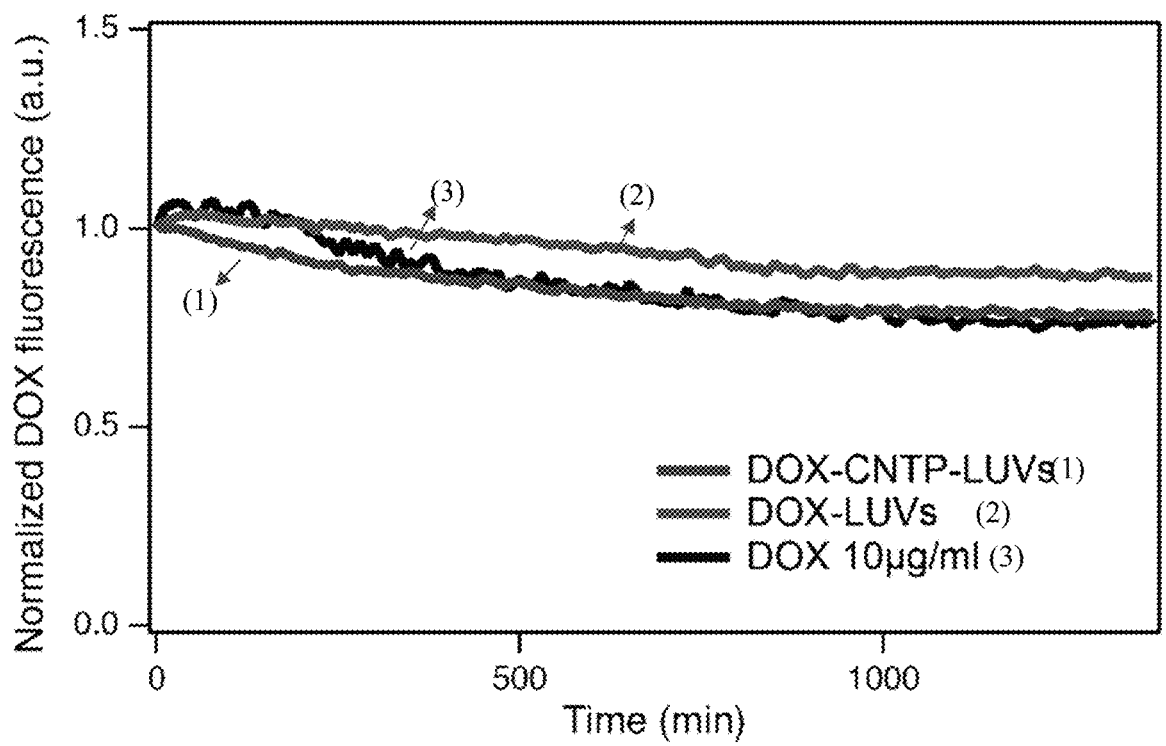
FIG. 7 illustrates long-term DOX leakage from the vesicles at 37° C. Time trace of the fluorescence signal from DOX (480EX/590EM) monitored for 18 hours for DOX-LUVs and DOX-CNTP-LUVs. Control experiment, which monitored fluorescence signal from the 10 µg/ml DOX solution, quantified the extent of DOX photobleaching. DOX is self-quenched at high concentrations, thus leakage of DOX from vesicles should result in the increase of DOX fluorescence emission. This data show that signals from both DOX-CNTP-LUV and DOX-LUV samples are consistent with background DOX photobleaching, indicating that there was no significant leakage of the drug from the vesicles on the experiment timescale.
Figure 8A:
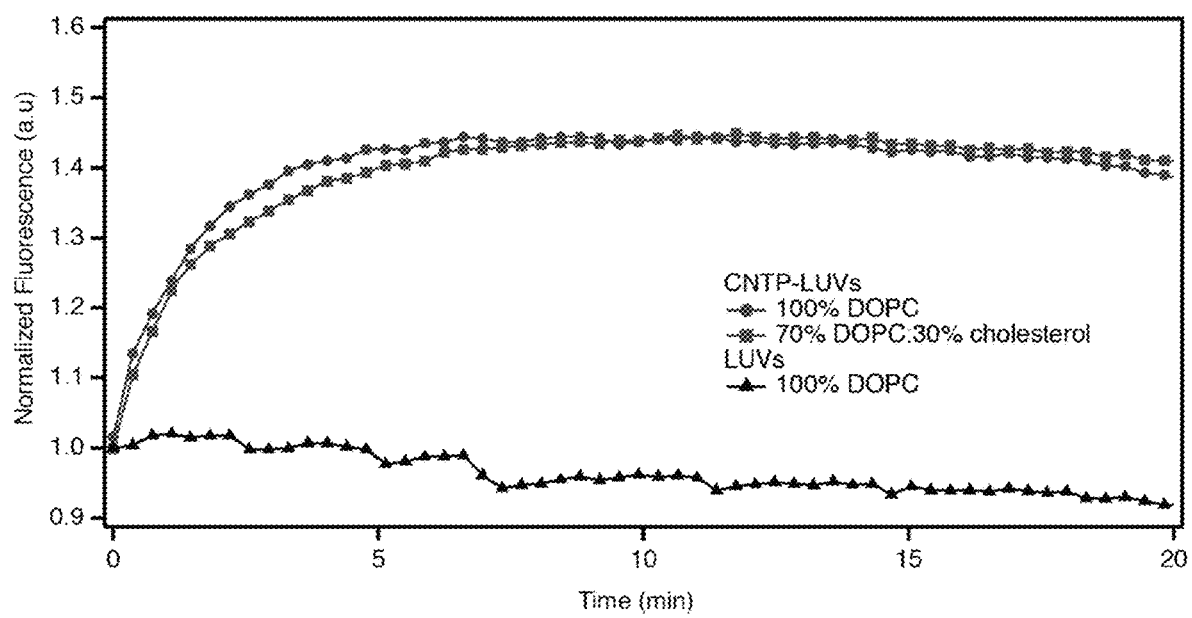
FIG. 8A-FIG. 8C illustrate cholesterol content of the liposomes and CNTP modification effect on fusion efficiency.
Figure 8B:
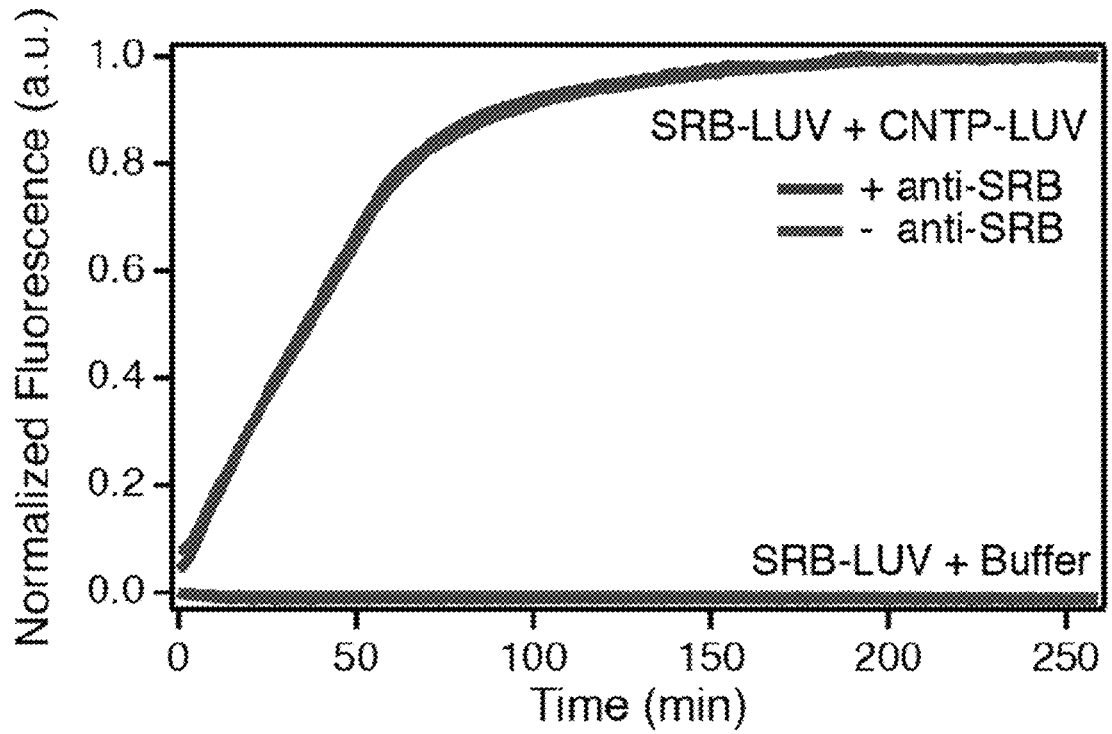

To demonstrate that the fusion-based mechanism can be used to carry and deliver drugs to live cells (FIG. 3A), a first line of defense chemotherapeutic agent, doxorubicin (DOX), was encapsulated in CNTP-LUVs. Systemic administration of DOX is complicated by its significant cardiac toxicity, which is often mitigated by encapsulating very high amounts of the drug into PEGylated liposomal carriers that passively accumulate in tumors. To assess the drug delivery potential of CNTP-modified liposomes, the performance in a series of cell viability assays on two different cell lines were tested: NG108-15 cell line (a mouse neuroblastoma and rat glioma hybrid) and MDA MB-231 cell line (human breast cancer cells) (FIG. 3). About 10 µg/ml DOX was encapsulated in 100 nm diameter CNTP-LUVs. DOX molecule size is larger than the CNTP pore size, excluding the possibility of drug leakage through the nanotubes. The CNTP-LUVs also contained 30% cholesterol to ensure that the membrane remains leak-free. Indeed, control experiments revealed no long-term drug leakage (FIG. 7). These smaller diameter vesicles also showed high fusion efficiency with an average τ1/2 of less than 1 hour. Pure DOPC vesicles of similar size also showed similar kinetics in both membrane and content mixing assays (FIG. 8A, FIG. 8B).

Figure 3A:
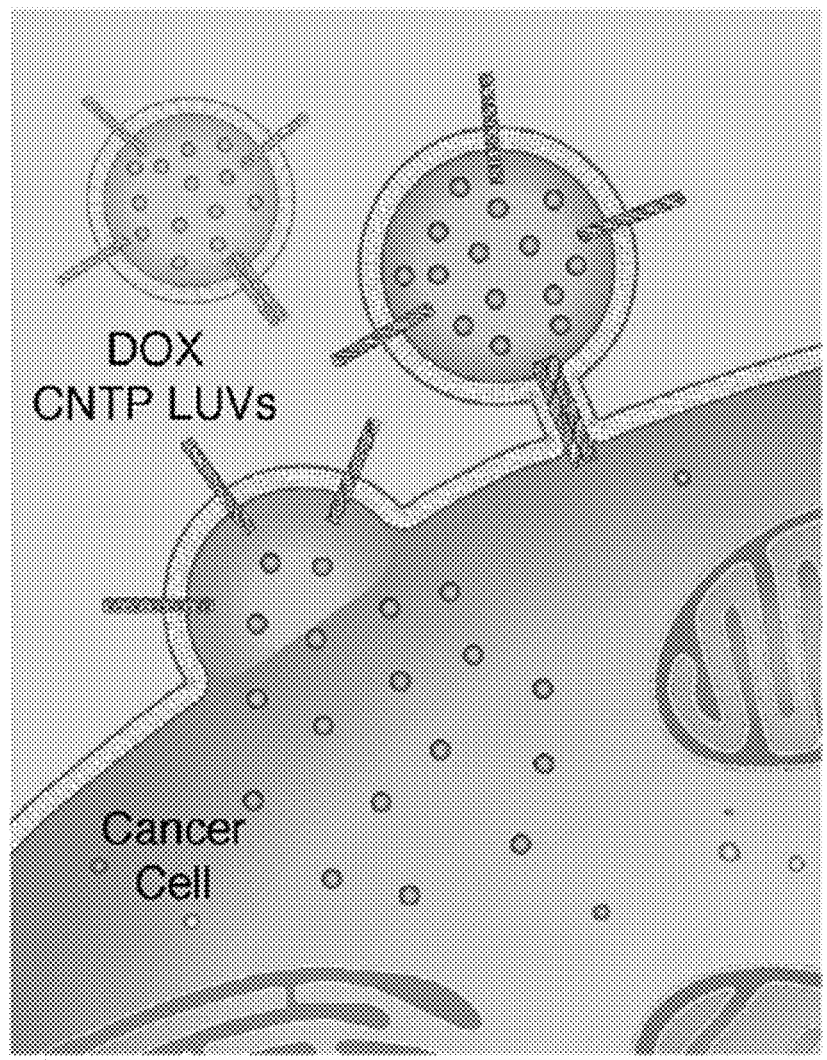
FIG. 3A-FIG. 3E illustrate drug delivery with CNTPs.
Figure 3B:
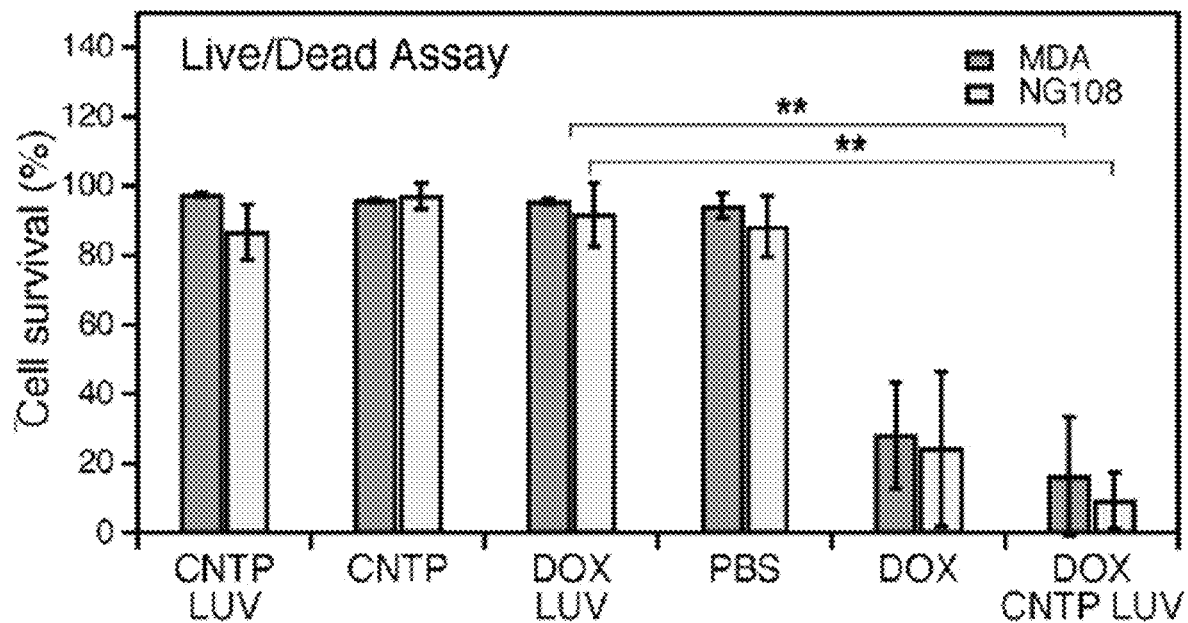
Figure 3C:
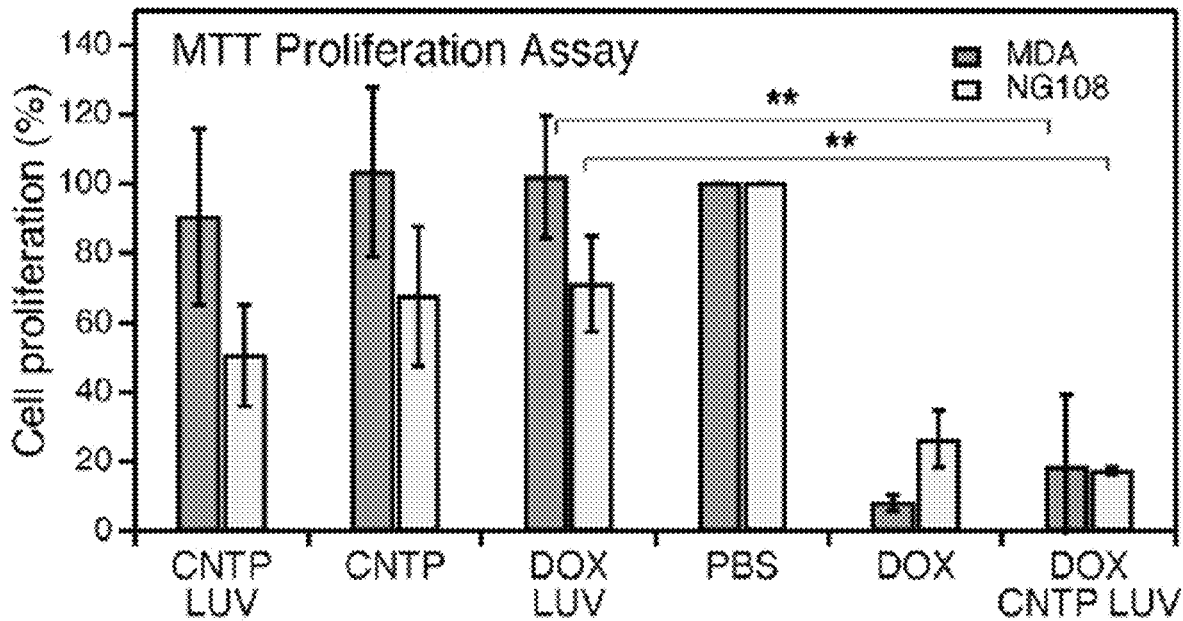
Figure 3D:
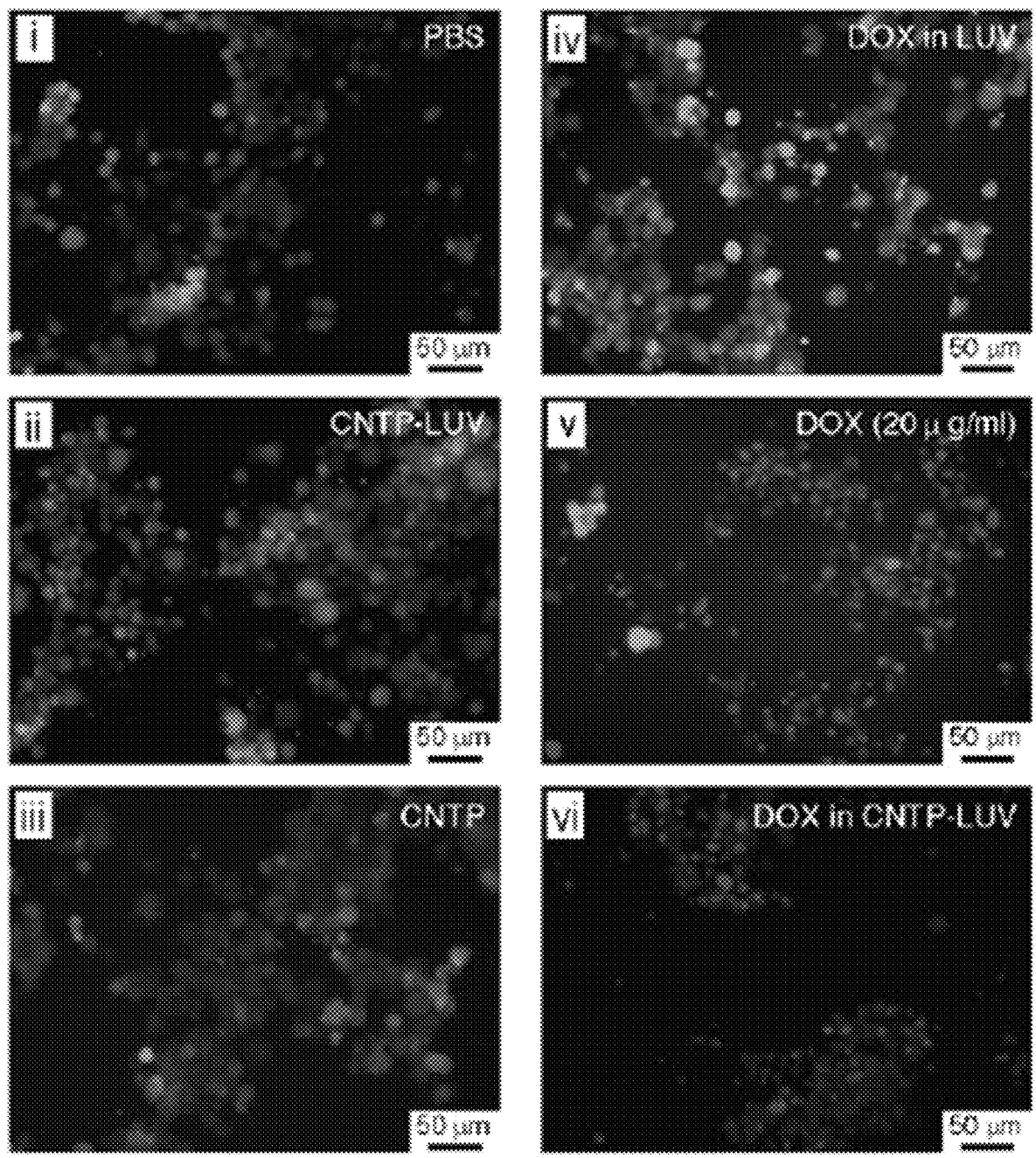
Figure 3E:
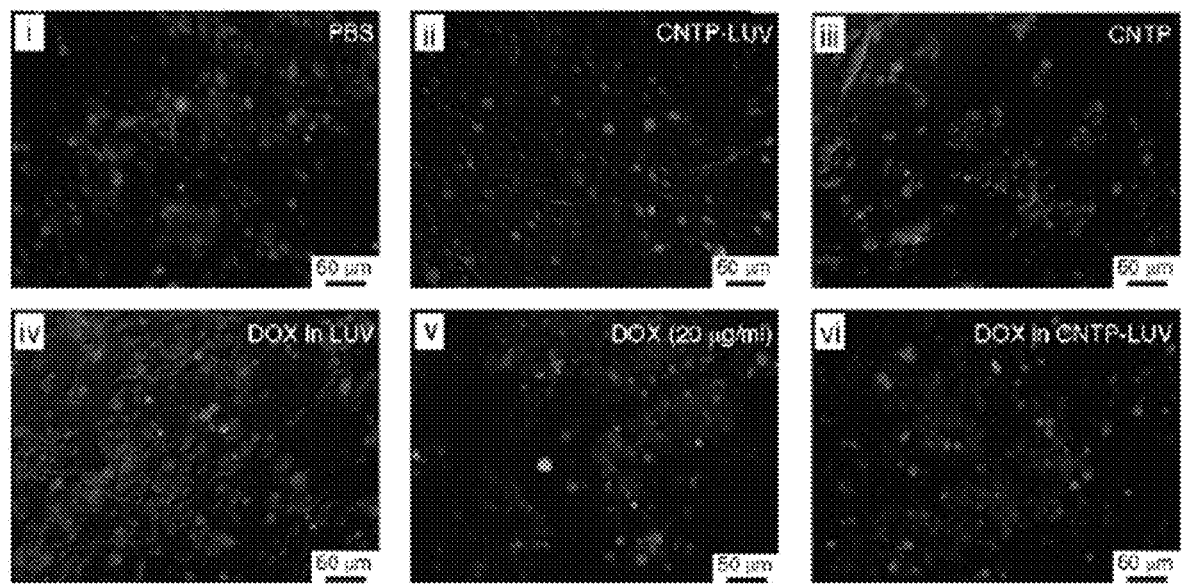

Exposure to DOX-loaded CNTP-LUVs killed a large percentage of the cell population in both cell lines that were tested, with only 9% of NG108 cells and 16% of MDA cells remaining alive after 48 hours (FIG. 3B, FIG. 3D(iv), FIG. 3E(iv)). The efficiency of the CNTP-LUVs loaded with 10 µg/ml of DOX (FIG. 3B, FIG. 3C, FIG. 3D(v), FIG. 3E(v)) was mostly comparable to the effect of administering 20 µg/ml of free DOX (FIG. 3B, FIG. 3C, FIG. 3D(v), FIG. 3E(v)). Note that DOX-CNTP-LUVs used in the experiments contain a much smaller overall amount of DOX and thus will likely show lower systemic toxicity. Moreover, the 10 µg/ml DOX concentration that was used in the experiment is significantly lower than the 2000 µg/ml concentration that commercial formulations use for liposomal delivery of DOX.

By contrast, control experiments (FIG. 3B, FIG. 3D (i,ii,iii) and FIG. 3E (i,ii,iii)) with cells exposed to CNTP-LUVs and free CNTPs showed very low cytotoxicity, with typically over 85% of the cells remaining alive after the same 48 hours of exposure. These viability numbers were on par with those measured after exposure to pure PBS buffer (88% and 94% for NG108 and MDA cells, respectively). Interestingly, when pure LUVs were loaded with 20 µg/ml of DOX, their cytotoxicity was on par with control experiments (FIG. 3B, FIG. 3D (i), FIG. 3E (i)), showing little to no efficiency without the presence of a viable delivery mechanism.

Cell proliferation (MTT) assays results (FIG. 3C) tracked the trends obtained in the cell viability (live/dead) assay across all samples that were tested. Exposure of both cell lines to DOX-loaded CNTP-LUVs led to a significant decrease in the cells' proliferation ability. Additional control experiments where the cells were exposed to CNTPs and CNTP-LUVs in presence of free DOX in solution did not show a statistically significant cell viability decrease (FIGS. 9A-9E, FIGS. 10A-10E), indicating that CNTP-mediated fusion was indeed the main pathway for the drug entry into the cancer cells, and that the drug did not enter through defects in the cell membrane created by free CNTPs or CNTP-LUVs.

Figure 11A:
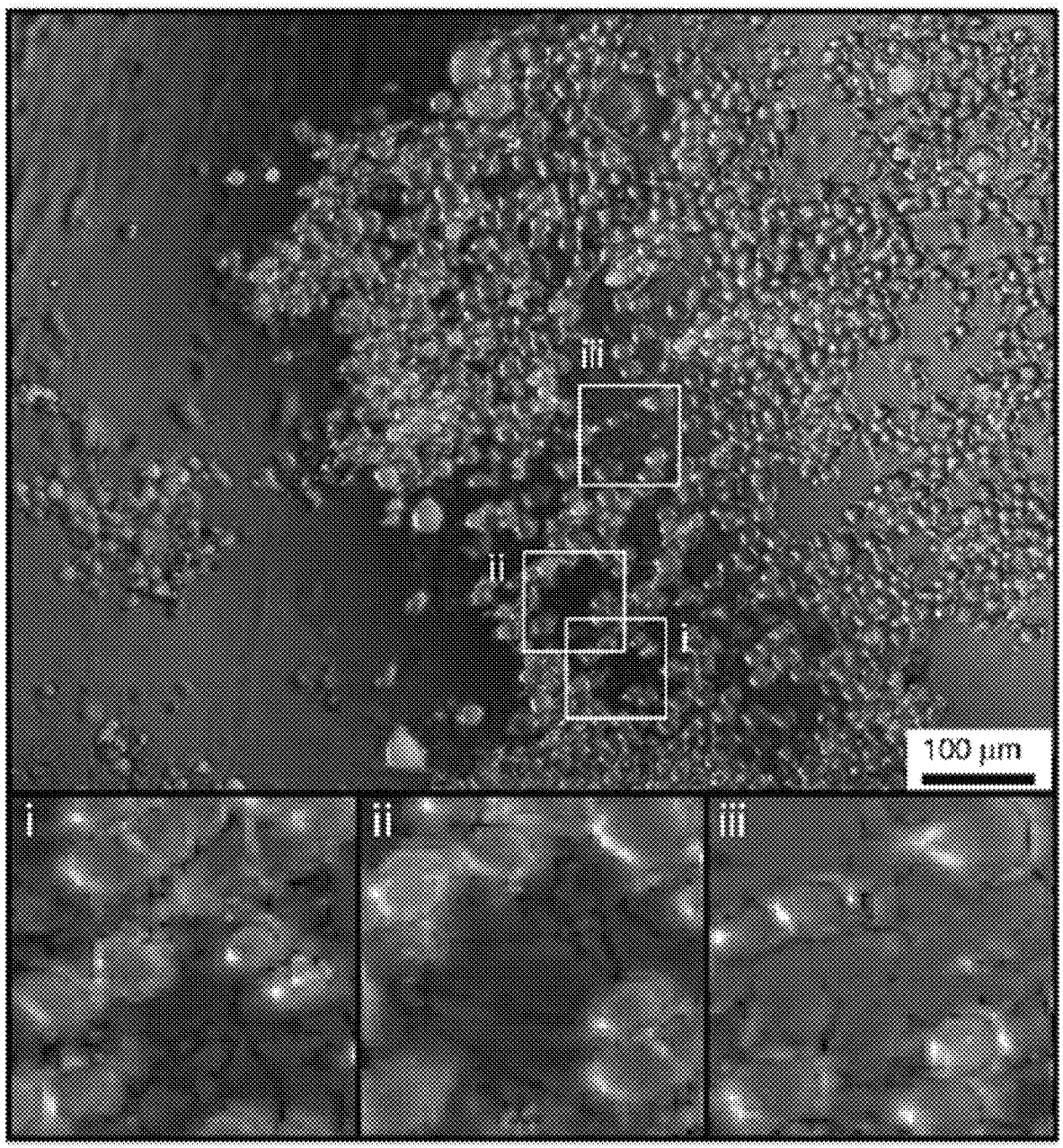
FIG. 11A-FIG. 11B show NG108-15 cells differentiation after exposure to CNTP-LUVs.
Figure 11B:
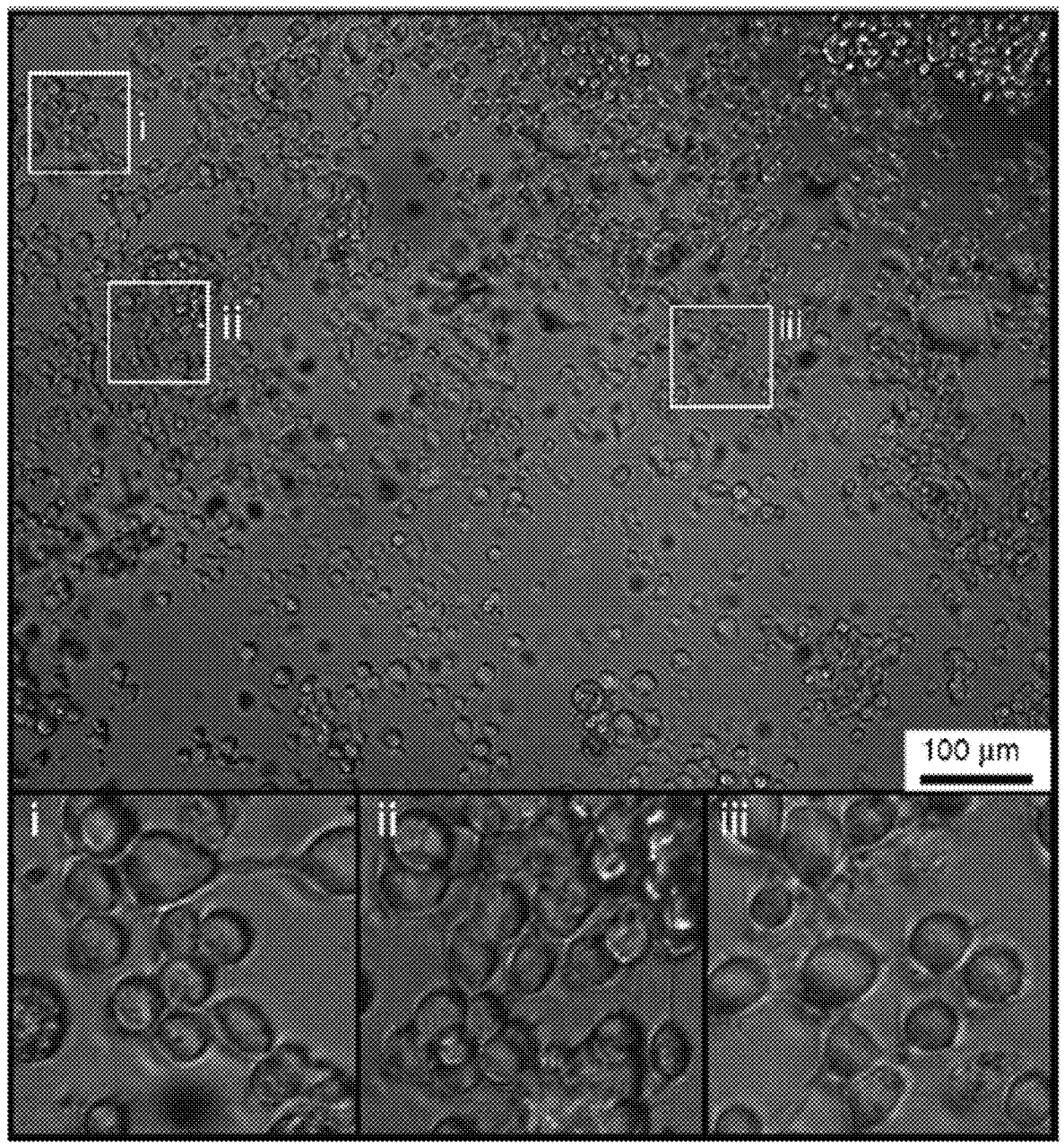

It was also noticed that NG108 cells exposed to free CNTPs and CNTP-LUVs showed a small decrease in the cell proliferation percentage relative to the PBS buffer control. Visual observations of the NG108 cell morphology in the images of those samples showed that cells in the cultures exposed to CNTP and CNTP-LUV were still alive and building neural networks (FIGS. 11A-11B). Literature reports show that neural cell hybrids, such as NG108, can differentiate under certain stresses. Similar to the images of differentiated NG108 cells in the literature, the cultures start to form abundant neurites and varicosities after incubating them with free CNTPs and CNTP-LUVs. By contrast, the control populations of cells exposed only to the PBS buffer looked more flat and circular and had significantly less neurite formations (FIGS. 11A-11B). Thus, it was hypothesized that the cells incubated with CNTP-containing samples started to differentiate instead of growing.

The results reveal a strong propensity for small diameter carbon nanotube porins to facilitate membrane fusion. A combination of kinetic studies and molecular dynamics simulations shows that the fusion process is primarily mediated by the unique geometry of the CNTP dimers, which can distort the adjacent bilayer leaflets to a large degree and then bring together the tails of the inner leaflets across the thin facet of the dimer to complete the critical step in the fusion process. This phenomenon was exploited to construct a liposomal nanoparticles that mimics the functionality of viruses and show that these particles are highly efficient vehicles for delivering a chemotherapeutic agent, doxorubicin, to cancer cells. Further research efforts could optimize the geometry, structure, and delivery efficiency of these vehicles further, leading to more potent and less toxic chemotherapy regimens.

Methods

Materials and Equipment

All the lipids (1,2-dioleoyl-sn-glycero-3-phosphocholine (DOPC), 1-oleoyl-2-6-[(7-nitro-2-1,3-benzoxadiazol-4-yl) amino]hexanoyl-sn-glycero-3-phosphocholine (NBD-DOPC), and cholesterol) were obtained from Avanti. All the other chemicals were purchased from Sigma-Aldrich and used as received, unless specified. Live/Dead assay and MTT cellular assay kits were obtained from Abcam. The size exclusion columns for LUV separation used Sepharose C 160 (Thermo Fisher). The ultra short carbon nanotube porins were created by sonication-assisted cutting of 0.8 nm SWCNT according to the previously published procedure[15]. The fluorescence and absorbance spectra was measured using the Spectramax iD3 Microplate Reader (Molecular Devices). Vesicle size was measured using dynamic light scattering (DLS) setup (Malvern Analytical).

Large Unilamellar Vesicles Formation

The LUVs and CNTP-LUVs were formed and characterized using protocols described in Tunuguntla, et al. Synthesis, lipid membrane incorporation, and ion permeability testing of carbon nanotube porins. *Nat. protocols* 11, 2029 (2016). LUV loaded with DOX were prepared using the dame protocol, but the sonication time was extended to 10 min from 2 min. To form NBD-LUVs about 85% of DOPC and 15% of NBD-DOPC were used, for SRB-LUVs 28 mM sulforhodamine B (SRB) was added to the solution before sonication. All LUVs went through 10 freeze-thaw cycles to remove multilamellar vesicles. LUVs used for drug delivery experiments followed the same protocol, except that the lipid composition was 70% DOPC and 30% cholesterol and the ammonium sulfate 300 mM used instead and the vesicles were extruded using 100 nm membrane filter. In the final step the vesicles were purified on a column conditioned with phosphate-buffered saline (PBS) at pH 7.4. The size of LUVs were determined using DLS. To determine the encapsulating efficiency and monitor DOX leakage from DOX-loaded LUVs and CNTP-LUVs fluorescence kinetics (480ex/590em) was monitored for 18 hours at 37° C.

Lipid Mixing and Content Mixing Assays

To obtain a self-quenched concentration of NBD dye in LUS 15% NBD-DOPC and 85% DOPC mixture were used, as determined from calibration experiments. Lipid fusion assays were performed at different pH (2, 3.15, 4.11, 5.15, 6.11, and 8.7) with buffer pH adjusted with 1 M HCl. In each fusion assay CNTP-LUVs and NBD-LUVs were mixed at 1:1 volume ratio and the fluorescence kinetics (474ex/530em) was recorded for at least 3 hours at a preset temperature maintained by the plate reader. Each assay was repeated at least 3 times. For content mixing assays, CNTP-LUVs were mixed with SRB-LUVs at 1:1 ratio in the presence of tetramethylrhodamine polyclonal antibody from Thermo Fisher to quench the signal from any leaked SRB dye. The amount of antibody used was calculated to quench at least 80% of all SRB dye contained in the sample LUV. The fluorescence kinetics (550ex/595em) was monitored for at least 18 hours at 24° C. All content fusion assays were repeated at least 2 times.

To extract fusion half-times from the fusion kinetics data the fluorescence traces was fitted to the Hill-like equation:

$$F = (1 + (\tau/t)^n)^{-1}$$

where F is normalized fluorescence signal; $\tau$ is the fusion half time; t is the time; and n is Hill coefficient. The fusion rate was then calculated as $2/\tau$. The values of the fit parameter n typically varied between 2 and 3.

DOX Delivery to NG108-15 Cell Using CNTP

NG108-15 cell lines (Mouse neuroblastoma x rat glioma hybrid, obtained from ATCC) were used for the drug delivery experiment. The cells were cultured in growth media (Dulbecco's Modified Eagle Medium 1% Penicillin-Streptomycin and Hypoxanthine-Aminopterin-Thymidine 1× with 10% fetal bovine serum from Gibco) at 37° C. 5% $CO_2$. The cells were seeded in 96-well plate at 5000 cells/well and cultured for 2 days before experiment. Each well was treated with growth media and sample at 1:1 volume ratio for 48 hours.

Cell Viability Quantification Using Live/Dead Assay

The live/dead dye was diluted in PBS to a final concentration of 5× (5 μl in 1 ml of PBS). After exposure to the samples, the media was aspirated from the well and replaced by 100 μl of dye solution. The cells were incubated for 15 minutes. The fluorescent images of cells were recorded using a Leica fluorescence microscope with FITC (494/151 nm) and RHO (528/617 nm) filters to visualize live and dead cells respectively. The number of live and dead cells was counted using ImageJ and normalized to the total number of counted cells. The experiment was repeated 3 times, 3 wells each time, using at least 5 images per well.

Figure 8C:
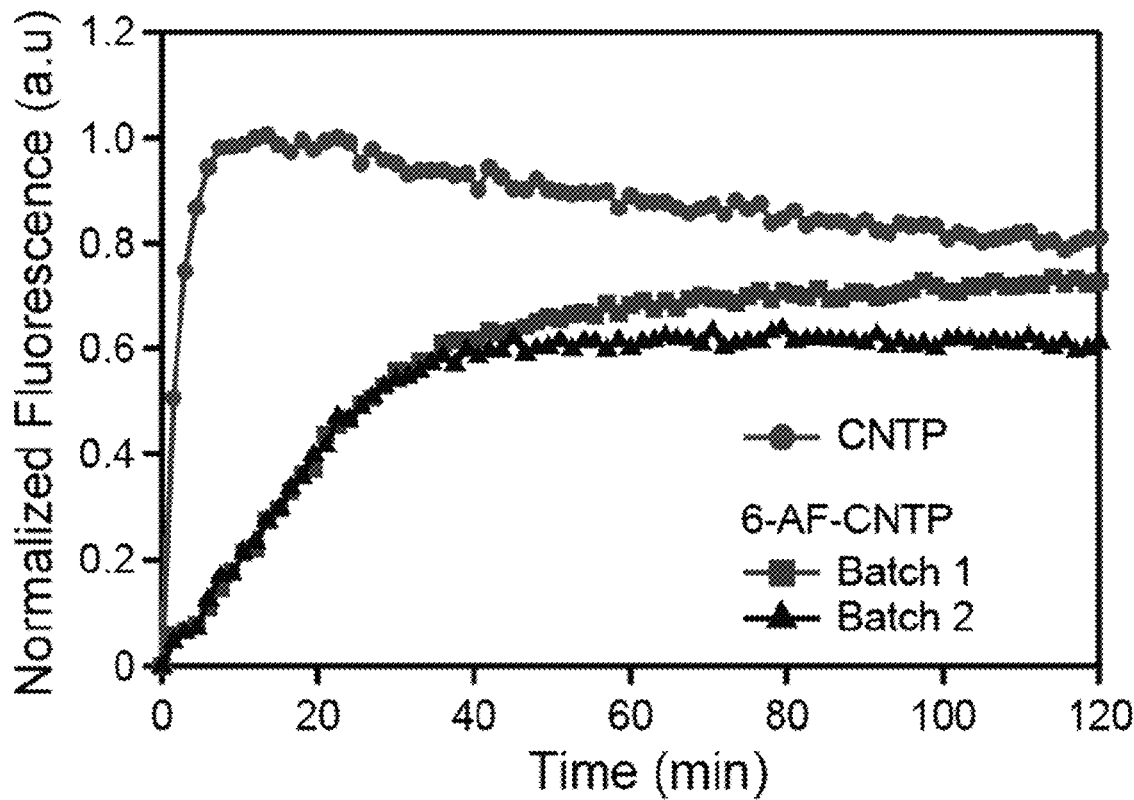
Figure 9A:
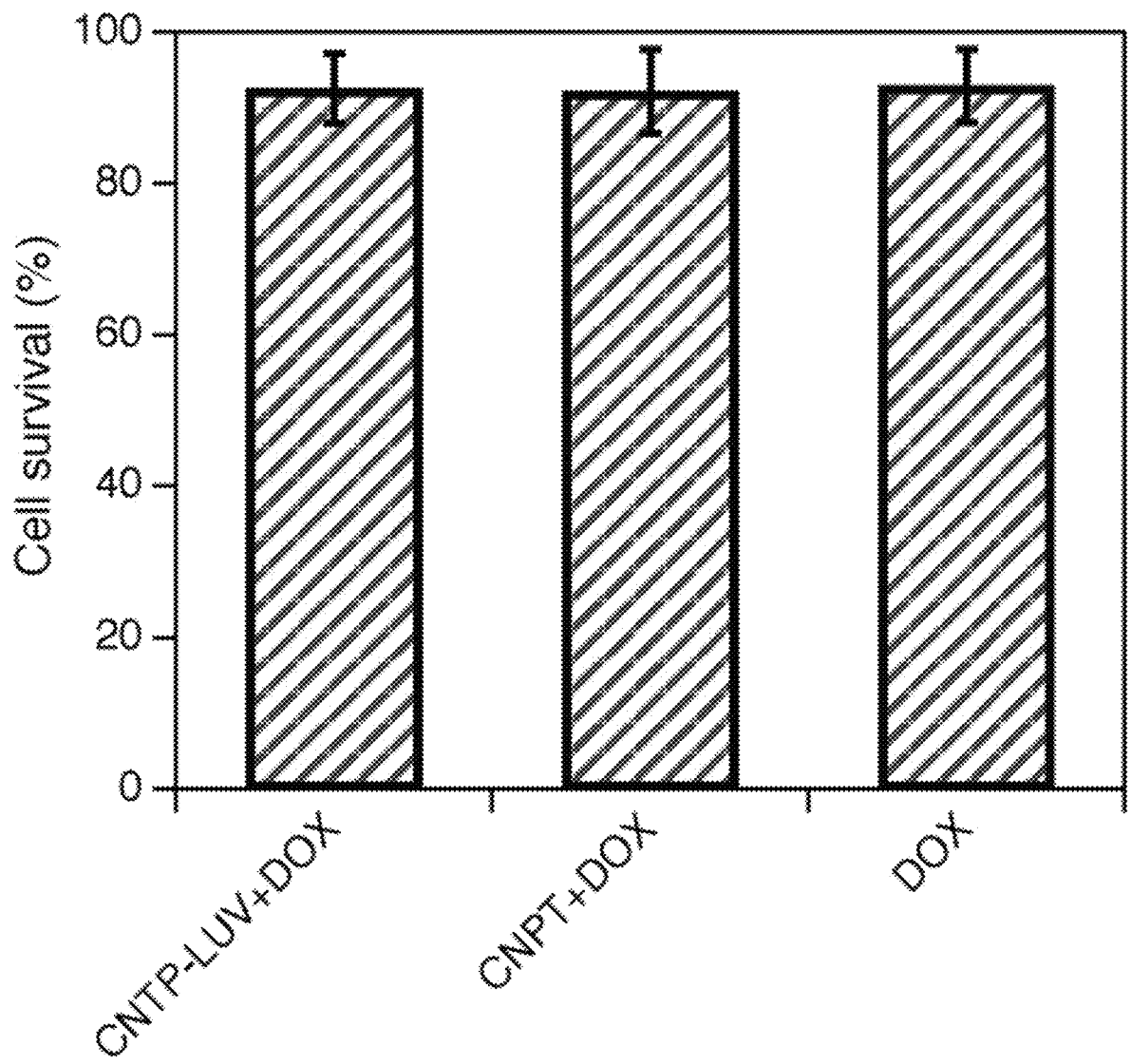
Figure 9C:
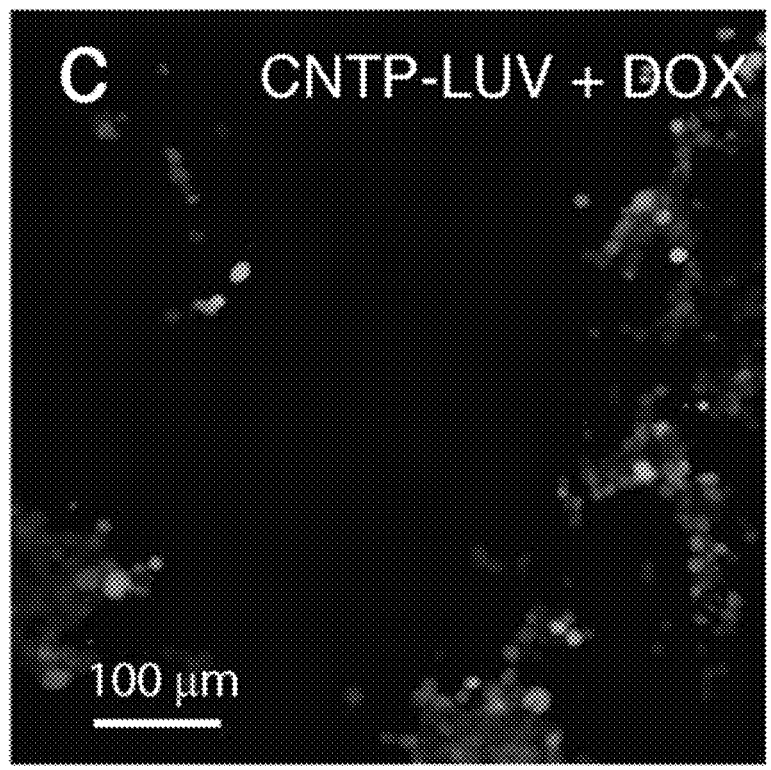
Figure 9D:
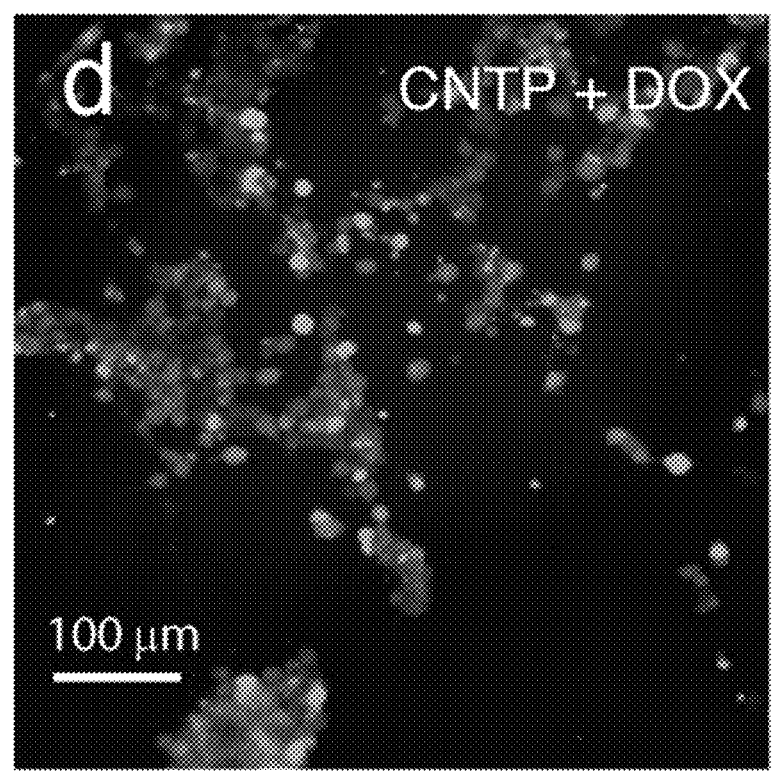
Figure 9E:
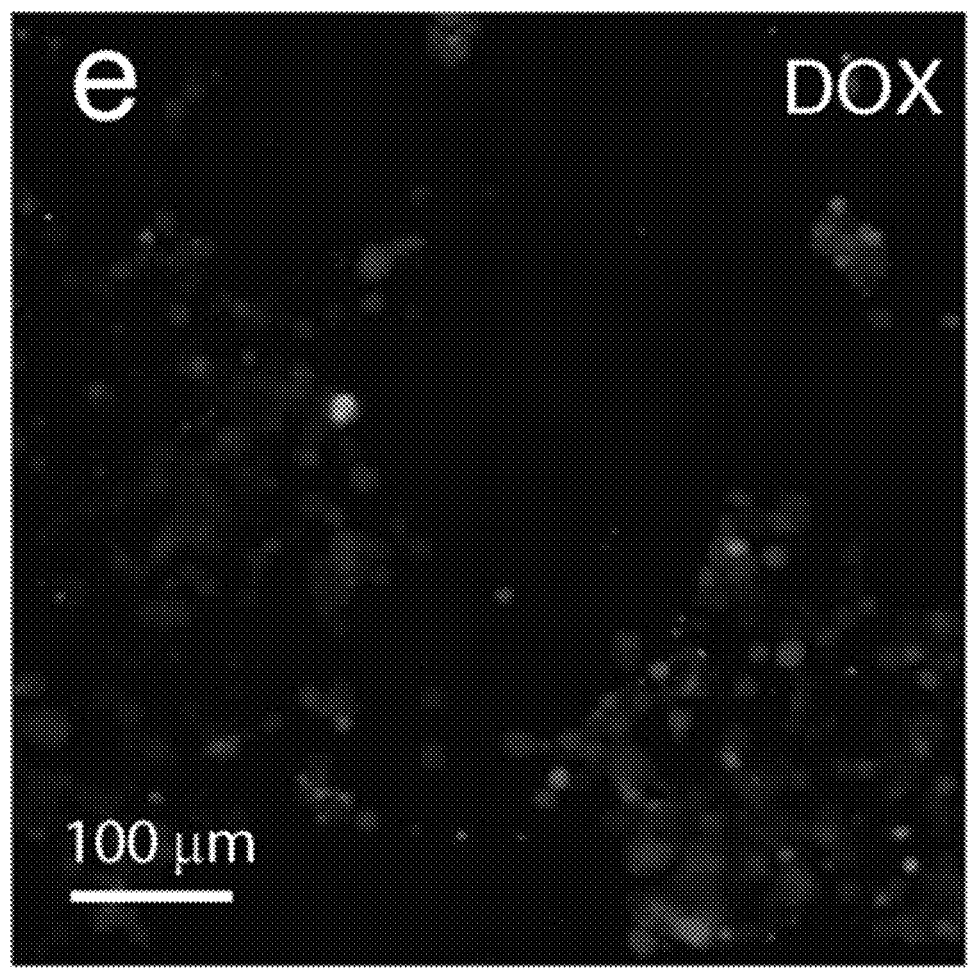
Figure 10A:
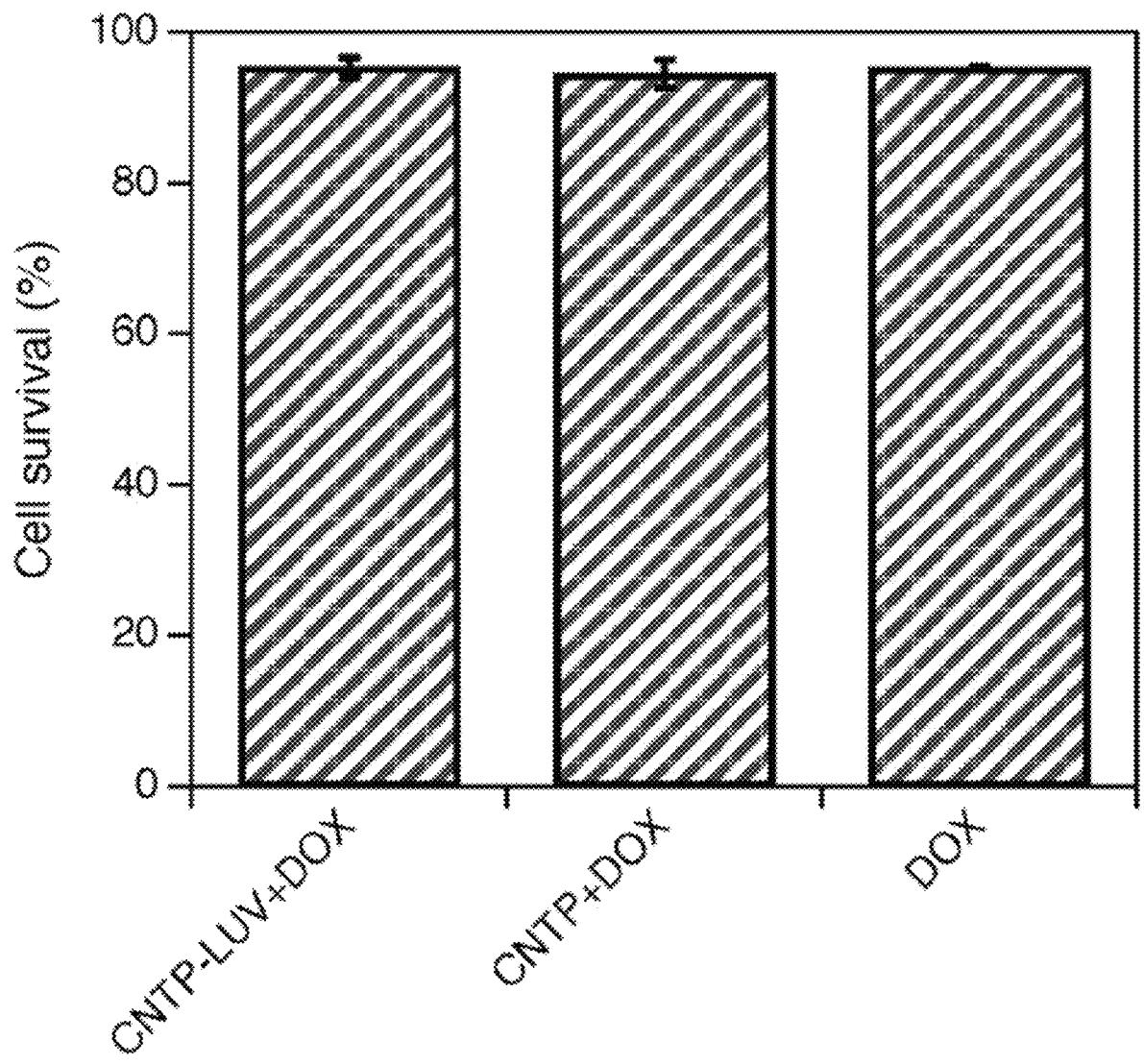
FIG. 10A-FIG. 10E show human breast cancer cells (MDA-MB-231) exposure to free DOX in presence of CNTP-LUVs and free CNTPs.
Figure 10B:
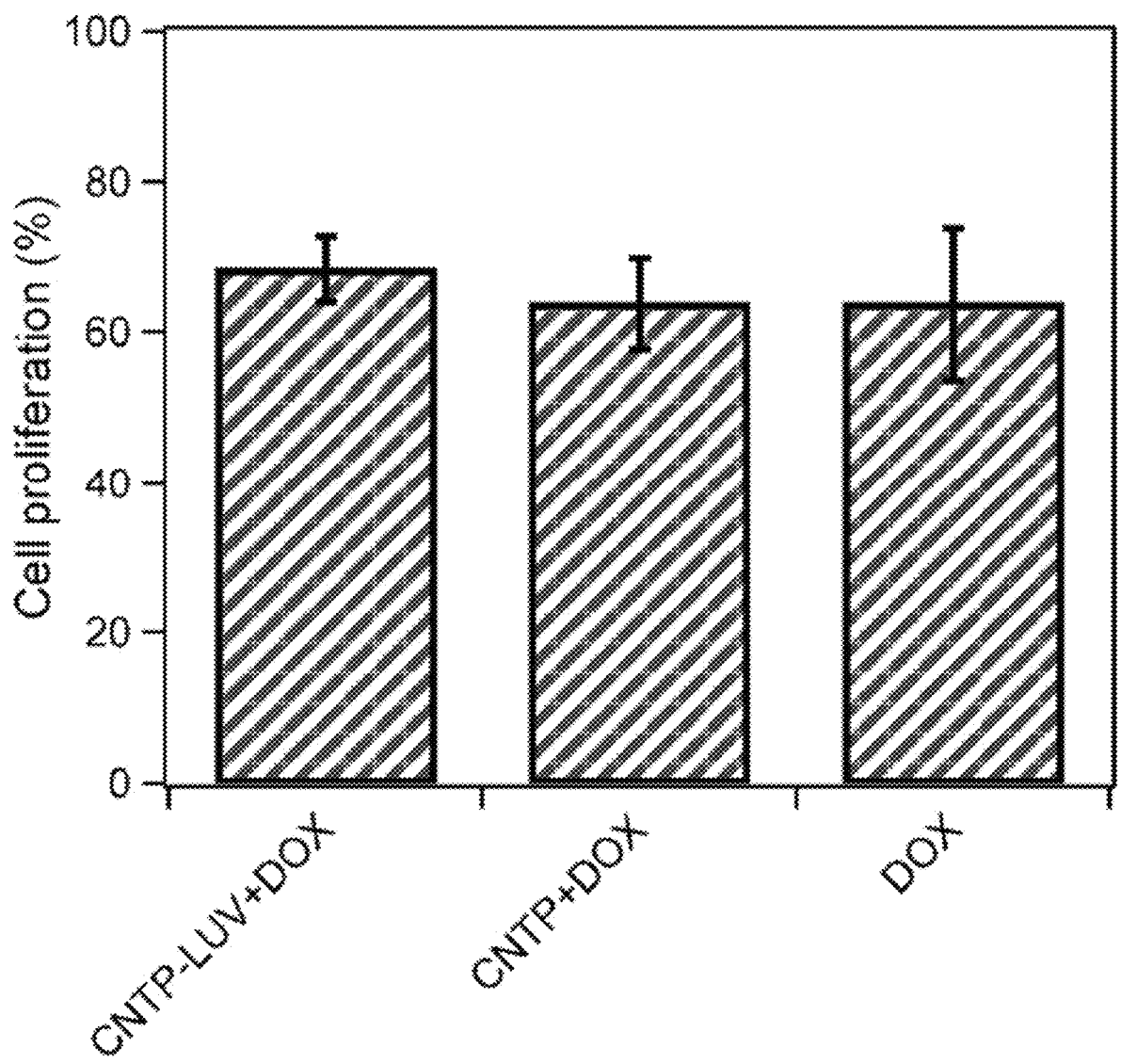
Figure 10C:
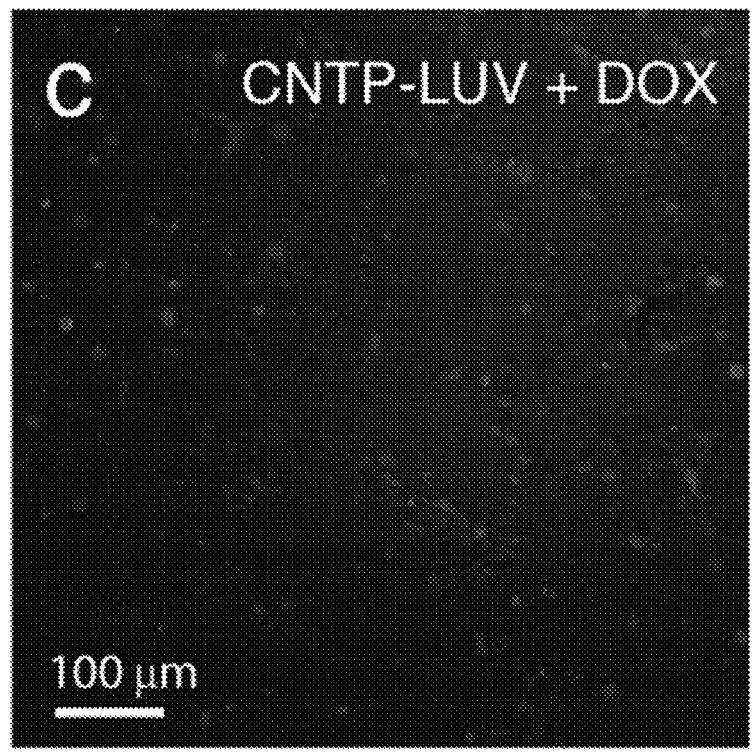
Figure 10D:
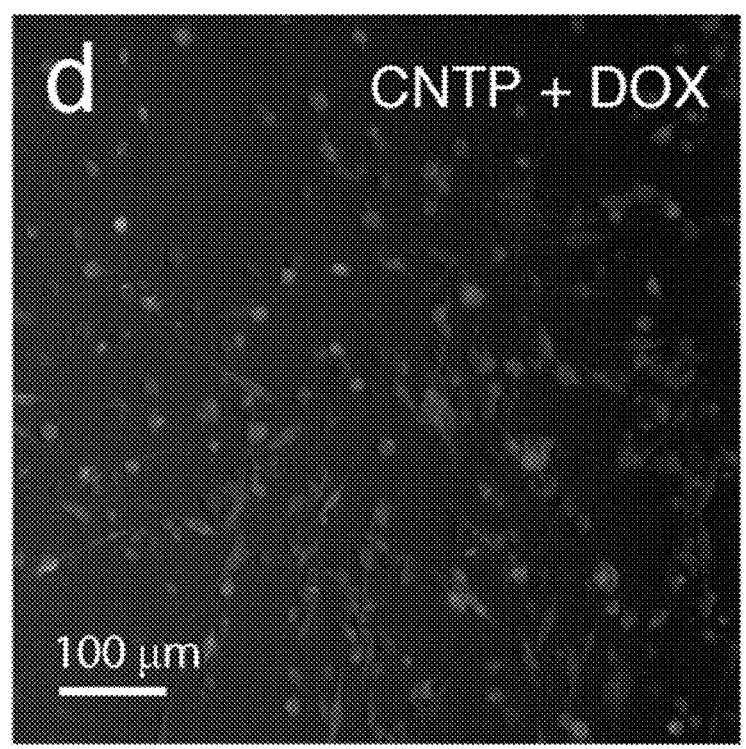
Figure 10E:
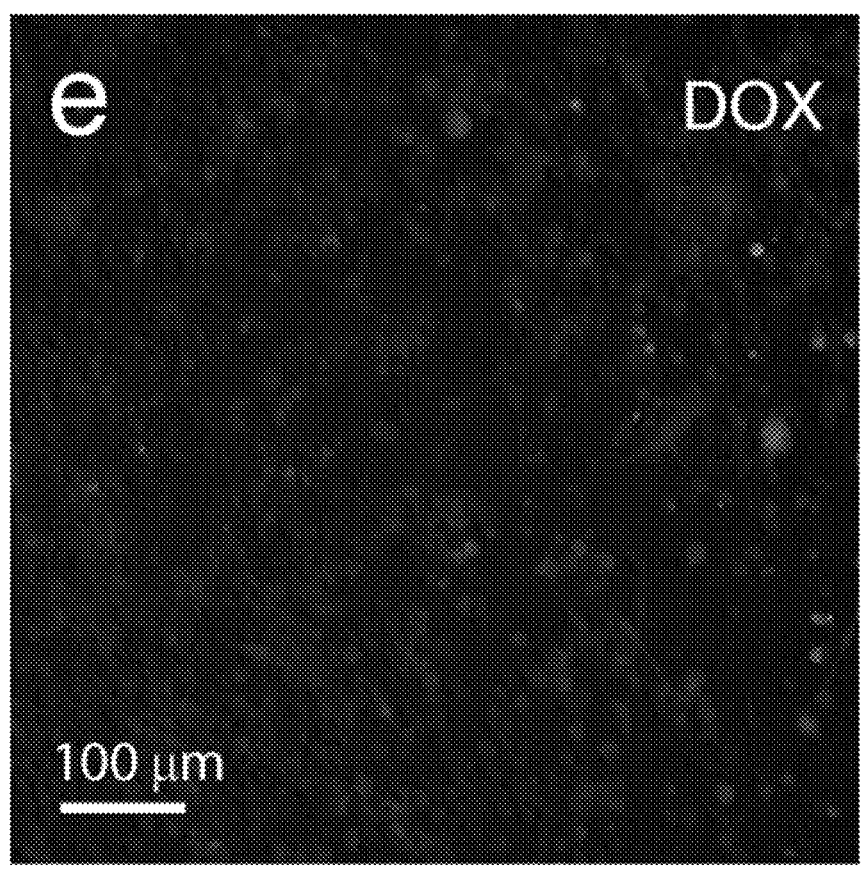

Since the distribution of the samples averages were not normally distributed and the samples size was less 50, Wilcoxon statistical analysis was used to test for significant differences. For some of the experiments quantifying cell response to free CNTPs, CNTPs were modified by covalent coupling of a 6-aminofluorescein (6-AF) dye to the end of the CNTP (see Materials subsection for details). Control experiments indicated that even though this modification produced slower fusion, modified and unmodified CNTPs produced similar outcomes in the fusion experiments at the 1-2 hr timescale (FIG. 8C), which is still much shorter than the 48 hour time scale of the cell viability experiments.

Cell Proliferation Quantification Using MTT Assay

The media with samples were removed from wells and 50 μl of MTT reagent and 50 μl of PBS was added to each well. The cells were incubated at 37° C. for 3 hours. After the incubation, 150 μl of MTT solvent was added into the well. The plate was incubated overnight at room temperature in black box. The absorbance was recorded at 590 nm and used it (after subtracting from background with PBS and MTT reagents) to determine the number of cells in each sample using a calibration curve. The cell proliferation percentage was normalized using PBS-exposed sample as a 100% reference.

Coarse-Grained Molecular Dynamics Simulations

All molecular dynamics simulations were setup and run as described in Bhaskara, et. al., Carbon nanotubes mediate fusion of lipid vesicles. *ACS Nano* 11, 1273-1280 (2017), using the MARTINI (v. 2.3) coarse-grained model. Simulations were performed using GROMACS 2018.7 with the recommended new parameter set for MARTINI simulations: The Verlet neighbor search algorithm was used to update the neighbor list, with the length and update frequency being automatically determined (nstlist=25, rlist=1.259). Lennard-Jones and Coulomb forces were cutoff at 1.1 nm with the potential shifted to 0 using the Verlet-shift potential modifier. Pressure was maintained at 1 bar using the Parrinello-Rahman barostat and temperature was maintained at 300 K using the velocity rescaling algorithm with characteristic coupling times of 12 and 1 ps, respectively.

Thin CNTPs, which are used in this study, consist of 30 rings with 5 beads each, resulting in a total length of 11.8 nm and a diameter of 0.8 nm. For these thin nanotubes the force constant of improper dihedrals, which maintains stiffness, was increased to 550 kJ $mol^{-1}$ $rad^{-2}$. System starting configurations were set up following the protocol for system A of Bhaskara, et. al., Carbon nanotubes mediate fusion of lipid vesicles. *ACS Nano* 11, 1273-1280 (2017), where two 15 nm DOPC vesicles were stapled by thin CNT monomer, dimer and trimer, respectively (see FIG. 4A-FIG. 4C). The number asymmetry was varied by removing lipids from the inner leaflets of both vesicles, respectively. All simulated systems are summarized in Table 1. For each setup, 30 replicates were run with different initial velocities.

TABLE 1

Summary of the systems used to simulate CNTP-mediated vesicle fusion

| CNTP | DOPC Lipids ($N_{inner}/N_{outer}$) | Box Sizes [$nm^3$] | Particles | Time [μs] | Replicas |
|---|---|---|---|---|---|
| monomer | $r_1$ = 697/1308 $r_2$ = 696/1311 | 26 × 25 × 46 | 249455 | 1.7 | 30 |
| monomer | $r_1$ = 687/1308 $r_2$ = 686/1311 | 26 × 25 × 46 | 249175 | 1.7 | 30 |
| monomer | $r_1$ = 677/1308 $r_2$ = 676/1311 | 26 × 25 × 46 | 248895 | 1.7 | 30 |
| monomer | $r_1$ = 667/1308 $r_2$ = 666/1311 | 26 × 25 × 46 | 249735 | 1.7 | 30 |
| dimer | $r_1$ = 697/1308 $r_2$ = 696/1311 | 26 × 25 × 46 | 249885 | 1.7 | 30 |
| dimer | $r_1$ = 687/1308 $r_2$ = 686/1311 | 26 × 25 × 46 | 249605 | 1.7 | 30 |
| dimer | $r_1$ = 677/1308 $r_2$ = 676/1311 | 26 × 25 × 46 | 249325 | 1.7 | 30 |
| dimer | $r_1$ = 667/1308 $r_2$ = 666/1311 | 26 × 25 × 46 | 249045 | 1.7 | 30 |

TABLE 1-continued

Summary of the systems used to simulate CNTP-mediated vesicle fusion

| CNTP | DOPC Lipids ($N_{inner}/N_{outer}$) | Box Sizes [nm³] | Particles | Time [μs] | Replicas |
|---|---|---|---|---|---|
| trimer | $r_1$ = 697/1308<br>$r_2$ = 696/1311 | 26 × 25 × 46 | 250035 | 1.7 | 30 |
| trimer | $r_1$ = 687/1308<br>$r_2$ = 686/1311 | 26 × 25 × 46 | 249755 | 1.7 | 30 |
| trimer | $r_1$ = 677/1308<br>$r_2$ = 676/1311 | 26 × 25 × 46 | 249475 | 1.7 | 30 |
| trimer | $r_1$ = 667/1308<br>$r_2$ = 666/1311 | 26 × 25 × 46 | 249195 | 1.7 | 30 |

Example 3—Cell Viability Assays Using an Exemplary Engineered Lipid-Based Vesicle The large unilamellar vesicle is generated following the method described in Example 2. Rat and mouse neuroblastoma and glioma cells were utilized in this experiment. Doxorubicin was used as the exemplary payload. The concentration of the stock was about 100 μg/mL and the encapsulation was from about 2-7 μg/mL.

The cells were treated with the engineered lipid-based vesicle comprising the doxorubicin payload for about 48 hours. The media to drug ratio was 1:1 ratio.

Figure 12A:
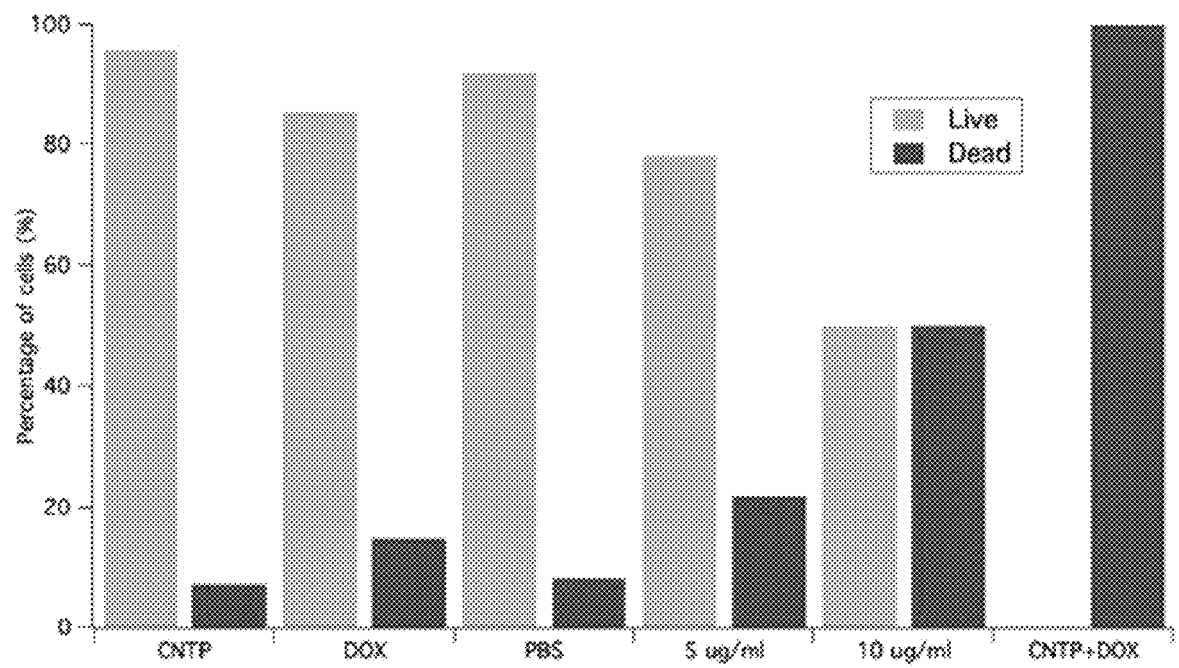
FIG. 12A illustrates a fluorescent assay showing the percentage of live and dead cells.

FIG. 12A illustrates a live and dead cell assay. As shown here, cell viability was about 0% in the presence of the engineered lipid-based vesicle encapsulated with doxorubicin (CNTP+DOX).

Figure 12B:
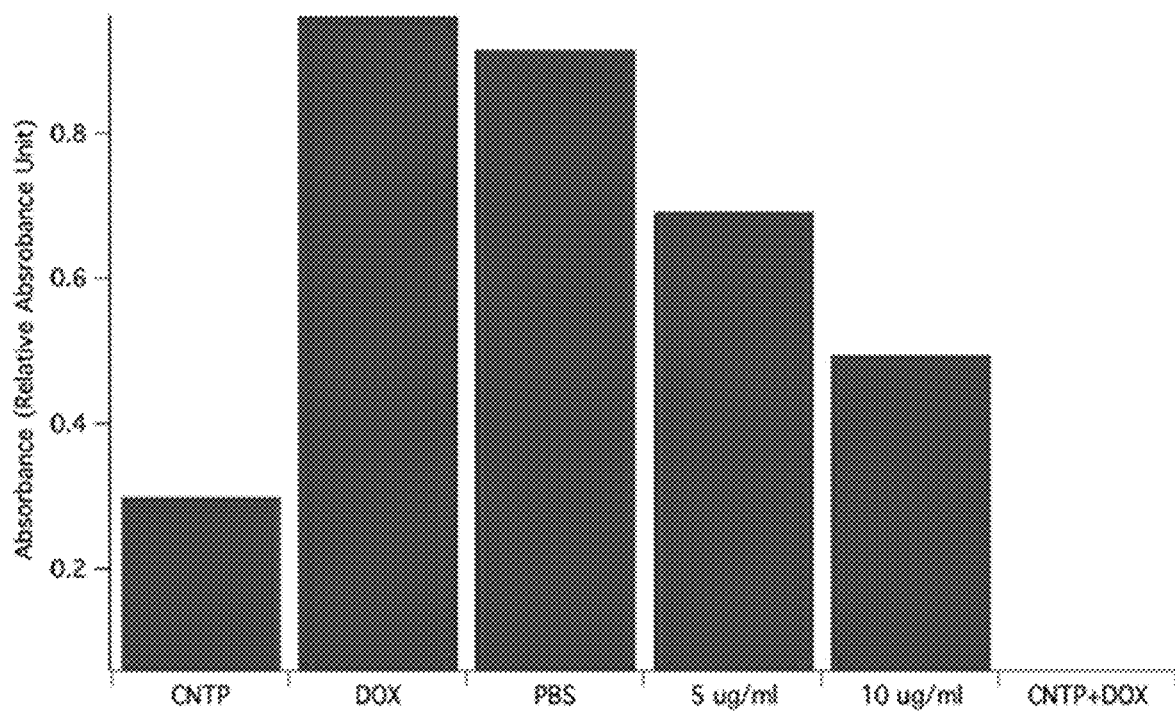
FIG. 12B illustrates a MTT cell proliferation assay.

FIG. 12B illustrates a MTT cell proliferation assay. As shown here, viable cells were not detected under the presence of CNTP+DOX. It is noted that CNTP may induced a potential cell change from growth state to differentiation state.

Example 4—Manufacture of an Exemplary Engineered Lipid-Based Vesicle Comprising a Boron Nitride Nanotube Complex The large unilamellar vesicle is generated following the method described Tunuguntla, et al., "Synthesis, lipid membrane incorporation, and ion permeability testing of carbon nanotube porins," *Nature Protocols* 11(10): 2029-2047 (2016). In brief, the boron nitride nanotube (BNNT) is purified based on a thermogravimetric analysis (TGA) method to produce purified BNNT. Next, the BNNT is solubilized into an aqueous phase, sonicated in the presence of lipids (e.g., DOPC), and then hydrated with BNNT powder. Shortening of the BNNTs is carried out by probe microtip sonication.

Example 5—Membrane Fusion and Drug Delivery with Carbon Nanotube Porins

Different types of virus membrane-fusion protein (class I, II, III, and IV) can facilitate vesicle fusion. Class I fusion proteins have a rod-like shape when the protein inserts to the lipid membrane. The structure and the dimension is similar to the SWCNT (10 nm in length, about 1 nm in diameter).

Figure 13:
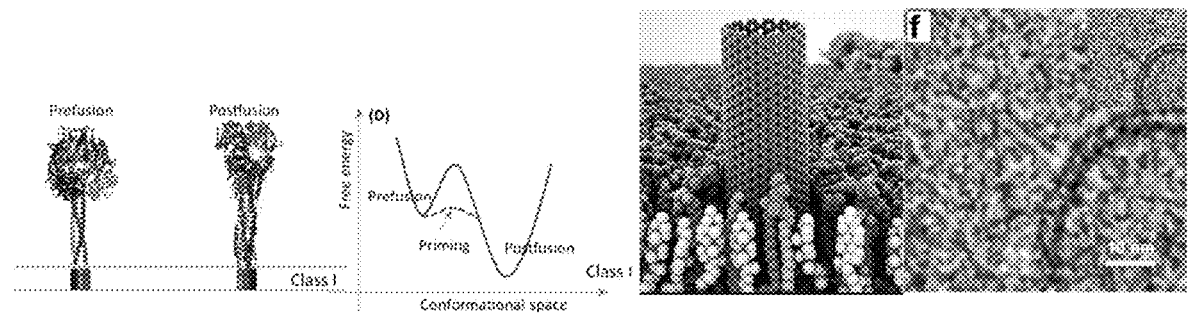
FIG. 13 illustrates the characteristics of class I proteins which are similar to CNT structure.

Class I proteins are apolar with many hydrophobic regions with the size around about 1 nm in diameter. Hydrophobic regions is normally inside the protein and exposed to the outside during the fusion process to facilitate the insertion of the protein into the lipid membrane. See FIG. 13, which illustrates the characteristics of class I proteins which are similar to CNT structure.

NBD-DOPC was used to observe the fusion process on the membrane. At 15% NBD-DOPC LUV, the NBD starts to dequench when diluted due to fusion of vesicles. Fusion kinetics of 200 nm LUVs was observed at different temperatures to determine fusion activation energy.

Figure 14:
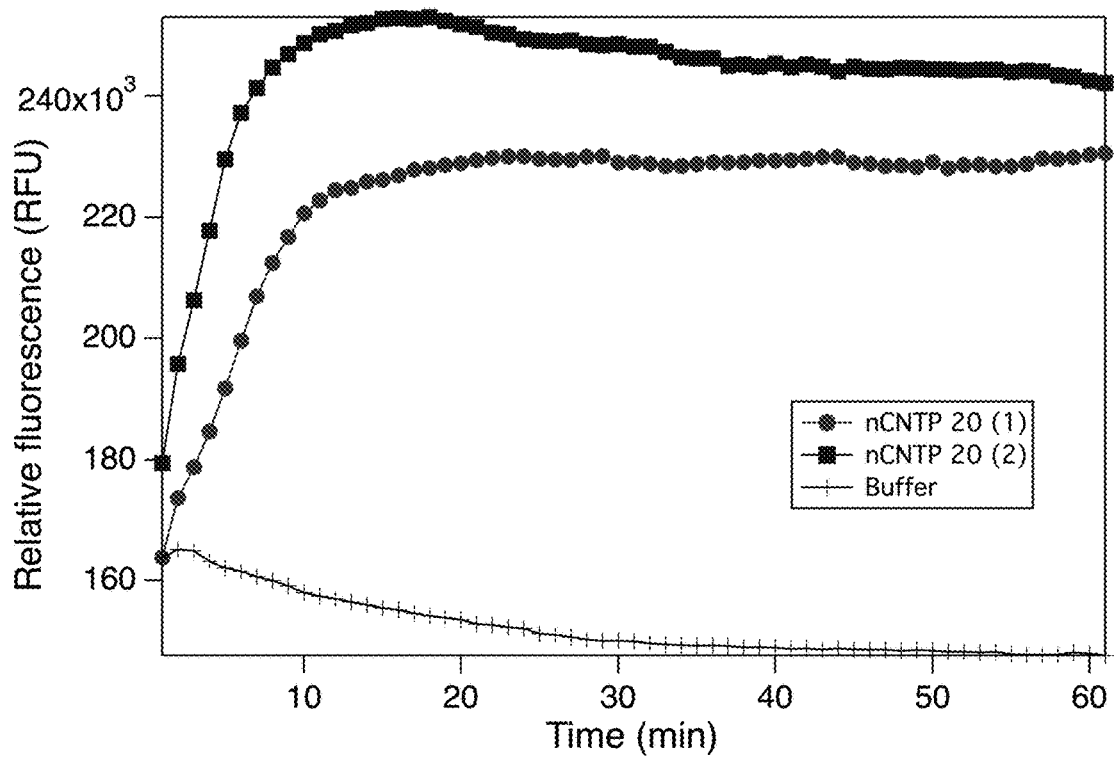
FIG. 14 illustrates NBD dye dequenching over time.

FIG. 14 illustrates NBD dye dequench over time which indicates fusion. The CNTP was inserted in LUV and mixed with NBD-LUV. The increase in fluorescence of NBD indicates that two populations of vesicles were fusing. The fusion timescale depends on the number of CNTP per LUV.

Figure 15:
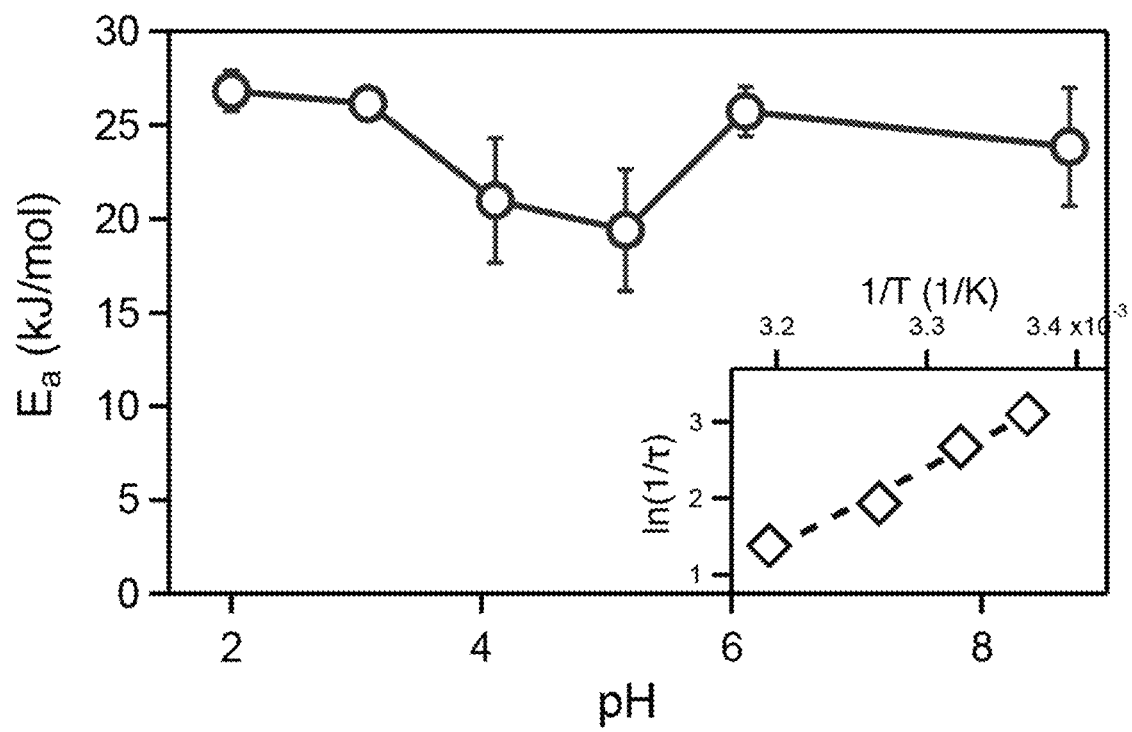
FIG. 15 illustrates activation energy barrier for CNTP-facilitated fusion.

FIG. 15 illustrates activation energy barrier for CNTP-facilitated fusion. Reaction kinetics follows Arrhenius dependence with $E_a$~25 kJ/mole (ca. 10 $k_BT$). Activation energy is slightly lower at pH~5 which close to pKa of CNTP. CNTP activation energy is significantly lower than just lipid vesicle fusion (85 kJ/mol).

Figure 16:
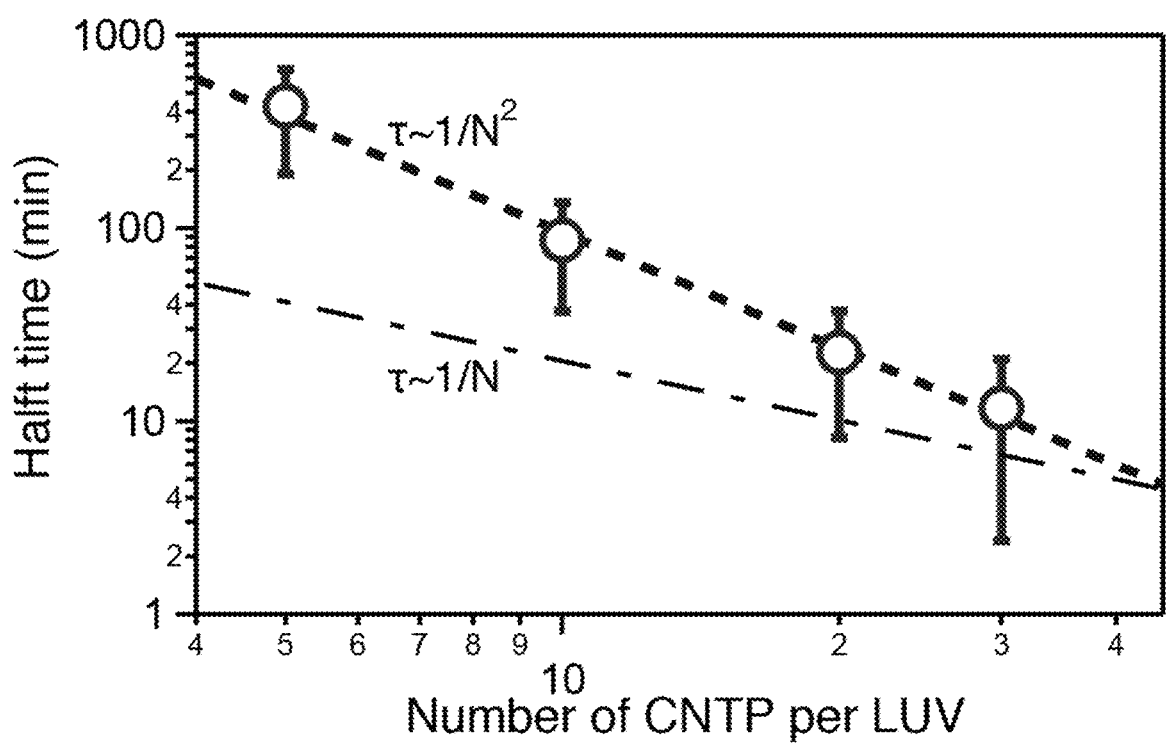
FIG. 16 illustrates dimerization of sub-nm CNTP required for the initiation of fusion.

FIG. 16 illustrates dimerization of sub-nm CNTP required for the initiation of fusion. CNTP-facilitated fusion follows second order reaction kinetics. CNTP form dimers during the fusion process. This is similar to viral fusion (usually required at least 2 proteins at the fusion site).

Figure 17:
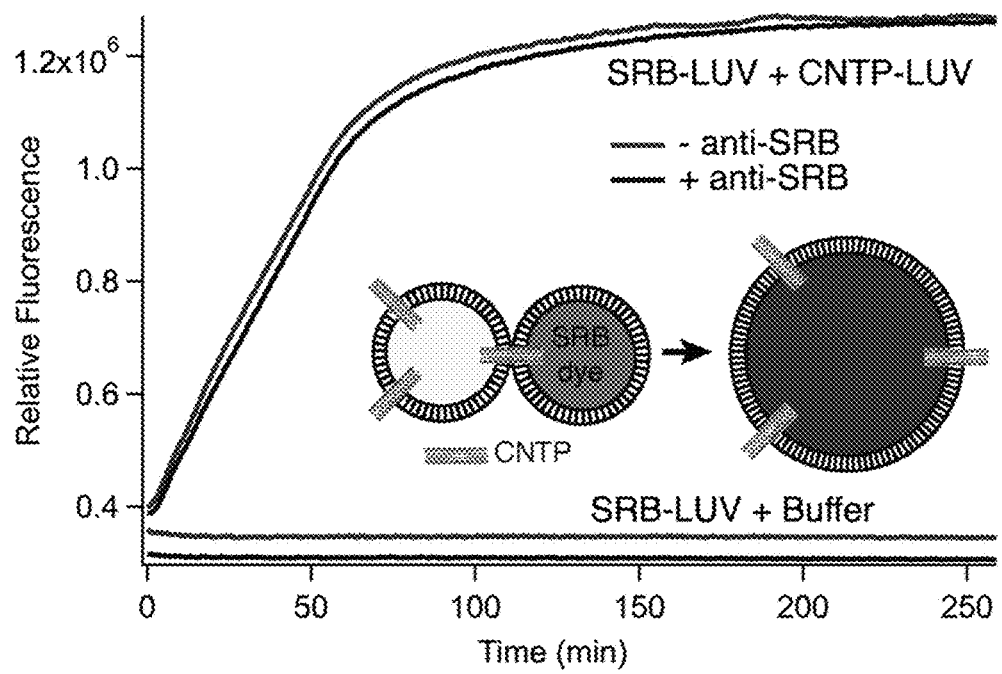
FIG. 17 illustrates SRB content mixing assay to show full fusion facilitated by CNTP.

FIG. 17 illustrates SRB content mixing assay to show full fusion facilitated by CNTP. SRB dye dequenches after content mixing with the cargo from CNTP-LUV. The fusion time in content mixing assay was twice of the one in lipid mixing assay. The outer lipid membrane fused faster than the inner membrane. TRITC antibody was added in the assay to detect the leakage of SRB content to the solution, but the difference between the assay with and without antibody was insignificant (~5%).

Figure 18:
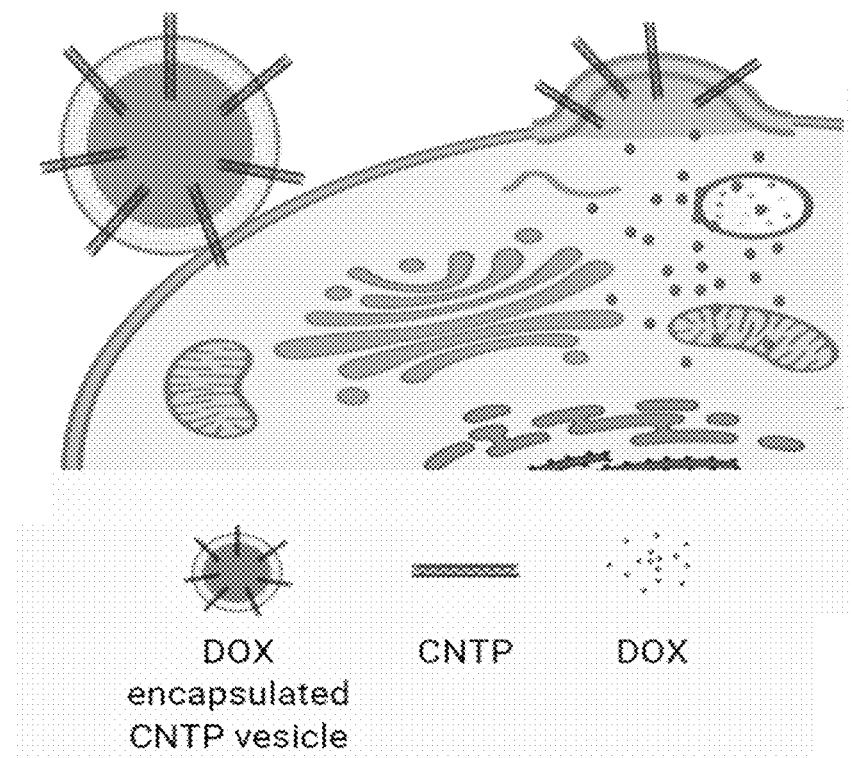
FIG. 18 illustrates drug delivery to cancer cells using CNTP-facilitated fusion.

FIG. 18 illustrates drug delivery to cancer cells using CNTP-facilitated fusion. NG108-15 cell lines (Mouse neuroblastoma x rat glioma hybrid) was used. Doxorubicin (DOX) was delivered to the cells as: free DOX; LUV encapsulating DOCX; or CNTP-LUV encapsulating DOX. The cytotoxicity of CNTP was also evaluated. Cell viability was measured using live/dead assay and MTT assay.

Figure 19:
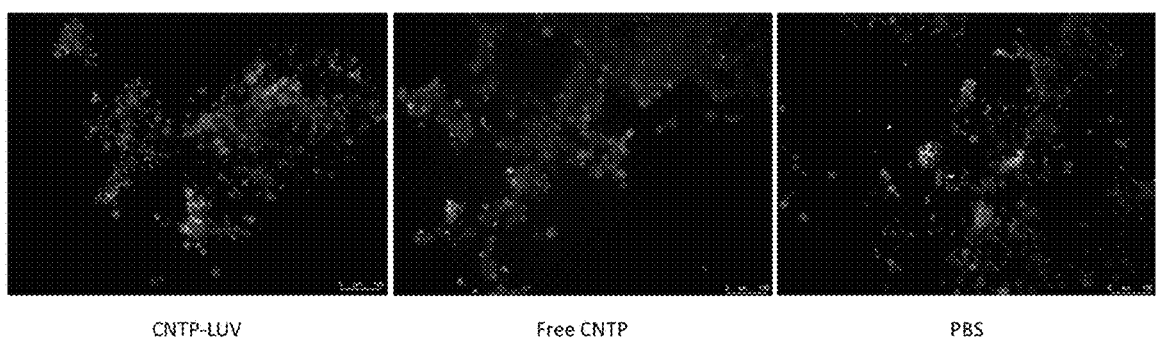
FIG. 19 shows CNTP cytotoxicity.

FIG. 19 shows CNTP cytotoxicity. Based on the live/dead assay, the cell viability of free CNPT and CNTP-LUV was similar to the control (PBS). No significant cytotoxicity has been observed.

Figure 20:
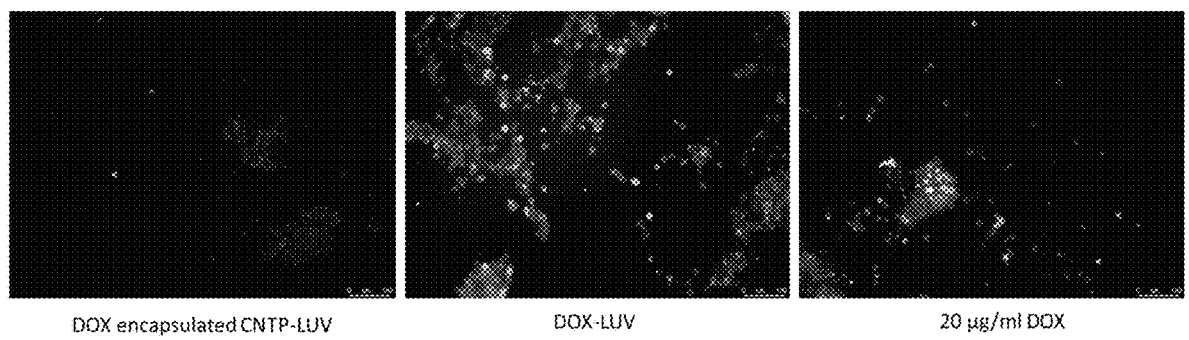
FIG. 20 shows drug delivery using CNTP-mediated fusion.

FIG. 20 shows drug delivery using CNTP-mediated fusion. Cells exposed to CNTP-LUV-DOX had much lower cell viability compared to DOX-LUV at same concentration range. Percentage of live cells exposed to CNTP-LUV-DOX (10 μg/ml encapsulation concentration) was lower than 20 μg/ml of free DOX.

Figure 21:
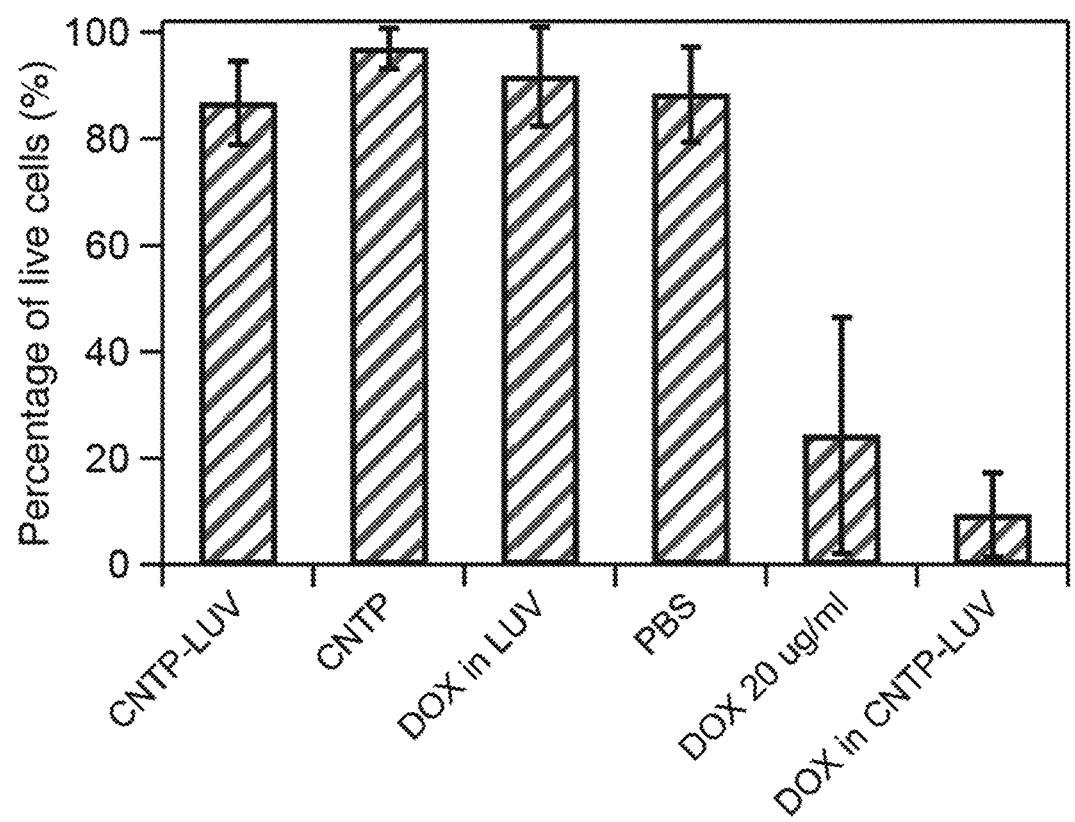
FIG. 21 shows the results from a live and dead assay.

FIG. 21 shows the results from a live and dead assay. CNTP-LUV with encapsulated DOX outperformed DOX-LUV at very low concentration of DOX (9% vs 90%). For Doxil, the cell viability is much lower (<20%) but the encapsulation concentration is around 1 mg/ml, which can lead to deaths of surrounding cells.

Figure 22:
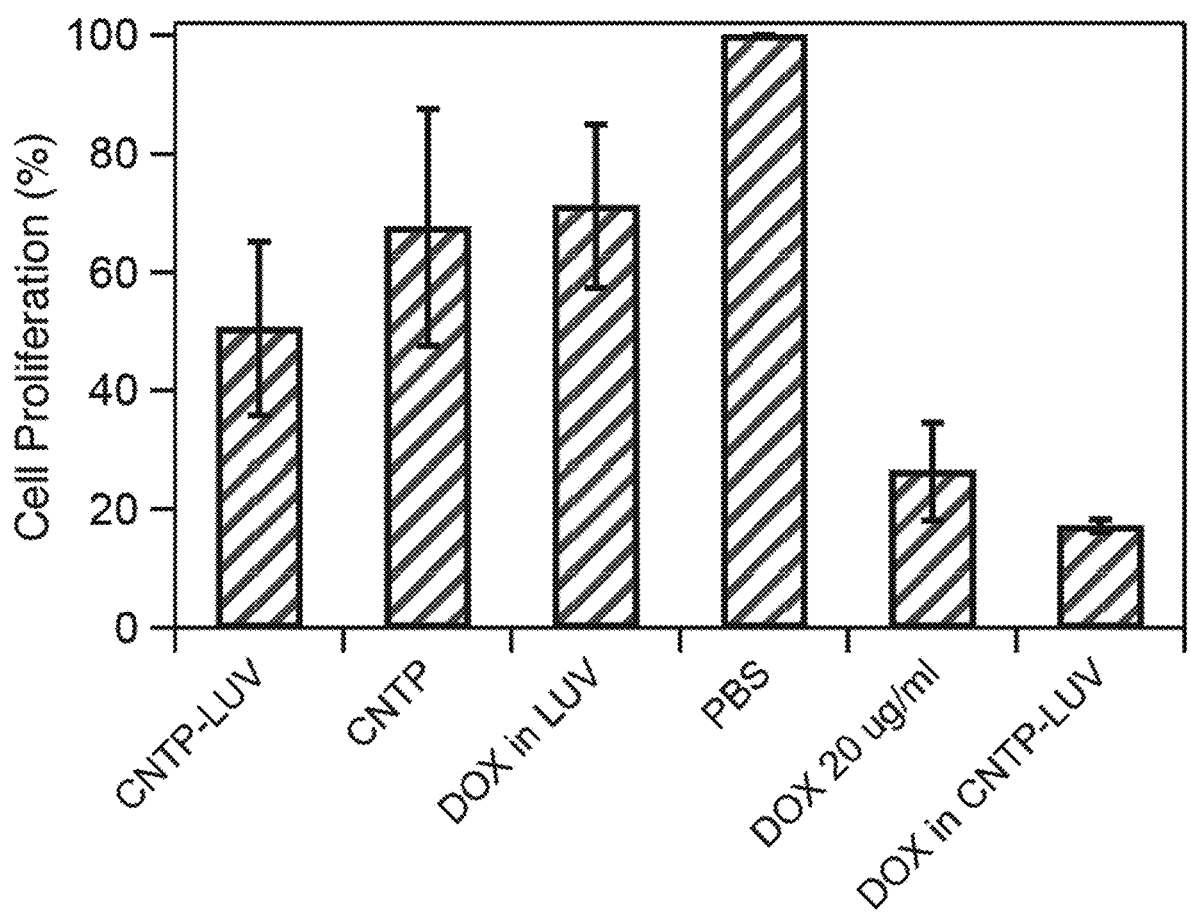
FIG. 22 shows a MTT assay.

FIG. 22 shows a MTT assay. MTT assay showed the percentage of cell proliferation. CNTP-LUV and free CNTP show lower cell proliferation even though cells were alive and forming neural networks. Cell may differentiate instead of growing un the presence of CNTP. CNTP may be cytostatic to cells In conclusion, CNTP facilitated the full fusion of lipid vesicles on a ca. 1 hour timescale. Fusion activation energy of CNTP is much lower than that of the pure lipid vesicles. pH change has only a small effect on fusion activation energy. CNTP can be used to deliver cancer drug to cells at lower concentration than DOX-LUV and had better performance than free DOX.

Example 6—Nucleic Acid Encapsulated Nanoparticles

This example provides a method to encapsulate nucleic acids (DNA and/or RNA) as a nanoparticle cargo. A mixture of cationic lipids and DOPE at 50%:50% ratio is dried under vacuum for at least 1 h. In parallel, an aliquot of the CNTP stock solution (calculated to arrive at the desired number of CNTP per vesicle) is dried in the vacuum evaporator for 1 h. Then, the resulting CNTP pellet is resuspended in 500 µl of KCl 150 mM at pH 4.5 that contained 30 µg of mRNA. The resulting solution is then used to rehydrate the dried lipid mixture. The combined solution is then vortexed for 30 seconds to form the lipid vesicles encapsulating the nucleic acids. These vesicles are incubated at 4° C. for 30 minutes and extruded through a 100 nm membrane filter. In the final step the vesicles are purified on a Sepharose CL-6B column conditioned with phosphate-buffered saline (PBS) at pH 7.4. The size of LUVs is determined using Dynamic Light Scattering. Quan-iT Ribogreen RNA assay (Thermo Fisher) is used to determine the amount of nucleic acids inside the vesicles and the total amount of nucleic acids in the solution and the corresponding mRNA encapsulation efficiency. After that, the CNTP vesicles encapsulating mRNA are incubated with cells for 48 hours to allow the transfection of nucleic acids to the cells. The efficiency of the transfection and resulting protein production by the cells can be quantified by optical techniques.

EMBODIMENTS

Embodiment 1: A method of delivering a payload to a cell, comprising contacting the cell with an engineered lipid-based vesicle comprising a nanotube dimer embedded within the lipid bilayer circumference of the lipid-based vesicle and a payload, wherein the nanotube dimer induces fusion of the engineered lipid-based vesicle and the cell, thereby delivering the payload to the cell.

Embodiment 2: The method of embodiment 1, wherein the engineered lipid-based vesicle has a diameter of at least 28 nm, at least 30 nm, at least 35 nm, at least 40 nm, at least 50 nm, at least 100 nm, at least 200 nm, or larger.

Embodiment 3: The method of embodiment 1 or 2, wherein the engineered lipid-based vesicle is a liposome, optionally selected from a multilamellar vesicle (MLV), small unilamellar liposome vesicle (SUV), large unilamellar vesicle (LUV), giant unilamellar liposome (GUV), or a cochleate vesicle.

Embodiment 4: The method of any one of the embodiments 1-3, wherein the liposome comprises a natural phospholipid, a synthetic phospholipid, an unsaturated lipid, a saturated lipid, a lysolipid, a sphingolipid, a glycosphingolipid, a steroid, a charge-inducing lipid, or a combination thereof.

Embodiment 5: The method of embodiment 4, wherein the natural phospholipid comprises phosphotidylcholine, phosphotidylserine, phosphotidylethanolamine, or phosphatidylinositol.

Embodiment 6: The method of embodiment 4, wherein the synthetic phospholipid comprises phosphatidic acid, phosphatidylcholine, phosphatidylglycerol, phosphatidylethanolamine, phosphatidylserine, or PEG phospholipid.

Embodiment 7: The method of embodiment 4 or 6, wherein the synthetic phospholipid comprises DEPA-NA, DLPA-NA, DMPA-NA, DOPA-NA, DPPA-NA, DSPA-NA, DEPE, DLPE, DMPE, DOPE, DPPE, DSPE, POPE, DLPS-NA, DMPS-NA, DOPS-NA, DPPS-NA, DSPS-NA, DDPC, DEPC, DLOPC, DLPC, DMPC, DOPC, DPPC, DSPC, LYSOPC MYRISTIC, LYSOPC PALMITIC, LYSOPC STEARIC, Milk Sphingomyelin MPPC, MSPC, PMPC, POPC, PSPC, SMPC, SOPC, SPPC, DEPG-NA, DLPG-NA, DLPG-NH4, DMPG-NA, DMPG-NH4, DMPG-NH4/NA, DOPG-NA, DPPG-NA, DPPG-NH4, DSPG-NA, DSPG-NH4, POPG-NA, HSPC, or a combination thereof.

Embodiment 8: The method of embodiment 4, wherein the unsaturated lipid comprises 1-stearoyl-2-linoleoyl-sn-glycero-3-[phosphor-L-serine] or dioleaylphosphtidylcholine.

Embodiment 9: The method of embodiment 4, wherein the sphingolipid comprises sphingomyelin.

Embodiment 10: The method of embodiment 4, wherein the glycosphingolipid comprises ganglioside.

Embodiment 11: The method of embodiment 4, wherein the steroid comprises cholesterol or a cholesterol derivative, wherein the cholesterol derivative is optionally DC-cholesterol.

Embodiment 12: The method of embodiment 4, wherein the charge-inducing lipid comprises diotadecyldimethyl ammonium bromide/chloride (DODAB/C), dioleoyl trimethylammonium propane (DOTAP), or ionizable lipids (DLIN-MC3-DMA).

Embodiment 13: The method of embodiment 1 or 2, wherein the lipid-based vesicle is an extracellular vesicle (EV), optionally an exosome or a microvesicle.

Embodiment 14: The method of any one of the embodiments 1-13, wherein the nanotube dimer comprises a carbon nanotube dimer, a boron nitride nanotube (BNNT) dimer, a $MoS_2$ nanotube dimer, a $MoS_2$-carbon nanotube hybrid dimer, or a carbon-$MoS_2$—$WS_2$ nanotube hybrid dimer.

Embodiment 15: The method of any one of the embodiments 1-14, wherein the carbon nanotube dimer is a single-walled carbon nanotube (SWCNT) dimer, optionally a conjugated SWCNT dimer.

Embodiment 16: The method of any one of the embodiments 1-15, wherein the SWCNT dimer comprises a total inner diameter across the major axis of the dimer of from about 0.8 nm to about 2.8 nm, from about 0.8 nm to about 2.6 nm, from about 0.8 nm to about 2.5 nm, from about 0.8 nm to about 2.4 nm, from about 0.8 nm to about 2.2 nm, from about 0.8 nm to about 2 nm, from about 0.8 nm to about 1.8 nm, from about 0.8 nm to about 1.6 nm, from about 0.8 nm to about 1.4 nm, from about 1 nm to about 2.8 nm, from about 1 nm to about 2.6 nm, from about 1 nm to about 2.5 nm, from about 1 nm to about 2.4 nm, from about 1 nm to about 2.2 nm, from about 1 nm to about 2 nm, from about 1 nm to about 1.8 nm, from about 1 nm to about 1.6 nm, from about 1 nm to about 1.4 nm, from about 1.2 nm to about 2.8 nm, from about 1.2 nm to about 2.6 nm, from about 1.2 nm to about 2.5 nm, from about 1.2 nm to about 2.4 nm, from about 1.2 nm to about 2.2 nm, from about 1.2 nm to about 2 nm, from about 1.2 nm to about 1.8 nm, from about 1.2 nm to about 1.6 nm, from about 1.6 nm to about 2.8 nm, from about 1.6 nm to about 2.6 nm, from about 1.6 nm to about 2.5 nm, from about 1.6 nm to about 2.4 nm, from about 1.6 nm to about 2.2 nm, from about 1.6 nm to about 2 nm, or from about 1.6 nm to about 1.8 nm.

Embodiment 17: The method of any one of the embodiments 1-16, wherein the SWCNT dimer comprises a first SWCNT monomer and a second SWCNT monomer, wherein each monomer is independently from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm in length, optionally the lengths of both monomers are substantially the same.

Embodiment 18: The method of any one of the embodiments 1-17, wherein the nanotube dimer comprises a terminal conjugation, optionally a covalent conjugation.

Embodiment 19: The method of any one of the embodiments 1-18, wherein the nanotube dimer is coated with an amphiphilic material.

Embodiment 20: The method of embodiment 19, wherein the amphiphilic material comprises a phospholipid or a block copolymer.

Embodiment 21: The method of any one of the embodiments 1-20, wherein the engineered lipid-based vesicle comprises two or more nanotube dimers, three or more nanotube dimers, four or more nanotube dimers, five or more nanotube dimers, six or more nanotube dimers, seven or more nanotube dimers, or eight or more nanotube dimers.

Embodiment 22: The method of any one of the embodiments 1-21, wherein each of the nanotube dimers do not interact or bind to another nanotube dimer within the engineered lipid-based vesicle.

Embodiment 23: The method of any one of the embodiments 1-22, wherein the engineered lipid-based vesicle has a defined valency per surface area of the lipid-based vesicle of from about 1 nanotube complex/100 nm$^2$ to about 100 nanotube complexes/100 nm$^2$, from about 2 nanotube complexes/100 nm$^2$ to about 100 nanotube complexes/100 nm$^2$, from about 3 nanotube complexes/100 nm$^2$ to about 100 nanotube complexes/100 nm$^2$, from about 5 nanotube complexes/100 nm$^2$ to about 100 nanotube complexes/100 nm$^2$, from about 10 nanotube complexes/100 nm$^2$ to about 100 nanotube complexes/100 nm$^2$, from about 20 nanotube complexes/100 nm$^2$ to about 100 nanotube complexes/100 nm$^2$, from about 30 nanotube complexes/100 nm$^2$ to about 100 nanotube complexes/100 nm$^2$, or from about 50 nanotube complexes/100 nm$^2$ to about 100 nanotube complexes/100 nm$^2$.

Embodiment 24: The method of any one of the embodiments 1-23, wherein the payload is a small molecule, a protein, a polypeptide, a nucleic acid molecule, a protein conjugate, polypeptide conjugate, a nucleic acid molecule conjugate, a polymer, or a gene-editing system.

Embodiment 25: The method of any one of the embodiments 1-24, wherein the payload is an antitumor agent, an antimicrobial agent, a contrast agent, an antioxidant, or an anti-inflammatory agent.

Embodiment 26: The method of any one of the embodiments 1-25, wherein the cell is a cancer cell, a cell that is infected with a pathogen, a cell that is associated with an autoimmune disease, or a cell that is associated with an inflammation.

Embodiment 27: The method of any one of the embodiments 1-23 or 26, wherein the payload is a dye.

Embodiment 28: The method of embodiment 27, further comprising visualizing the cell.

Embodiment 29: The method of embodiment 28, wherein the cell is from a biopsy, optionally a tumor biopsy.

Embodiment 30: The method of any one of the embodiments 1-29, wherein the method is an in vitro, in vivo, or an ex vivo method.

Embodiment 31: A method of delivering a payload to a target, comprising contacting the target with an engineered lipid-based vesicle comprising a nanotube dimer embedded within the lipid bilayer circumference of the lipid-based vesicle and a payload, wherein the nanotube dimer induces a fusion of the engineered lipid-based vesicle and the target, thereby delivering the payload to the target.

Embodiment 32: The method of embodiment 31, wherein the engineered lipid-based vesicle has a diameter of at least 28 nm, at least 30 nm, at least 35 nm, at least 40 nm, at least 50 nm, at least 100 nm, at least 200 nm, or larger.

Embodiment 33: The method of embodiment 31 or 32, wherein the engineered lipid-based vesicle is a liposome, optionally selected from a multilamellar vesicle (MLV), small unilamellar liposome vesicle (SUV), large unilamellar vesicle (LUV), giant unilamellar liposome (GUV), or a cochleate vesicle.

Embodiment 34: The method of any one of the embodiments 31-33, wherein the liposome comprises a natural phospholipid, a synthetic phospholipid, an unsaturated lipid, a saturated lipid, a lysolipid, a sphingolipid, a glycosphingolipid, a steroid, a charge-inducing lipid, or a combination thereof.

Embodiment 35: The method of embodiment 34, wherein the natural phospholipid comprises phosphotidylcholine, phosphotidylserine, phosphotidylethanolamine, or phosphatidylinositol.

Embodiment 36: The method of embodiment 34, wherein the synthetic phospholipid comprises phosphatidic acid, phosphatidylcholine, phosphatidylglycerol, phosphatidylethanolamine, phosphatidylserine, or PEG phospholipid.

Embodiment 37: The method of embodiment 34 or 36, wherein the synthetic phospholipid comprises DEPA-NA, DLPA-NA, DMPA-NA, DOPA-NA, DPPA-NA, DSPA-NA, DEPE, DLPE, DMPE, DOPE, DPPE, DSPE, POPE, DLPS-NA, DMPS-NA, DOPS-NA, DPPS-NA, DSPS-NA, DDPC, DEPC, DLOPC, DLPC, DMPC, DOPC, DPPC, DSPC, LYSOPC MYRISTIC, LYSOPC PALMITIC, LYSOPC STEARIC, Milk Sphingomyelin MPPC, MSPC, PMPC, POPC, PSPC, SMPC, SOPC, SPPC, DEPG-NA, DLPG-NA, DLPG-NH4, DMPG-NA, DMPG-NH4, DMPG-NH4/NA, DOPG-NA, DPPG-NA, DPPG-NH4, DSPG-NA, DSPG-NH4, POPG-NA, HSPC, or a combination thereof.

Embodiment 38: The method of embodiment 34, wherein the unsaturated lipid comprises 1-stearoyl-2-linoleoyl-sn-glycero-3-[phosphor-L-serine] or dioleaylphosphtidylcholine.

Embodiment 39: The method of embodiment 34, wherein the sphingolipid comprises sphingomyelin.

Embodiment 40: The method of embodiment 34, wherein the glycosphingolipid comprises ganglioside.

Embodiment 41: The method of embodiment 34, wherein the steroid comprises cholesterol or a cholesterol derivative, wherein the cholesterol derivative is optionally DC-cholesterol.

Embodiment 42: The method of embodiment 34, wherein the charge-inducing lipid comprises diotadecyldimethyl ammonium bromide/chloride (DODAB/C), dioleoyl trimethylammonium propane (DOTAP), or ionizable lipids (DLIN-MC3-DMA).

Embodiment 43: The method of embodiment 31 or 32, wherein the lipid-based vesicle is an extracellular vesicle (EV), optionally an exosome or a microvesicle.

Embodiment 44: The method of any one of the embodiments 31-43, wherein the nanotube dimer comprises a carbon nanotube dimer, a boron nitride nanotube (BNNT) dimer, a $MoS_2$ nanotube dimer, a $MoS_2$-carbon nanotube hybrid dimer, or a carbon-$MoS_2$—$WS_2$ nanotube hybrid dimer.

Embodiment 45: The method of any one of the embodiments 31-44, wherein the carbon nanotube dimer is a single-walled carbon nanotube (SWCNT) dimer, optionally a conjugated SWCNT dimer.

Embodiment 46: The method of any one of the embodiments 31-45, wherein the SWCNT dimer comprises a total inner diameter across the major axis of the dimer of from about 0.8 nm to about 2.8 nm, from about 0.8 nm to about 2.6 nm, from about 0.8 nm to about 2.5 nm, from about 0.8 nm to about 2.4 nm, from about 0.8 nm to about 2.2 nm, from about 0.8 nm to about 2 nm, from about 0.8 nm to about 1.8 nm, from about 0.8 nm to about 1.6 nm, from about 0.8 nm to about 1.4 nm, from about 1 nm to about 2.8 nm, from about 1 nm to about 2.6 nm, from about 1 nm to about 2.5 nm, from about 1 nm to about 2.4 nm, from about 1 nm to about 2.2 nm, from about 1 nm to about 2 nm, from about 1 nm to about 1.8 nm, from about 1 nm to about 1.6 nm, from about 1 nm to about 1.4 nm, from about 1.2 nm to about 2.8 nm, from about 1.2 nm to about 2.6 nm, from about 1.2 nm to about 2.5 nm, from about 1.2 nm to about 2.4 nm, from about 1.2 nm to about 2.2 nm, from about 1.2 nm to about 2 nm, from about 1.2 nm to about 1.8 nm, from about 1.2 nm to about 1.6 nm, from about 1.6 nm to about 2.8 nm, from about 1.6 nm to about 2.6 nm, from about 1.6 nm to about 2.5 nm, from about 1.6 nm to about 2.4 nm, from about 1.6 nm to about 2.2 nm, from about 1.6 nm to about 2 nm, or from about 1.6 nm to about 1.8 nm.

Embodiment 47: The method of any one of the embodiments 31-46, wherein the SWCNT dimer comprises a first SWCNT monomer and a second SWCNT monomer, wherein each monomer is independently from about 6 nm to about 30 nm, from about 6 nm to about 25 nm, from about 6 nm to about 20 nm, from about 6 nm to about 15 nm, from about 6 nm to about 14 nm, from about 6 nm to about 13 nm, from about 6 nm to about 12 nm, from about 6 nm to about 11 nm, from about 6 nm to about 10 nm, from about 6 nm to about 9 nm, from about 6 nm to about 8 nm, from about 8 nm to about 30 nm, from about 8 nm to about 25 nm, from about 8 nm to about 20 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, from about 9 nm to about 30 nm, from about 9 nm to about 25 nm, from about 9 nm to about 20 nm, from about 9 nm to about 15 nm, from about 9 nm to about 14 nm, from about 9 nm to about 13 nm, from about 9 nm to about 12 nm, from about 9 nm to about 11 nm, from about 9 nm to about 10 nm, from about 10 nm to about 30 nm, from about 10 nm to about 25 nm, from about 10 nm to about 20 nm, from about 10 nm to about 15 nm, from about 10 nm to about 14 nm, from about 10 nm to about 13 nm, from about 10 nm to about 12 nm, from about 10 nm to about 11 nm, from about 11 nm to about 30 nm, from about 11 nm to about 25 nm, from about 11 nm to about 20 nm, from about 11 nm to about 15 nm, from about 11 nm to about 14 nm, from about 11 nm to about 13 nm, from about 11 nm to about 12 nm, from about 12 nm to about 30 nm, from about 12 nm to about 25 nm, from about 12 nm to about 20 nm, from about 12 nm to about 15 nm, from about 12 nm to about 14 nm, or from about 12 nm to about 13 nm in length, optionally the lengths of both monomers are substantially the same.

Embodiment 48: The method of any one of the embodiments 31-47, wherein the nanotube dimer comprises a terminal conjugation, optionally a covalent conjugation.

Embodiment 49: The method of any one of the embodiments 31-48, wherein the nanotube dimer is coated with an amphiphilic material.

Embodiment 50: The method of embodiment 49, wherein the amphiphilic material comprises a phospholipid or a block copolymer.

Embodiment 51: The method of anyone of the embodiments 31-50, wherein the engineered lipid-based vesicle comprises two or more nanotube dimers, three or more nanotube dimers, four or more nanotube dimers, five or more nanotube dimers, six or more nanotube dimers, seven or more nanotube dimers, or eight or more nanotube dimers.

Embodiment 52: The method of anyone of the embodiments 31-51, wherein each of the nanotube dimers do not interact or bind to another nanotube dimer within the engineered lipid-based vesicle.

Embodiment 53: The method of any one of the embodiments 31-52, wherein the engineered lipid-based vesicle has a defined valency per surface area of the lipid-based vesicle of from about 1 nanotube complex/100 $nm^2$ to about 100 nanotube complexes/100 $nm^2$, from about 2 nanotube complexes/100 $nm^2$ to about 100 nanotube complexes/100 $nm^2$, from about 3 nanotube complexes/100 $nm^2$ to about 100 nanotube complexes/100 $nm^2$, from about 5 nanotube complexes/100 $nm^2$ to about 100 nanotube complexes/100 $nm^2$, from about 10 nanotube complexes/100 $nm^2$ to about 100 nanotube complexes/100 $nm^2$, from about 20 nanotube complexes/100 $nm^2$ to about 100 nanotube complexes/100 $nm^2$, from about 30 nanotube complexes/100 $nm^2$ to about 100 nanotube complexes/100 $nm^2$, or from about 50 nanotube complexes/100 $nm^2$ to about 100 nanotube complexes/100 $nm^2$.

Embodiment 54: The method of any one of the embodiments 31-53, wherein the payload is a small molecule, a protein, a polypeptide, a nucleic acid molecule, a protein conjugate, polypeptide conjugate, a nucleic acid molecule conjugate, a polymer, or a gene-editing system.

Embodiment 55: The method of any one of the embodiments 31-54, wherein the payload is an antitumor agent, an antimicrobial agent, a contrast agent, an antioxidant, or an anti-inflammatory agent.

Embodiment 56: The method of any one of the embodiments 31-54, wherein the payload is a dye.

Embodiment 57: The method of any one of the embodiments 31-56, wherein the target is a target cell.

Embodiment 58: The method of embodiment 57, wherein the target cell is a cancer cell, a cell that is infected with a pathogen, a cell that is associated with an autoimmune disease, or a cell that is associated with an inflammation.

Embodiment 59: The method of any one of the embodiments 31-56, wherein the target is an extracellular vesicle or a viral particle, wherein the extracellular vesicle is optionally an exosome or a microvesicle.

REFERENCES

1. Smith, W. *Mechanisms of virus infection* (Academic Press, London & New York, 1963).
2. Harrison, S. C. Viral membrane fusion. *Nat. structural molecular biology* 15, 690 (2008).
3. Epand, R. M. Fusion peptides and the mechanism of viral fusion. *Biochimica et Biophys. Acta (BBA)-Biomembranes* 1614, 116-121 (2003).
4. Geng, J. et al. Stochastic transport through carbon nanotubes in lipid bilayers and live cell membranes. *Nature* 514, 612-615 (2014).
5. Bhaskara, R. M., Linker, S. M., Vögele, M., Kfinger, J. & Hummer, G. Carbon nanotubes mediate fusion of lipid vesicles. *ACS Nano* 11, 1273-1280 (2017).
6. Forterre, P. The origin of viruses and their possible roles in major evolutionary transitions. *Virus Res.* 117, 5-16, DOI: //doi.org/10.1016/j.virusres.2006.01.010 (2006). Comparative Genomics and Evolution of Complex Viruses.
7. Chernomordik, L. V. & Kozlov, M. M. Mechanics of membrane fusion. *Nat. structural molecular biology* 15, 675 (2008).
8. Sercombe, L. et al. Advances and challenges of liposome assisted drug delivery. *Front. Pharmacology* 6, 286 (2015).
9. Zylberberg, C. & Matosevic, S. Pharmaceutical liposomal drug delivery: a review of new delivery systems and a look at the regulatory landscape. *Drug Deliv.* 23, 3319-3329 (2016).
10. Kanamala, M., Wilson, W. R., Yang, M., Palmer, B. D. & Wu, Z. Mechanisms and biomaterials in ph-responsive tumour targeted drug delivery: a review. *Biomaterials* 85, 152-167 (2016).
11. G Moussa, H., M Martins, A. & A Husseini, G. Review on triggered liposomal drug delivery with a focus on ultrasound. *Curr. cancer drug targets* 15, 282-313 (2015).
12. Kneidl, B., Peller, M., Winter, G., Lindner, L. H. & Hossann, M. Thermosensitive liposomal drug delivery systems: state of the art review. *Int. journal nanomedicine* 9, 4387 (2014).
13. Frangois-Martin, C., Rothman, J. E. & Pincet, F. Low energy cost for optimal speed and control of membrane fusion. *Proc. Natl. Acad. Sci.* 114, 1238-1241 (2017).
14. Fornasiero, F. et al. ph-tunable ion selectivity in carbon nanotube pores. *Langmuir* 26, 14848-14853 (2010).
15. Tunuguntla, R. H., Escalada, A., Frolov, V. A. & Noy, A. Synthesis, lipid membrane incorporation, and ion permeability testing of carbon nanotube porins. *Nat. protocols* 11, 2029 (2016).
16. Timko, B. P. et al. Advances in drug delivery. *Annu. Rev. Mater. Res.* 41, 1-20 (2011).
17. Bennett, J. W. & Chung, K.-T. Alexander Fleming and the discovery of penicillin. *Adv. Appl. Microbiol.* 49, 163-184 (2001).
18. Katzung, B. G. *Basic & Clinical Pharmacology* (McGraw-Hill, New York, 2018), 14th edn.
19. Chabner, B. A. & Roberts, T. G. Chemotherapy and the war on cancer. *Nat. Rev. Cancer* 5, 65-72 (2005).
20. Rosen, Y., Gurman, P. & Elman, N. *Drug delivery: An integrated clinical and engineering approach* (CRC Press, 2017).
21. Peer, D. et al. Nanocarriers as an emerging platform for cancer therapy. *Nat. Nanotechnol.* 2, 751 (2007).
22. Wilhelm, S. et al. Analysis of nanoparticle delivery to tumours. *Nat. Rev. Mater.* 1, 1-12 (2016).
23. Sudhof, T. C. & Rothman, J. E. Membrane fusion: grappling with snare and sm proteins. *Science* 323, 474-477 (2009).
24. Harrison, S. C. Viral membrane fusion. *Virology* 479, 498-507 (2015).
25. Earp, L., Delos, S., Park, H. & White, J. The many mechanisms of viral membrane fusion proteins. In *Membrane trafficking in viral replication*, 25-66 (Springer, 2004).
26. Kielian, M. & Rey, F. A. Virus membrane-fusion proteins: More than one way to make a haripin. *Nat. Rev.—Microbiol.* 4, 67-76 (2005).
27. Struck, D. K., Hoekstra, D. & Pagano, R. E. Use of resonance energy transfer to monitor membrane fusion. *Biochemistry* 20, 4093-4099 (1981).
28. Weber, T. et al. SNAREpins: minimal machinery for membrane fusion. *Cell* 92, 759-772 (1998).
29. Kyoung, M. et al. In vitro system capable of differentiating fast Ca2+-triggered content mixing from lipid exchange for mechanistic studies of neurotransmitter release. *Proc. Natl. Acad. Sci. USA* 108, 304-313 (2011).
30. Barenholz, Y. C. Doxil®—the first FDA-approved nano-drug: lessons learned. *J. Control. Release* 160, 117-134 (2012).
31. Soundararajan, A., Bao, A., Phillips, W. T., Perez III, R. & Goins, B. A. Re-liposomal doxorubicin (Doxil): In vitro stability, pharmacokinetics, imaging and biodistribution in a head and neck squamous cell carcinoma xenograft model. *Nucl. Medicine Biol.* 36, 515-524 (2009).
32. Tojima, T., Yamane, Y., Takahashi, M. & Ito, E. Acquisition of neuronal proteins during differentiation of NG108-15 cells. *Neurosci. Res.* 37, 153-161 (2000).
33. Ruggiero, A. et al. Paradoxical glomerular filtration of carbon nanotubes. *Proc. Natl. Acad. Sci. USA* 107, 12369-12374 (2010).
34. Alidori, S. et al. Carbon nanotubes exhibit fibrillar pharmacology in primates. *PloS One* 12 (2017).
35. Rawson, F. J., Garrett, D. J., Leech, D., Downard, A. J. & Baronian, K. H. Electron transfer from *Proteus vulgaris* to a covalently assembled, single walled carbon nanotube electrode functionalised with osmium bipyridine complex: Application to a whole cell biosensor. *Biosens. Bioelectron.* 26, 2383-2389 (2011).
36. Ong, S. G., Ming, L.-C., Lee, K.-S. & Yuen, K.-H. Influence of the encapsulation efficiency and size of liposome on the oral bioavailability of griseofulvin-loaded liposomes. *Pharmaceutics* 8, 1-17 (2016).
37. Focke, W. W., Van der Westhuizen, I., Musee, N. & Loots, M. T. Kinetic interpretation of log-logistic dose-time response curves. *Sci. Reports* 7, 1-11 (2017).
38. Marrink, S. J., Risselada, H. J., Yefimov, S., Tieleman, D. P. & De Vries, A. H. The MARTINI force field: Coarse grained model for biomolecular simulations. *J. Phys. Chem. B* 111, 7812-7824 (2007).

39. Abraham, M. J. et al. GROMACS: High performance molecular simulations through multi-level parallelism from laptops to supercomputers. Software X 1-2, 19-25 (2015).
40. De Jong, D. H., Baoukina, S., Ingólfsson, H. I. & Marrink, S. J. Martini straight: Boosting performance using a shorter cutoff and GPUs. Comput. Phys. Commun. 199, 1-7 (2016).
41. Bussi, G., Donadio, D. & Parrinello, M. Canonical sampling through velocity rescaling. J. Chem. Phys. 126, 014101 (2007).
42. Parrinello, M. & Rahman, A. Polymorphic transitions in single crystals: A new molecular dynamics method. J. Appl. Phys. 52, 7182-7190 (1981).
43. Vogele, M. & Hummer, G. Divergent Diffusion Coefficients in Simulations of Fluids and Lipid Membranes. J. Phys. Chem. B 120, 8722-8732 (2016).
44. Dan, N. Drug release through liposome pores. Colloids Surfaces B: Biointerf. 126, 80-86 (2015).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of fusing lipid bilayers, the method comprising:
    contacting (a) an engineered unilamellar liposome comprising a first lipid bilayer and a nanotube dimer embedded in a circumference of the first lipid bilayer with (b) a second lipid bilayer, wherein:
    said contacting results in fusing the first lipid bilayer with the second lipid bilayer into a single lipid bilayer,
    the nanotube dimer comprises a first nanotube and a second nanotube, which is essentially parallel to the first nanotube, and
    the nanotube dimer has an asymmetric cross section perpendicular to a length direction of the first nanotube and the second nanotube, so that the dimer has a wider hydrophobic facet and a narrower facet, each of the wider hydrophobic facet and the narrower facet extends along the length direction of the first nanotube and the second nanotube, and the wider facet has a larger dimension in the asymmetric cross section than the narrower facet.

2. The method of claim 1, wherein the liposome has a diameter across the major axis of the liposome of at least about 28 nm.

3. The method of claim 1, wherein the liposome has a diameter across the major axis of the liposome of at least about 300 nm.

4. The method of claim 1, wherein each of the first nanotube and the second nanotube is a nanotube selected from the group consisting of a carbon nanotube, a boron nitride nanotube, a $MoS_2$ nanotube, a $MoS_2$-carbon nanotube hybrid, and a carbon-$MoS_2$—$WS_2$ nanotube hybrid.

5. The method of claim 1, wherein each of the first nanotube and the second nanotube is a carbon nanotube.

6. The method of claim 1, wherein each of the first nanotube and the second nanotube is a single wall carbon nanotube.

7. The method of claim 1, wherein each of the first nanotube and the second nanotube has an outer diameter of from about 0.7 nm to about 2 nm.

8. The method of claim 1, wherein each of the first nanotube and the second nanotube a length from about 6 nm to about 30 nm.

9. The method of claim 1, wherein each of the first nanotube and the second nanotube comprises a terminal COOH group and wherein the dimer comprises a carbodiimide crosslinker linking the first nanotube to the second nanotubes through respective terminal COOH groups.

10. The method of claim 1, wherein the dimer is formed by reacting a terminal alkyne group on the first nanotube with a terminal azide group of the second nanotube.

11. The method of claim 1, wherein the second lipid bilayer is a lipid bilayer of a cell.

12. The method of claim 11, wherein the engineered unilamellar liposome comprises a payload and wherein said fusing delivers the payload to the cell.

13. The method of claim 12, wherein the payload is a drug.

14. The method of claim 12, wherein the payload is a small molecule, a protein, a polypeptide, a nucleic acid molecule, a protein conjugate, polypeptide conjugate, a nucleic acid molecule conjugate, a polymer, a dye, or a gene-editing system.

15. The method of claim 14, wherein the payload is an antitumor agent, an antimicrobial agent, a contrast agent, an antioxidant, or an anti-inflammatory agent.

16. The method of claim 12, wherein the payload is doxorubicin.

17. The method of claim 12, wherein the cell is a cancer cell, a cell that is infected with a pathogen, a cell that is associated with an autoimmune disease, or a cell that is associated with an inflammation.

18. The method of claim 1, wherein the first lipid bilayer comprises one or more phospholipids.

19. The method of claim 18, wherein the first lipid bilayer further comprises cholesterol.

20. The method of claim 1, wherein the first lipid bilayer comprises one or more PEG-lipids.

* * * * *